United States Patent [19]

Takeuchi et al.

[11] Patent Number: 5,527,781

[45] Date of Patent: Jun. 18, 1996

[54] 4-O-(AMINOGLYCOSYL)- OR 4,6-DI-O-(AMINOGLYCOSYL)-2,5-DIDEOXY-5,5-DIFLUOROSTREPTAMINE DERIVATIVES

[75] Inventors: Tomio Takeuchi; Sumio Umezawa, both of Tokyo; Tsutomu Tsuchiya, Yokohama; Tetsuo Shitara, Kawasaki; Shunzo Fukatsu, Haraikata-machi; Eijiro Umemura, Chigasaki, all of Japan

[73] Assignee: Zaidan Hojin Biseibutsu Kagaku Kenkyu Kai, Tokyo, Japan

[21] Appl. No.: 39,447

[22] PCT Filed: Aug. 22, 1991

[86] PCT No.: PCT/JP91/01115

§ 371 Date: Apr. 21, 1993

§ 102(e) Date: Apr. 21, 1993

[87] PCT Pub. No.: WO92/03460

PCT Pub. Date: Mar. 3, 1992

[30] Foreign Application Priority Data

Aug. 24, 1990 [JP] Japan .................... 2-221085

[51] Int. Cl.[6] .................... A61K 31/70; C07H 15/22
[52] U.S. Cl. .................... 514/41; 514/36; 514/40; 536/13.6; 536/13.7; 536/13.8
[58] Field of Search .................... 514/41, 36, 40; 536/13.6, 13.7, 13.8

[56] References Cited

U.S. PATENT DOCUMENTS

| | | | |
|---|---|---|---|
| 4,284,764 | 8/1981 | Daniels et al. | 536/13.6 |
| 4,547,492 | 10/1985 | Umezawa et al. | 514/41 |
| 4,873,225 | 10/1989 | Umezawa et al. | 514/41 |

*Primary Examiner*—Elli Peselev
*Attorney, Agent, or Firm*—Larson and Taylor

[57] ABSTRACT

As new compounds are now synthetized 5-deoxy-5,5-difluoro derivatives of aminoglycosidic antibiotics of neamine, kanamycin A-series, kanamycin B-series, gentamicin-series and seldomycin-series. Further, the 1-N-(α-hydroxy-ω-aminoalkanoyl) derivatives are synthetized from 5-deoxy-5,5-difluorokanamycins A and B, as well as their analogues now obtained. The 5-deoxy-5,5-difluoro derivatives of the aminoglycosidic antibiotics now provided according to this invention have such antibacterial activities enhanced much more than or equal to those of the respectively corresponding parent aminoglycosidic antibiotics, while these 5-deoxy-5,5-difluoro derivatives exhibit values of the 50% lethal dosage ($LD_{50}$) which are improved remarkably better when they are intravenously administered to mice, so that they have remarkedly reduced toxicities to mammals.

12 Claims, No Drawings

4-O-(AMINOGLYCOSYL)- OR 4,6-DI-O-(AMINOGLYCOSYL)-2,5-DIDEOXY-5,5-DIFLUOROSTREPTAMINE DERIVATIVES

TECHNICAL FIELD

This invention relates to new semi-synthetic aminoglycosidic antibiotics, namely such 5-deoxy-5,5-difluorostreptamine derivatives which are derived from aminoglycosidic antibiotics or their deoxy derivatives, as well as 1-N-acylated derivatives of said 5-deoxy-5,5-difluorostreptamine derivatives. This invention also relates to antibacterial compositions containing these new compounds. Further, this invention relates to processes for the production of these new compounds. These new compounds of this invention are useful as antibacterial agent for therapeutic treatment of bacterial infections, since they exhibit high antibacterial activities against such bacteria sensitive to aminoglycosidic antibiotics, and also against such bacteria resistant to aminoglycosidic antibiotics and have a characteristically and remarkably reduced toxicity.

BACKGROUND ART

Various deoxy derivatives of kanamycin A, B or C have useful antibacterial activities, but the antibacterial spectra of these known deoxy-derivatives of kanamycins are of different ranges. Accordingly, it is always demanded that new, antibacterial compounds having any more excellent properties than the known kanamycin derivatives should be produced and provided.

The present inventors have synthetized 3'-deoxy-3'-fluorokanamycin A (see Japanese patent application first publication "Kokai" No. 40297/86 and U.S. Pat. No. 4,634,688). Further, the present inventors have synthetized 3'-deoxy-3'-fluorokanamycin B and found that 3'-deoxy-3'-fluorokanamycin B has remarkable antibacterial activities against various gram-positive and gram-negative bacteria, including the resistant bacteria (see Japanese patent application first publication "Kokai" No. 140597/86). And, the present inventors have synthetized 3',4'-dideoxy-3'-fluorokanamycin B (see Japanese patent application first publication "Kokai" No. 51694/87 and U.S. Pat. No. 4,845,082 specification).

Furthermore, the present inventors have synthetized 1-N-[(RS)- or (S)-3-amino-2-hydroxy-propionyl]- or 1-N-[(S)-4-amino-2-hydroxybutyryl]-3'-deoxy-3'-fluorokanamycin A or B (see Japanese patent application first publication "Koaki" No. 236791/86).

Moreover, the present inventors have synthetized 2',3'-dideoxy-2'-fluorokanamycin A (see the specification of Japanese patent application first publication "Kokai" No. 143393/86) as well as 1-N-[(RS)- or (S)-3-amino-2-hydroxypropionyl]- or 1-N-[(S)-4-amino-2-hydroxybutyryl]-2',3'-dideoxy-2'-fluorokanamycin A (see Japanese patent application first publication "Koaki" No. 93296/87 and U.S. Pat. No. 4,661,474 specification).

On the other hand, a literature "Aminocyclitol Antibiotics" pages 371–392, edited by K. L. Rinehart and T. Suami (published from American Chemical Society in 1980) discloses the production of 5-deoxy-5-fluoro-5-epi-sisomicin according to a method comprising reacting diethylaminosulfur trifluoride (hereinafter abbreviated as DAST) with such a protected derivative of sisomicin whose all the amino groups and all the hydroxyl groups except the 5-hydroxyl group have been protected. Further, a literature "Journal of Carbohydrate Chemistry" Vol. 1, page 289 (1982) discloses the production of 4"-deoxy-4"-fluoro-4"-epi-kanamycin A with starting from kanamycin A, although this literature shows that the antibacterial activity of this 4"-deoxy-4"-fluoro-4"-epi-kanamycin A is lower than that of kanamycin A.

Furthermore, a literature "Tetrahedron Letters" Vol. 24, No. 17, pages 1763–1766(1983) discloses that 6"-deoxy-6"-fluorokanamycin A is produced, that 5,6"-dideoxy-5,6"-difluoro-5-epi-kanamycin A is produced and further that 5-deoxy-5-fluoro-5,4"-di-epi-kanamycin A is produced.

In this literature "Tetrahedron Letters" Vol. 24, No. 17, pages 1763–1766(1983), there is disclosed that 6"-deoxy-6"-fluorokanamycin A, 5,6"-dideoxy-5,6"-difluoro-5-epi-kanamycin A and 5-deoxy-5-fluoro-5,4"-di-epi-kanamycin A show antibacterial activities substantially as high as that of kanamycin A. Accordingly, this literature does not give any teaching that the antibacterial activity of kanamycin A can be enhanced by replacement of the 6"-hydroxyl group and/or the 5-hydroxyl group of kanamycin A by a fluorine atom. In this literature, there is not given any reference to toxicity and other biological activities of the fluorokanamycin A derivatives disclosed therein.

In another literature "Chemical Abstracts" 90, 104, 301 (1979), there is disclosed a method of producing 5-deoxy-5-fluoro-5-epi-kanamycin A, which comprises reacting DAST with a protected derivative of kanamycin A whose the amino groups and the hydroxyl groups other than the 5-hydroxyl group have been protected with conventional protective groups. But, this literature does not disclose that antibacterial activity of 5-deoxy-5-fluoro-5-epi-kanamycin A so obtained is improved over that of kanamycin A.

As will be clear from the above, hithertobefore it has not been found that the antibacterial activity of sisomicin can advantageously be improved with the cases of 5-deoxy-5-fluoro-5-epi-sisomicin and 5-deoxy-5-fluoro-sisomicin which are obtained by reacting the 5-hydroxyl group with DAST and thereby replacing the 5-hydroxyl group by a fluorine atom, with or without possible concomitant inversion of the steric arrangement of the 5-substituent. Besides, it has not yet been recognized that the antibacterial activity of kanamycin A can advantageously be enhanced with the case of the 5-deoxy-5-fluoro-5-epi-kanamycin A, as compared to the parent kanamycin A.

Thus, the present inventors have already found that 3'-deoxy-3'-fluorokanamycin A or B, 3',4'-dideoxy-3'-fluorokanamycin B and 2',3'-dideoxy-2'-fluorokanamycin A can each exhibit their improved antibacterial activities, as compared to those of their corresponding parent compounds not having the fluoro substituent. On the other hand, the present inventors have recognized that the replacemnt of the 5-hydroxyl group of sisomicin or kanamycin A by the fluoro substituent cannot bring about any advantageous improvement or enhancement in the antibacterial activity of the parent sisomicin or kanamycin A. Despiting this recognition, the present inventors have studied to synthetize 5-deoxy-5-fluorokanamycin B. In addition to our success to synthetize 5-deoxy-5-fluorokanamycin B, the present inventors have succeeded in synthetizing 5,3'-dideoxy-5-fluorokanamycin B from 3'-deoxy-kanamycin B (namely, tobramycin); 5,4'-dideoxy-5-fluorokanamycin B from 4'-deoxykanamycin B (see the "Bull. Chem. Soc. Jpn." 50, page 2362 (1977)); and 5,3',4'-trideoxy-5-fluorokanamycin B from 3',4'-dideoxykanamycin B (namely, dibekacin) (see the specification of Japanese patent application first publication "Kokai" No. 39891/88 and European patent application publication No. 0 259 014 A2).

Hithertobefore, the aminoglycosidic antibiotics have been used in clinics to exhibit such excellent curative effects in the therapeutic treatment of bacterial infections that are not obtainable with the other kinds of antibiotics, because the aminoglycosidic antibiotics are soluble in water and hence are well systemic to the tissues of human body. By virtue of this, the aminoglycosidic antibiotics are frequently utilized in the therapeutic treatment of patients suffering from heavy bacterial infections for which the other kinds of antibiotics are not effective. In this therapeutic treatment with the aminoglycosidic antibiotics, however, intravenous injection of aqueous solutions of the aminoglycosidic antibiotics is usually and mainly made, so that the acute toxicity of the aminoglycosidic antibiotics is rapid to develop in the patients as treated, often resulting in that dosage of said antibiotics must be reduced and/or administration of said antibiotics must be interrupted. In recent years, therefore, the doctors in hospitals are likely to have an idea that the aminoglycosidic antibiotics are of high toxicity. Thus, there prevails actually such a tendency that the doctors would have a fear to the toxicity of the aminoglycosidic antibiotics and rather refrain from administering the aminoblycosidic antibiotics to such patients which should need to be therapeutically treated by administration of the aminoglycosidic antibiotics.

The present inventors have made efforts for 10 years or more in the past to solve the problem that the toxicity of the aminoglycosidic antibiotics is reduced. During recent investigations, the present inventors incidentally have discovered that the above-mentioned 5-deoxy-5-fluorokanamycin B now synthetized and its analogues show a more or less reduced toxicity ($LD_{50}$ value of ca. 135 mg/kg) upon intravenous injection of them. With regard to a reason why the introduction of a fluorine atom in the 5-position of kanamycin B and its analogues can reduce the toxicity of kanamycin B etc., through any mechanism, the present inventors have studied it with groping in the dark. As an outcome, however, the present inventors have now reached in getting a presumption that the 5-fluoro substitutent can result in a reduction in the basicity of the 3-amino group of kanamycins and consequently result in a reduction in the toxicity of kanamycins.

On the basis of this discovery, the present inventors have now presumed that, in general, if there can be synthetized such 5-deoxy-5,5-difluoro derivatives of the aminoglycosidic antibiotics in which two fluoro substituents have been introduced into the 5-position of the aminoglycosidic antibiotics, new semi-synthetic aminoglycosidic antibiotics having a further reduced toxicity can be provided.

DISCLOSURE OF THE INVENTION

The present inventors have made extensive research based on the above-mentioned presumption, and as a result, have now succeeded in synthetizing as new compounds such 5-deoxy-5,5-difluoro derivatives of the aminoglycosidic antibiotics, including those of neamine, kanamycin A-series, kanamycin B-series, gentamicin-series and seldomycin-series. Also, the present inventors have succeeded in synthetizing 1-N-(α-hydroxy-ω-aminoalkanoyl) derivatives from 5-deoxy-5,5-difluorokanamycins A and B, as well as their analogues.

Further, according to the findings now obtained by the present inventors, it has been recognized that the 5-deoxy-5,5-difluoro derivatives of the aminoglycosidic antibiotics now synthetized exhibit antibacterial activities enhanced much than or substantially equal to the antibacterial activities of their respectively corresponding parent aminoglycosidic antibiotics in respect of their minimum growth inhibitory concentrations (MIC.) (as measured according to a standard serial dilution method in vitro) against some species or strains of bacteria, and that when the aforesaid 5-dideoxy-5,5-difluoro derivatives of the aminoglycosidic antibiotics are intravenously administered to mice as one of mammals, their 50% lethal dosages ($LD_{50}$) are remarkably improved better. Thus, it has been found that the acute toxicity of the 5-deoxy-5,5-difluoro derivatives of the aminoglycosidic antibiotics, namely the new compounds now synthetized by the present inventors have been reduced to a half or less, as compared to that of the respectively corresponding parent aminoglycosidic antibiotics, when they are intravenously administered to mice.

Next, this invention is described in more details. The known aminoglycosidic antibiotics and their known semisynthetic derivatives include neamine, 3',4'-dideoxyneamine, kanamycin A, 3'-deoxykanamycin A, 3',4'-dideoxykanamycin A, kanamycin B, 3'-deoxykanamycin B (namely, tobramycin), 3'-deoxy-3'-fluorokanamycin B, 3',4'-dideoxykanamycin B (namely, dibekacin), 3',4'-dideoxy-3'-fluorokanamycin B, gentamicin $C_1$, gentamicin $C_{1a}$, gentamicin $C_2$, sagamicin, sisomicin, netilmicin and seldomycin factor 3 etc., which may generically be represented by the general formula

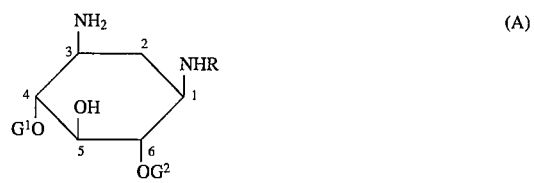

wherein R is a hydrogen atom or ethyl group, $G^1$ is either an aminoglycosyl group of the formula

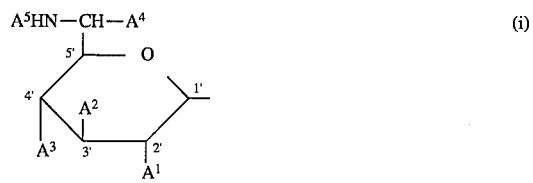

where $A^1$ is a hydroxyl group or amino group, $A^2$ and $A^3$ are independently a hydrogen atom, hydroxyl group or fluoro group, $A^4$ is a hydrogen atom or methyl group, and $A^5$ is a hydrogen atom or methyl group, or a 4'-eno-aminoglycosyl group of the formula

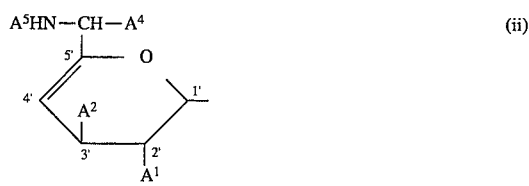

where $A^1$, $A^2$, $A^4$ and $A^5$ independently have the same meanings as defined above, and $G^2$ is either a hydrogen atom, or a 3"-amino-3"-deoxyglycosyl group of the formula

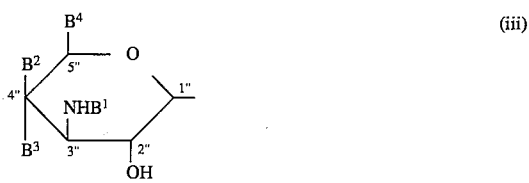

where $B^1$ is a hydrogen atom or methyl group, $B^2$ and $B^3$ are independently a hydrogen atom, hydroxyl group or methyl group, and $B^4$ is a hydrogen atom or a hydroxymethyl group (—$CH_2OH$), or a 2"-amino-2"-deoxyglycosyl group of the formula

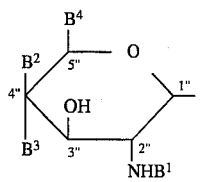

(iv)

where $B^1$, $B^2$, $B^3$ and $B^4$ independently have the same meanings as defined above.

To produce synthetically the above-mentioned 5-deoxy-5,5-difluoro derivative of aminoglycosidic antibiotics with starting from 4-O-(aminoglycosyl)- or 4,6-di-O-(aminoglycosyl)-2-deoxystreptamines represented by the general formula (A) above, a reaction stage is firstly conducted, where all the amino groups of the starting 2-deoxystreptamine compound of the general formula (A) are protected according to the known amino-protecting methods, such as acylation (e.g., acetylation or benzoylation etc.,), conversion into urethane derivative (e.g., by methoxycarbonylation, ethoxycarbonylation, phenoxycarbonylation or benzyloxycarbonylation etc.,), or sulfonylation (e.g., tosylation etc.,). Subsequently, a reaction stage is conducted, where all the hydroxyl groups other than the 5-hydroxyl group of the amino-protected derivative prepared in the preceeding step are protected according to the known hydroxyl-protecting methods, such as acetylation or benzoylation. At this time, when the starting compound used is such compound having 3"-amino group and 4"-hydroxyl group in the cis-configuration, like gentamicins, these amino group and hydroxyl group can be protected by converting them into the form of a cyclic carbamate by a known procedure. The 5-hydroxyl group of the starting compound of the general formula (A) can receive the steric hindrance owing to the existence of the aminoglycosyl group at the 4-position or of the two aminoglycosyl groups at the 4- and 6-positions. Therefore, when the starting compound of the formula (A) is subjected to the hydroxyl-protecting reaction, the 5-hydroxyl group is relatively not likely to be acetylated or benzoylated, so that there can be obtained in a relatively high yield such an N,O-protected 2-deoxystreptamine derivative having the free 5-hydroxyl group and represented by the general formula

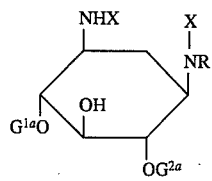

(B)

wherein X is a known amino-protecting group such as an acyl group, an alkoxycarbonyl group, benzyloxycarbonyl group or a sulfonyl group; $G^{1a}$ denotes an N,O-protected aminoglycosyl group as derived by protecting all of the amino groups and hydroxyl groups of the aminoglycosyl group ($G^1$) of the formula (i) or of the 4'-eno-aminoglycosyl group ($G^1$) of the formula (ii) shown in the above-mentioned general formula (A); and $G^{2a}$ denotes an N,O-protected aminoglycosyl group as derived by protecting all of the amino groups and hydroxyl groups of the 3"-amino-3"-deoxyglycosyl group ($G^2$) of the formula (iii) or of the 2"-amino-2"-deoxyglycosyl group ($G^2$) of the formula (iv) shown in the above-mentioned general formula (A), as will be referred to repeatedly and similarly hereinafter.

The so prepared compound having the free 5-hydroxyl group and represented by the general formula (B) above is then oxidized to produce the corresponding 5-keto derivative of the formula (C) shown below.

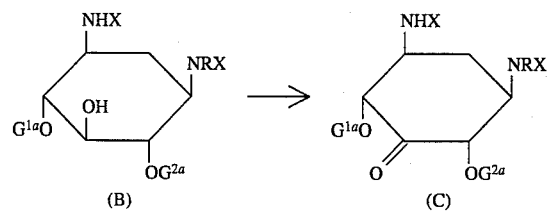

When the above-mentioned oxidation is effected by reacting the compound of the formula (B) with a known oxidizing agent such as pyridinium chlorochromate (PCC) or a mixture of dimethylsulfoxide (DMSO) and acetic anhydride, the 5-hydroxyl group of the compound (B) is oxidized to produce the 5-keto derivative of the formula (C). This oxidation reaction may suitably be conducted by using dichloromethane, dimethylsulfoxide (DMSO), pyridine, a mixture of pyridine-DMSO, benzene, carbon tetrachloride, chloroform, acetonitrile and the like as the solvent. The reaction temperature for this oxidation may suitably be in a range of −20° C. to 100° C. The oxidation reaction can be finished in one week. The 5-keto derivative of the formula (C) is then reacted with a fluorinating agent such as DAST as a typical example, in an organic solvent such as dichloromethane, benzene, dichloromethane-pyridine, carbon tetrachloride, chloroform, acetonitrile and the like at a temperature of 0° to 100° C., with the fluorinating agent being used in a proportion of 5 to 20 moles per mole of the 5-keto derivative. Thereby, the 2,5-dideoxy-5,5-difluorostreptamine derivative of the formula

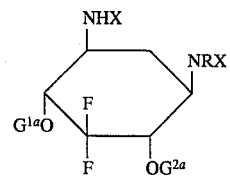

(D)

wherein X, $G^{1a}$ and $G^{2a}$ have the same meanings as defined above is produced and obtained in a relatively high yield. Although it is generally known that DAST is reacted with a keto group present in an organic compound to introduce difluoro groups into the organic compound, it is achieved firstly up to dates by the present inventors that a keto derivative is prepared from the aminoglycosidic antibiotics and then reacted with DAST with getting a success in synthetizing the 5-deoxy-5,5-difluoro derivatives of the aminoglycosides.

From the 2,5-dideoxy-5,5-difluorostreptamine derivative of the formula (D) are then removed the amino-protecting groups and the hydroxyl-protecting groups by known methods (for example, by de-acylation with alkaline treatment, de-alkoxycarbonylation, de-benzyloxycarbonylation through catalytic reduction, or de-N-tosylation by treatment with sodium in liquefied ammonia, etc.), whereby there can be obtained the desired 2,5-dideoxy-5,5-difluorostreptmine derivative of the formula

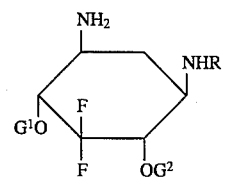

(I¹)

wherein R, $G^1$ and $G^2$ have the same meanings as defined in the above general formula (A). From amongst the 4-O-

(aminoglycosyl)- or 4,6-di-O-(aminoglycosyl)-2,5-dideoxy-5,5-difluorostreptamines of the formula (I$^1$) above, is taken such a compound of the formula

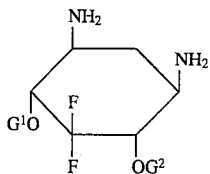 (I$^2$)

wherein G$^1$ and G$^2$ have the same meanings as defined in the above general formula (A), as a compound having unsubstituted 1-amino group, namely such compound where R is a hydrogen atom. The compound of the formula (I$^2$) is then treated by the selectively amino-protecting method disclosed in the specification of U.S. Pat. No. 4,297,485, so that all or some of the amino groups of the compound of the formula (I$^2$) are protected with appropriate amino-protecting groups, and thereby it is feasible to prepare a 1-N-unprotected-poly-N-protected-4-O-(aminoglycosyl)- or 4,6-di-O-(aminoglycosyl)-2,5-dideoxy-5,5-difluorostreptamine represented by the formula

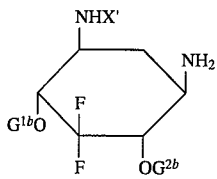 (I$^3$)

wherein X' is appropriate amino-protecting group; and G$^{1b}$ denotes an N-protected aminoglycosyl group as derived by protecting with the amino-protecting group (X') all or some of the amino groups of the aminoglycosyl group (G$^1$) of the formula (i) or of the 4'-eno-aminoglycosyl group (G$^1$) of the formula (ii) shown in the above-mentioned general formula (A); and G$^{2b}$ denotes an N-protected aminoglycosyl group as derived by protecting with appropriate amino-protecting group all or some of the amino groups of the 3"-amino-3"-deoxyglycosyl group (G$^2$) of the formula (iii) or of the 2"-amino-2"-deoxyglycosyl group (G$^2$) of the formula (iv) shown in the above-mentioned general formula (A).

When the 1-amino group of the compound of the formula (I$^3$) is either alkylated by reacting with an alkyl bromide or iodide of the formula

 R$^1$—Hal (X)

where R$^1$ is an alkyl group of 1 to 4 carbon atoms and Hal denotes bromine or iodine, or acylated by reaction with an α-hydroxy-ω-aminoalkanoic acid of the formula

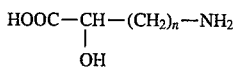 (IX)

where n is an integer of 1 to 3, for example, 3-amino-2-(RS)-hydroxypropionic acid or 4-amino-2-(S)-hydroxybutyric acid, or with its protected derivative having the amino group protected with an amino-protective group or its activated derivative, there can be produced a 1-N-modified derivative having the formula

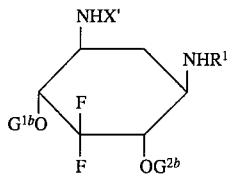 (I$^4$)

wherein X', G$^{1b}$ and G$^{2b}$ have the same meanings as defined above and R$^1$ is an alkyl group of 1 to 4 carbon atoms or an α-hydroxy-ω-aminoalkanoyl group of the formula

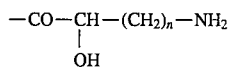

where n is an integer of 1 to 3.

By removing the amino-protecting groups from the compound of the formula (I$^4$) by conventional methods, a 1-N-alkyl- or 1-N-(α-hydroxy-ω-aminoalkanoyl)-4-O-(aminoglycosyl)- or -4,6-di-O-(aminoglycosyl)-2,5-dideoxy-5,5-difluorostreptamine having the formula

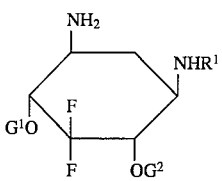 (I$^5$)

wherein R$^1$, G$^1$ and G$^2$ have the same meanings as defined above can be produced.

The compound represented by the formula (I$^1$) above, as well as the compound represented by the formula (I$^5$) are included by the new 5-deoxy-5,5-difluoro derivatives of the aminoglycosidic antibiotics as desired and provided in accordance with this invention.

According to the first aspect of this invention, therefore, there is provided a 4-O-(aminoglycosyl)- or 4,6di-O-(aminoglycosyl)-2,5-dideoxy-5,5-difluorostreptamine derivative represented by the general formula

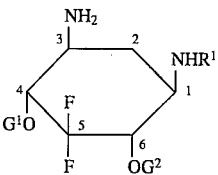 (I)

wherein R$^1$ is a hydrogen atom, an alkyl group of 1–4 carbon atoms or an α-hydroxy-ω-aminoalkanoyl group of the formula

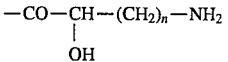

where n is an integer of 1 to 3, G$^1$ is either an aminoglycosyl group of the formula

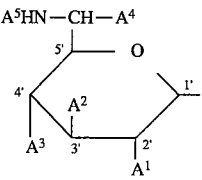 (i)

Where A$^1$ is a hydroxyl group or amino group, A$^2$ and A$^3$ are independently a hydrogen atom, hydroxyl group or fluoro group, A$^4$ is a hydrogen atom or methyl group, and A$^5$ is a hydrogen atom or methyl group, or a 4'-eno-aminoglycosyl group of the formula

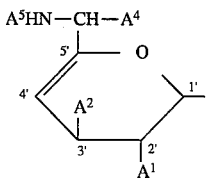

where $A^1$, $A^2$, $A^4$ and $A^5$ independently have the same meanings as defined above, and $G^2$ is either a hydrogen atom, or a 3"-amino-3"-deoxyglycosyl group of the formula

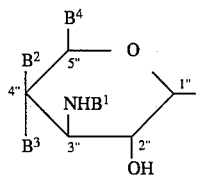

where $B^1$ is a hydrogen atom or methyl group, $B^2$ and $B^3$ are independently a hydrogen atom, hydroxyl group or methyl group, and $B^4$ is a hydrogen atom or a hydroxymethyl group (—$CH_2OH$), or a 2"-amino-2"-deoxyglycosyl group of the formula

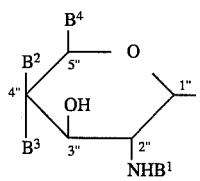

where $B^1$, $B^2$, $B^3$ and $B^4$ independently have the same meanings as defined above, and a pharmaceutically acceptable acid addition salt of said derivative.

The new compound of the general formula (I) according to this invention is usually obtained in the form of a free base, a hydrate or a carbonate thereof. The new compound of the formula (I) may, if desired, be converted into a pharmaceutically acceptable acid addition salt thereof in a known manner. Such acid addition salts of said compound include such salt with a pharmaceutically acceptable inorganic acid such as hydrochloric acid, sulfuric acid, phosphoric acid, nitric acid and the like; or with a pharmaceutically acceptable organic acid such as acetic acid, malic acid, citric acid, ascorbic acid, methanesulfonic acid and the like.

A compound of the general formula (I) according to this invention or an acid addition salt thereof may be mixed with a pharmaceutically acceptable liquid or solid carrier or vehicle to prepare an antibacterial composition.

The 2,5-dideoxy-5,5-difluorostreptamine derivative of the general formula (I) according to this invention may include a streptamine derivative which is a 4,6-di-O-(aminoglycosyl)-2,5-dideoxy-5,5-difluorostreptamine derivative represented by the general formula

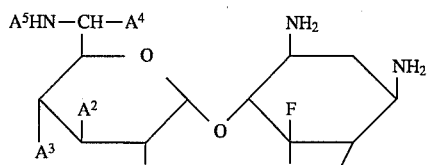

wherein $A^1$, $A^2$, $A^3$, $A^4$ and $A^5$, as well as $B^1$, $B^2$, $B^3$ and $B^4$ have the same meanings as defined for the general formula (I) described above, and which is such a compound belonging to a derivative of kanamycin A, a derivative of kanamycin B, a derivative of gentamicin $C_1$, a derivative of gentamicin $C_{1a}$ or a derivative of gentamicin $C_2$ or a derivative of sagamicin.

The streptamine derivative of the general formula (Ia) above may largely be classified as its preferred embodiments into the compounds of three classes which are respectively represented by the following formula (Ia-1), formula (Ia-2) and formula (Ia-3):

(1) A streptamine derivative which is a compound represented by the general formula

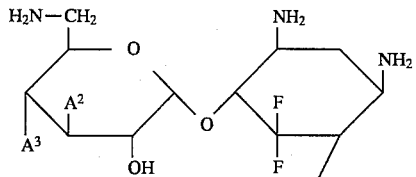

wherein (i) $A^2$ and $A^3$ are each a hydroxyl group, or (ii) $A^2$ is a hydrogen atom and $A^3$ is a hydroxyl group, or (iii) $A^2$ and $A^3$ are each a hydrogen atom, and which is namely (i) 5-deoxy-5,5-difluorokanamycin A, or (ii) 5,3'-dideoxy-5,5-difluorokanamycin A, or (iii) 5,3',4'-trideoxy-5,5-difluorokanamycin A.

(2) A streptamine derivative which is a compound represented by the general formula

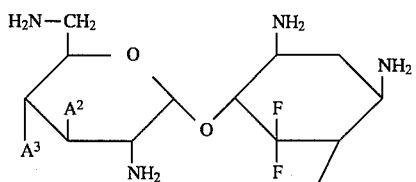

wherein (i) $A^2$ and $A^3$ are each a hydroxyl group, or (ii) $A^2$ is a hydrogen atom and $A^3$ is a hydroxyl group, or (iii) $A^2$ and $A^3$ are each a hydrogen atom, or (iv) $A^2$ is a fluoro group and $A^3$ is a hydroxyl group, or (v) $A^2$ is a fluoro group and $A^3$ is a hydrogen atom, and which is namely (i) -deoxy-5,5-difluorokanamycin B, or (ii) 5,3'-dideoxy-5,5 -difluorokanamycin B, or (iii) 5,3',4'-trideoxy-5,5-difluorokanamycin B, or (iv) 5,3'-dideoxy-5,5,3'-trifluorokanamycin B, or (v) 5,3',4'-trideoxy-5,5,3'-trifluorokanamycin B.

(3) A streptamine derivative which is a compound represented by the general formula

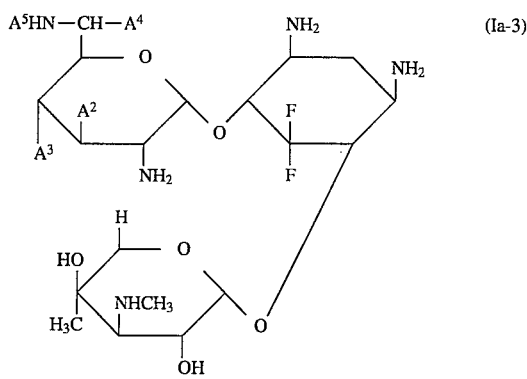
(Ia-3)

wherein (i) $A^2$ and $A^3$ are each a hydrogen atom and $A^4$ and $A^5$ are each a methyl group, or (ii) $A^2$, $A^3$, $A^4$ and $A^5$ are all and each a hydrogen atom, or (iii) $A^2$, $A^3$ and $A^5$ are all and each a hydrogen atom and $A^4$ is methyl group, or (iv) $A^2$, $A^3$ and $A^4$ are all and each a hydrogen atom and $A^5$ is methyl group, and which is namely (i) 5-deoxy-5,5-difluorogentamicin $C_1$, or (ii) 5-deoxy-5,5-difluorogentamicin $C_{1a}$, or (iii) 5-deoxy-5,5-difluorogentamicin $C_2$, or (iv) 5-deoxy-5,5-difluorosagamicin.

Further, the 2,5-dideoxy-5,5-difluorostreptamine derivative of the general formula (I) according to this invention may include a streptamine derivative which is a compound represented by the general formula

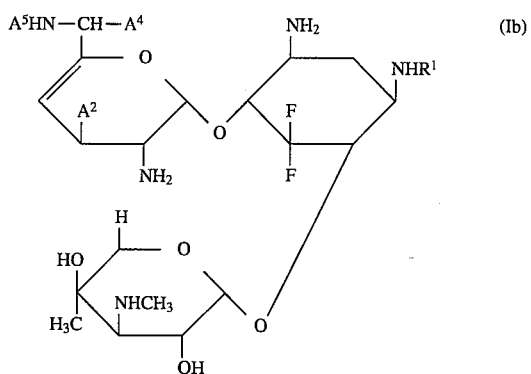
(Ib)

wherein (i) $R^1$ is a hydrogen atom and $A^2$, $A^4$ and $A^5$ are all and each a hydrogen atom, or (ii) $R^1$ is ethyl group and $A^2$, $A^4$ and $A^5$ are all and each a hydrogen atom, and which is namely (i) 5-deoxy-5,5-difluorosisomicin or (ii) 5-deoxy-5,5-difluoronetilmicin.

Furthermore, the 2,5-dideoxy-5,5-difluorostreptamine derivative of the general formula (I) according to this invention may include a streptamine derivative which is a 1-N-(α-hydroxy-ω-aminoalkanoyl)-4,6-di-O-(aminoglycosyl)-2,5-dideoxy-5,5-difluorostreptamine derivative represented by the general formula

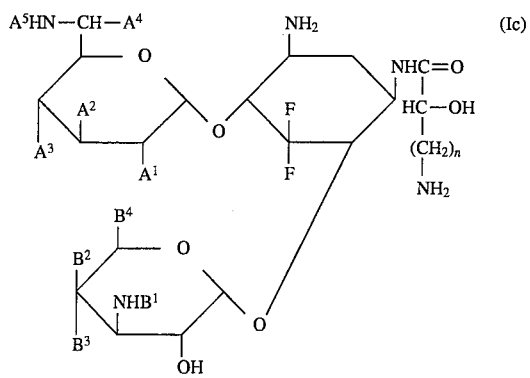
(Ic)

wherein n is an integer of 1 to 3, and $A^1$, $A^2$, $A^3$, $A^4$ and $A^5$ as well as $B^1$, $B^2$, $B^3$ and $B^4$ respectively have the same meanings as defined for the general formula (I) described above or for the general formula (Ia) described above.

The streptamine derivative of the general formula (Ic) above may largely be classified as its preferred embodiments into the compounds of three classes which are respectively represented by the following formula (Ic-1), formula (Ic-2) and formula (Ic-3):

(1) A streptamine derivative which is a compound represented by the general formula

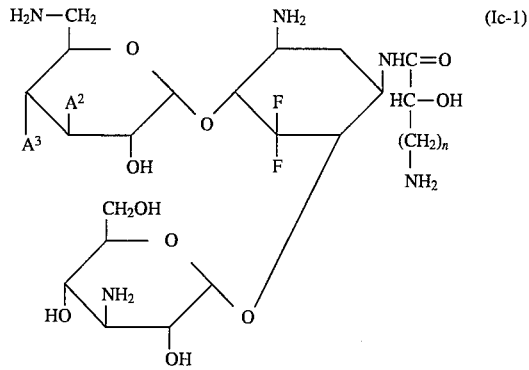
(Ic-1)

wherein n is an integer of 1 to 3, and (i) $A^2$ and $A^3$ are each a hydroxyl group, or (ii) $A^2$ is a hydrogen atom and $A^3$ is hydroxyl group, or (iii) $A^2$ and $A^3$ are each a hydrogen atom, and which is namely a 1-N-(α-hydroxy-ω-aminoalkanoyl) derivative of anyone of (i) 5-deoxy-5,5-difluorokanamycin A or (ii) 5,3'-dideoxy-5,5-difluorokanamycin A or (iii) 5,3',4'-trideoxy-5,5-difluorokanamycin A.

(2) A streptamine derivative which is a compound represented by the general formula

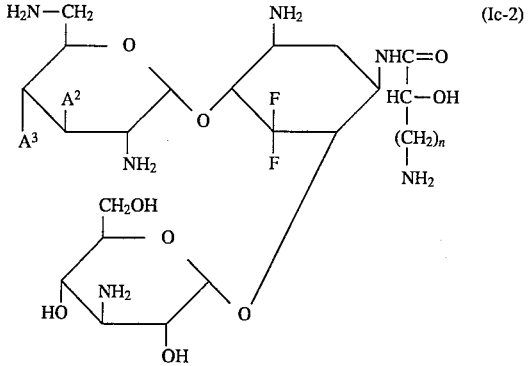
(Ic-2)

wherein n is an integer of 1 to 3, and (i) $A^2$ and $A^3$ are each a hydroxyl group, or (ii) $A^2$ is a hydrogen atom and $A^3$ is hydroxyl group, or (iii) $A^2$ and $A^3$ are each a hydrogen atom, or (iv) $A^2$ is a fluoro group and $A^3$ is hydroxyl group, or (v) $A^2$ is a fluoro group and $A^3$ is a hydrogen atom, and which is namely a 1-N-(α-hydroxy-ω-aminoalkanoyl) derivative of anyone of (i) 5-deoxy-5,5-difluorokanamycin B or (ii) 5,3'-dideoxy-5,5-difluorokanamycin B or (iii) 5,3',4'-trideoxy-5,5-difluorokanamycin B or (iv) 5,3'-dideoxy-5,5,3'-trifluorokanamycin B or (v) 5,3',4'-trideoxy-5,5,3'-trifluorokanamycin B.

(3) A streptamine derivative which is a compound represented by the general formula

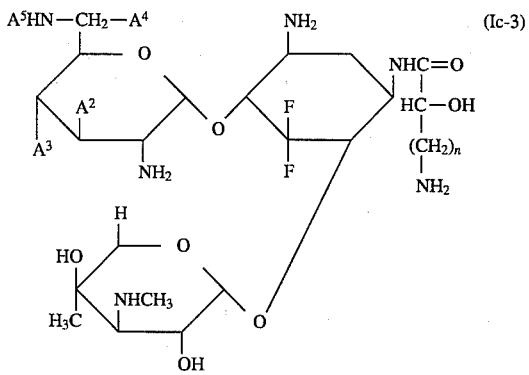

wherein n is an integer of 1 to 3, and (i) $A^2$ and $A^3$ are each a hydrogen atom and $A^4$ and $A^5$ are each a methyl group, or (ii) $A^2$, $A^3$, $A^4$ and $A^5$ are all and each a hydrogen atom, or (iii) $A^2$, $A^3$ and $A^5$ are all and each a hydrogen atom and $A^4$ is methyl group, or (iv) $A^2$, $A^3$ and $A^4$ are all and each a hydrogen atom and $A^5$ is methyl group, and which is a 1-N-(α-hydroxy-ω-aminoalkanoyl) derivative of anyone of (i) 5-deoxy-5,5-difluorogentamicin $C_1$ or (ii) 5-deoxy-5,5-difluorogentamicin $C_{1a}$ or (iii) 5-deoxy-5,5-difluorogentamicin $C_2$ or (iv) 5-deoxy-5,5-difluorosagamicin.

Moreover, the 2,5-dideoxy-5,5-difluorostreptamine derivative of the general formula (I) according to this invention may include a streptamine derivative which is 5-deoxy-5,5-difluoroseldomycin factor 3 represented by the formula

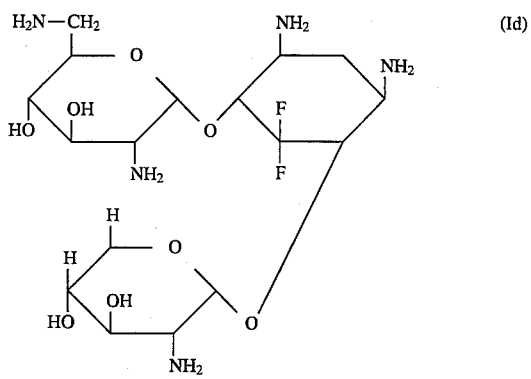

Next, according to the second aspect of this invention, there is provided an antibacterial composition, characterized in that said composition comprises a 4-O-(aminoglycosyl)- or 4,6-di-O-(aminoglycosyl)-2,5-dideoxy-5,5-difluorostreptamine derivative represented by the general formula

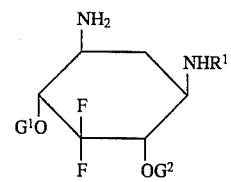

wherein $R^1$, $G^1$ and $G^2$ respectively have the same meanings as defined for the general formula (I) shown hereinbefore, as the active ingredient, in association with a pharmaceutically acceptable carrier for the active ingredient.

The antibacterial activity of the compounds of the general formula (I) according to this invention has been examined by determining their minimum inhibitory concentrations (MIC, mcg/ml) against the growth of various kinds of bacteria by a standard serial dilution method (on Mueller-Hinton agar medium incubated at 37° C).

Among the compounds of the general formula (I) according to this invention, such representative compounds of which the MIC has been determined are listed below. All of these compounds are in the form of basic and colorless and powdery substance having no definite melting point.

(1) 5-deoxy-5,5,-difluorokanamycin A (abbreviated as 5FF-KMA).

(2) 1-N-[4-amino-2-(S)-hydroxybutyryl]-5-deoxy-5,5-difluorokanamycin A, namely 5-deoxy-5,5-difluoroamikacin (abbreviated as 5FF-amikacin).

(3) 5-deoxy-5,5-difluorokanamycin B (abbreviated as 5FF-KMB).

(4) 5,3'-dideoxy-5,5-difluorokanamycin B, namely 5-deoxy-5,5-difluorotobramycin (abbreviated as 5FF-TOB).

(5) 1-N-[4-amino-2-(S)-hydroxybutyryl]-5-deoxy-5,5-difluorotobramycin (abbreviated as 5FF-TOB-AHB).

(6) 5,3',4'-trideoxy-5,5-difluorokanamycin B, namely 5-deoxy-5,5-difluorodibekacin (abbreviated as 5FF-DKB).

(7) 1-N-[4-amino-2-(S)-hydroxybutyryl]-5,3',4'-trideoxy-5,5-difluorokanamycin B (abbreviated as 5FF-DKB-AHB).

(8) 5-deoxy-5,5-difluorogentamicin $C_1$ (abbreviated as 5FF-genta-$C_1$).

(9) 1-N-[4-amino-2-(S)-hydroxybutyryl]-5-deoxy-5,5-difluorogentamicin $C_1$ (abbreviated as 5FF-genta-$C_1$-AHB).

(10) 5-deoxy-5,5-difluorogentamicin $C_2$ (abbreviated as 5FF-genta-$C_2$).

(11) 1-N-[4-amino-2-(S)-hydroxybutyryl]-5-deoxy-5,5-difluorogentamicin $C_2$ (abbreviated as 5FF-genta-$C_2$-AHB).

(12) 5-deoxy-5,5-difluorogentamicin $C_{1a}$ (abbreviated as 5FF-genta-$C_{1a}$).

(13) 5-deoxy-5,5-difluoronetilmicin (abbreviated as 5FF-netilmicin).

The antibacterial spectra (MIC values, mcg/ml) so determined of the above-mentioned respective compounds are shown in Table 1-a to Table 1-c below. For comparison, the antibacterial spectra (MIC values, mcg/ml) similarly determined of kanamycin A (abbreviated as KMA), kanamycin B (abbreviated as KMB), amikacin, 3'-deoxykanamycin B, namely tobramycin (abbreviated as TOB), 5,3'-dideoxy-5-fluorokanamycin B (abbreviated as 5F-TOB), 1-N-[4-amino-2-(S)-hydroxybutyryl]-5,3'-dideoxy-5-fluorokanamycin B (abbreviated as 5F-TOB-AHB), 3',4'-dideoxykanamycin B (abbreviated as DKB), 5,3',4'-trideoxy-5-fluorokanamycin B (abbreviated as 5F-DKB), 1-N-[4-amino-2-(S)-hydroxybutyryl]-5,3',4'-trideoxy-5-fluorokanamycin B (abbreviated as 5F-DKB-AHB), gentamicin $C_1$ (abbreviated as genta-$C_1$), gentamicin $C_2$ (abbreviated as genta-$C_2$) and gentamicin $C_{1a}$ (abbreviated as genta-$C_{1a}$) are also shown in Table 1-a to Table 1-c below.

TABLE 1-a

| Tested Microorganisms | Resistance mechanism | MIC. (mcg/ml) | |
|---|---|---|---|
| | | KMA (Comparative) | 5FF-KMA (Invention) |
| *Staphylococcus aureus* 209P | | 1.56 | 3.12 |
| *Staphylococcus aureus* Ap01 | ANT(4') | 25 | 50 |
| *Bacillus subtilis* PCI219 | | 0.78 | 0.78 |
| *Corynebacterium bovis* 1810 | | 12.5 | 12.5 |
| *Escherichia coli* K-12 | | 0.78 | 0.78 |
| *Escherichia coli* K-12 R5 | AAC(6') | >100 | >100 |
| *Escherichia coli* K-12 ML 1629 | APH(3')-I | >100 | >100 |
| *Escherichia coli* K-12 LA 290 R55 | ANT(2") | 50 | 12.5 |
| *Escherichia coli* JR225 | AAC(3) | 3.12 | 1.56 |
| *Escherichia coli* JR66/W677 | { APH(3')-II  ANT(2") } | >100 | |
| Mycobacterium 607 | | 6.25 | 3.12 |
| *Klebsiella pneumoniae* 22#3038 | { APH(3')-II  ANT(2") } | >100 | |
| *Proteus rettgeri* GN 311 | | 0.78 | 1.56 |
| *Serratia marcescens* | | 12.5 | 12.5 |
| Providencia sp. Pv 16 | AAC(2') | 3.12 | 12.5 |
| *Pseudomonas aeruginosa* A3 | | 6.25 | 6.25 |
| *Pseudomonas aeruginosa* GN 315 | AAC(6') | >100 | >100 |

| Tested Microorganisms | Resistance mechanism | MIC. (mcg/ml) | | | |
|---|---|---|---|---|---|
| | | Amikacin (Comparative) | 5FF-amikacin (invention) | KMB (Comparative) | 5FF-KMB (Invention) |
| *Staphylococcus aureus* 209P | | 0.78 | 3.12 | 0.39 | 0.78 |
| *Staphylococcus aureus* Ap01 | ANT(4') | >100 | >100 | 25 | 50 |
| *Bacillus subtilis* PCI219 | | 0.39 | 1.56 | <0.2 | 0.39 |
| *Corynebacterium bovis* 1810 | | 1.56 | 3.12 | 0.78 | 1.56 |
| *Escherichia coli* K-12 | | 0.78 | 1.56 | 0.39 | 0.39 |
| *Escherichia coli* K-12 R5 | AAC(6') | 100 | 25 | 50 | 100 |
| *Escherichia coli* K-12 ML 1629 | APH(3')-I | 1.56 | 3.12 | >100 | >100 |
| *Escherichia coli* K-12 LA 290 R55 | ANT(2") | 1.56 | 3.12 | 12.5 | 3.12 |
| *Escherichia coli* JR225 | AAC(3) | 0.78 | 0.39 | 12.5 | 3.12 |
| *Escherichia coli* JR66/W677 | { APH(3')-II  ANT(2") } | 3.12 | 3.12 | >100 | |
| Mycobacterium 607 | | 0.78 | 3.12 | 1.56 | 1.56 |
| *Klebsiella pneumoniae* 22#3038 | { APH(3')-II  ANT(2") } | 3.12 | 6.25 | >100 | |
| *Proteus rettgeri* GN 311 | | 1.56 | 1.56 | 0.2 | 0.39 |
| *Serratia marcescens* | | 3.12 | 6.25 | 3.12 | 6.25 |
| Providencia sp. Pv 16 | AAC(2') | 1.56 | 3.12 | 12.5 | 12.5 |
| *Pseudomonas aeruginosa* A3 | | 0.78 | 3.12 | 1.56 | 3.12 |
| *Pseudomonas aeruginosa* GN 315 | AAC(6') | 50 | >100 | 50 | >100 |

TABLE 1-b

| Tested Microorganisms | Resistance mechanism | MIC. (mcg/ml) | | | | |
|---|---|---|---|---|---|---|
| | | TOB (Comparative) | 5F-TOB (Comparative) | 5FF-TOB (Invention) | 5F-TOB-AHB (Comparative) | 5FF-TOB-AHB (Invention) |
| *Staphylococcus aureus* 209P | | <0.2 | 0.39 | 0.39 | 0.39 | 0.39 |
| *Staphylococcus aureus* Ap01 | ANT(4') | 12.5 | 0.39 | 25 | 3.12 | 3.12 |
| *Bacillus subtilis* PCI219 | | <0.2 | <0.2 | 0.39 | <0.2 | <0.2 |
| *Corynebacterium bovis* 1810 | | 1.56 | 1.56 | 1.56 | <0.2 | <0.2 |
| *Escherichia coli* K-12 | | 0.39 | <0.2 | 0.39 | <0.2 | <0.2 |
| *Escherichia coli* K-12 R5 | AAC(6') | 25 | 25 | 25 | 3.12 | 3.12 |
| *Escherichia coli* K-12 ML 1629 | APH(3')-I | 0.78 | 0.78 | 0.78 | 0.39 | 0.39 |
| *Escherichia coli* K-12 LA 290 R55 | ANT(2") | 12.5 | 3.12 | 0.78 | 0.39 | <0.2 |
| *Escherichia coli* JR225 | AAC(3) | 25 | 0.78 | 0.39 | <0.2 | <0.2 |
| *Escherichia coli* JR66/W677 | { APH(3')-II | 12.5 | 0.78 | 1.56 | 0.78 | 0.39 |

TABLE 1-b-continued

| Tested Microorganisms | Resistance mechanism | | | | | |
|---|---|---|---|---|---|---|
| Mycobacterium 607 | ANT(2") | 0.39 | 0.78 | 0.39 | 0.39 | 0.39 |
| Klebsiella pneumoniae 22#3038 | APH(3')-II / ANT(2") | 12.5 | 3.12 | 0.78 | 0.78 | 0.78 |
| Proteus rettgeri GN 311 | | 0.39 | <0.2 | <0.2 | <0.2 | 0.39 |
| Serratia marcescens | | 3.12 | 6.25 | 3.12 | 3.12 | 1.56 |
| Providencia sp. Pv 16 | AAC(2') | 6.25 | 3.12 | 12.5 | 0.39 | 0.78 |
| Pseudomonas aeruginosa A3 | | <0.2 | <0.2 | <0.2 | <0.2 | 0.78 |
| Pseudomonas aeruginosa GN 315 | AAC(6') | 25 | 50 | 100 | 1.56 | 6.25 |

| | | MIC. (mcg/ml) | | | | |
|---|---|---|---|---|---|---|
| Tested Microorganisms | Resistance mechanism | DKB (Comparative) | 5F-DKB (Comparative) | 5FF-DKB (Invention) | 5F-DKB-AHB (Comparative) | 5FF-DKB-AHB (Invention) |
| Staphylococcus aureus 209P | | 0.39 | 0.78 | 0.78 | 0.39 | 0.39 |
| Staphylococcus aureus Ap01 | ANT(4') | 0.78 | 3.12 | 3.12 | 1.56 | 3.12 |
| Bacillus subtilis PCI219 | | <0.2 | 0.78 | 0.39 | <0.2 | 0.39 |
| Corynebacterium bovis 1810 | | 6.25 | 6.25 | 1.56 | <0.2 | <0.2 |
| Escherichia coli K-12 | | 0.39 | 3.12 | 0.39 | <0.2 | <0.2 |
| Escherichia coli K-12 R5 | AAC(6') | 50 | 100 | 100 | 12.5 | 3.12 |
| Escherichia coli K-12 ML 1629 | APH(3')-I | 0.78 | 3.12 | 0.78 | 0.39 | 0.39 |
| Escherichia coli K-12 LA 290 R55 | ANT(2") | 50 | 6.25 | 1.56 | 0.39 | <0.2 |
| Escherichia coli JR225 | AAC(3) | 100 | 3.12 | 3.12 | <0.2 | <0.2 |
| Escherichia coli JR66/W677 | APH(3')-II / ANT(2") | 25 | 3.12 | 1.56 | 0.78 | 0.39 |
| Mycobacterium 607 | | 1.56 | 6.25 | 1.56 | 0.78 | 0.78 |
| Klebsiella pneumoniae 22#3038 | APH(3')-II / ANT(2") | 50 | 6.25 | 1.56 | 0.78 | 0.78 |
| Proteus rettgeri GN 311 | | <0.2 | 0.78 | 0.39 | <0.2 | 0.39 |
| Serratia marcescens | | 25 | 12.5 | 12.5 | 3.12 | 1.56 |
| Providencia sp. Pv 16 | AAC(2') | 25 | 12.5 | 12.5 | 0.39 | 0.78 |
| Pseudomonas aeruginosa A3 | | 0.2 | 0.39 | 0.39 | 0.39 | 0.78 |
| Pseudomonas aeruginosa GN 315 | AAC(6') | 100 | 100 | >100 | 6.25 | 12.5 |

TABLE 1-c

| | | MIC. (mcg/ml) | | | | |
|---|---|---|---|---|---|---|
| Tested Microorganisms | Resistance mechanism | Genta-$C_1$ (Comparative) | 5FF-Genta-$C_1$ (Invention) | 5FF-Genta-$C_1$-AHB (Invention) | Genta-$C_2$ (Comparative) | 5FF-Genta-$C_2$ (Invention) |
| Staphylococcus aureus 209P | | <0.2 | 1.56 | 1.56 | <0.2 | 0.78 |
| Staphylococcus aureus Ap01 | ANT(4') | 0.78 | 12.5 | 25 | 0.78 | 6.25 |
| Bacillus subtilis PCI219 | | <0.2 | 1.56 | 1.56 | <0.2 | 0.2 |
| Corynebacterium bovis 1810 | | 0.39 | 3.12 | 0.78 | 0.39 | 0.78 |
| Escherichia coli K-12 | | 0.2 | 1.56 | <0.2 | <0.2 | 0.78 |
| Escherichia coli K-12 R5 | AAC(6') | 0.78 | 1.56 | 0.78 | 1.56 | 1.56 |
| Escherichia coli K-12 ML 1629 | APH(3')-I | 0.39 | 1.56 | 1.56 | 0.39 | 0.78 |
| Escherichia coli K-12 LA 290 R55 | ANT(2") | 12.5 | 0.78 | 0.39 | 12.5 | 3.12 |
| Escherichia coli JR225 | AAC(3) | 25 | 12.5 | <0.2 | 6.25 | 6.25 |
| Escherichia coli JR66/W677 | APH(3')-II / ANT(2") | 12.5 | 0.78 | 3.12 | 25 | 3.12 |
| Mycobacterium 607 | | 3.12 | 1.56 | 3.12 | 1.56 | 0.78 |
| Klebsiella pneumoniae 22#3038 | APH(3')-II / ANT(2") | 12.5 | 3.12 | 1.56 | 12.5 | 1.56 |
| Porteus rettgeri GN 311 | | 0.78 | 1.56 | 1.56 | 0.2 | 0.78 |
| Serratia marcescens | | 0.78 | 1.56 | 3.12 | 0.78 | 0.78 |
| Providencia sp. Pv 16 | AAC(2') | 25 | 25 | 6.25 | 6.25 | 6.25 |
| Pseudomonas aeruginosa A3 | | 0.78 | 6.25 | 6.25 | 0.39 | 1.56 |
| Pseudomonas aeruginosa GN 315 | AAC(6') | 6.25 | 25 | 100 | 3.12 | 25 |

| | | MIC. (mcg/ml) | | | |
|---|---|---|---|---|---|
| Tested Microorganisms | Resistance mechanism | 5FF-Genta-$C_2$-AHB (Invention) | Genta-$C_{1a}$ (Comparative) | 5FF-Genta-$C_{1a}$ (Invention) | 5FF-Netilmicin (Invention) | Netilmicin (Comparative) |
| Staphylococcus aureus 209P | | 0.78 | <0.2 | 0.78 | 3.12 | <0.2 |
| Staphylococcus aureus Ap01 | ANT(4') | 12.5 | 0.39 | 3.12 | 12.5 | 0.78 |
| Bacillus subtilis PCI219 | | 0.2 | <0.2 | 0.39 | 0.39 | <0.2 |

TABLE 1-c-continued

| | | | | | | |
|---|---|---|---|---|---|---|
| Corynebacterium bovis 1810 | | 0.2 | <0.2 | 0.78 | 1.56 | 1.56 |
| Escherichia coli K-12 | | <0.2 | <0.2 | <0.2 | <0.2 | <0.2 |
| Escherichia coli K-12 R5 | AAC(6') | 3.12 | 3.12 | 12.5 | 50 | 50 |
| Escherichia coli K-12 ML 1629 | APH(3')-I | 0.39 | 0.39 | 0.39 | 0.78 | 0.39 |
| Escherichia coli K-12 LA 290 R55 | ANT(2") | 0.2 | >100 | 3.12 | 0.39 | 0.39 |
| Escherichia coli JR225 | AAC(3) | <0.2 | 25 | 3.12 | 1.56 | 12.5 |
| Escherichia coli JR66/W677 | { APH(3')-II ANT(2") } | 0.78 | 12.5 | 1.56 | 0.78 | 0.39 |
| Mycobacterium 607 | | 3.12 | 6.25 | 0.78 | 1.56 | 1.56 |
| Klebsiella pneumoniae 22#3038 | { APH(3')-II ANT(2") } | 1.56 | 12.5 | 1.56 | 1.56 | 0.39 |
| Proteus rettgeri GN 311 | | 0.78 | <0.2 | 0.39 | 1.56 | 0.39 |
| Serratia marcescens | | 3.12 | 1.56 | 6.25 | 6.25 | 6.25 |
| Providencia sp. Pv 16 | AAC(2') | 6.25 | 12.5 | 12.5 | 12.5 | 6.25 |
| Pseudomonas aeruginosa A3 | | 3.12 | <0.2 | 0.78 | 1.56 | 0.39 |
| Pseudomonas aeruginosa GN 315 | AAC(6') | 100 | 12.5 | 100 | >100 | >100 |

As will be clear from the antibacterial data of Table 1, the compound of the general formula (I) according to this invention can exhibit its high antibacterial activity against many species of bacteria and has broad antibacterial spectra.

Further, in order to estimate acute toxicity of the compound of the general formula (I) according to this invention, some examples of the compounds of this invention were independently dissolved in water to prepare aqueous solutions (as adjusted to pH 7 by addition of hydrochloric acid). Each of these aqueous solutions was intravenously injected to mice of dd-strain (male, 4 week-aged, four mice per group) and then 50% lethal dosage ($LD_{50}$) (mg/kg) of the tested compound was evaluated. The tested compounds of this invention are expressed by the same abbreviations as in Table 1. The acute toxicity of some examples of the known, comparative compounds was evaluated by a similar tests. The comparative compounds as tested are also expressed by the same abbreviations as in Table 1. While, "HBK" denotes 1-N-[4-amino-(S)-2-hydroxybutyryl]-3',4'-dideoxykanamycin B. 5FF-netilmicin denotes 5-deoxy-5,5-difluoronetilmicin according to this invention.

The results of the above tests for estimation of the acute toxicity of the compounds are summarized in Table 2 below.

TABLE 2

| Tested compounds | | $LD_{50}$ (mg/kg) |
|---|---|---|
| 5FF-KMA | (this Invention) | >300 |
| 5FF-amikacin | (this Invention) | >300 |
| Amikacin | (comparative) | >300 |
| 5FF-KMB | (this Invention) | — |
| DKB | (comparative) | ca.90 |
| 5F-DKB | (comparative) | ca.135 |
| HBK | (comparative) | 70 |
| 5FF-DKB | (this Invention) | 250 |
| 5FF-DKB-AHB | (this Invention) | ca.200 |
| TOB | (comparative) | ca.80 |
| 5F-TOB | (comparative) | ca.180 |
| 5FF-TOB | (this Invention) | 260 |
| 5FF-TOB-AHB | (this Invention) | >300 |
| Genta-$C_1$ | (comparative) | ca.70 |
| 5FF-Genta-$C_1$ | (this Invention) | ca.200 |
| Genta-$C_2$ | (comparative) | ca.90 |
| 5FF-genta-$C_2$ | (this Invention) | ca.230 |
| Genta-$C_{1a}$ | (comparative) | ca.60 |
| 5FF-genta-$C_{1a}$ | (this Invention) | ca.240 |
| Netilmicin | (comparative) | 30 |
| 5FF-netilmicin | (this Invention) | 47 |

BEST EMBODIMENTS FOR WORKING THE INVENTION

For the preparation of the compound having the general formula (Ia) amongst the compounds of the general formula (I) according to this invention, there is provided according to the third aspect of this invention a process for the production of a 4,6-di-O-(aminoglycosyl)-2,5-dideoxy-5,5-difluorostreptamine derivative represented by the general formula

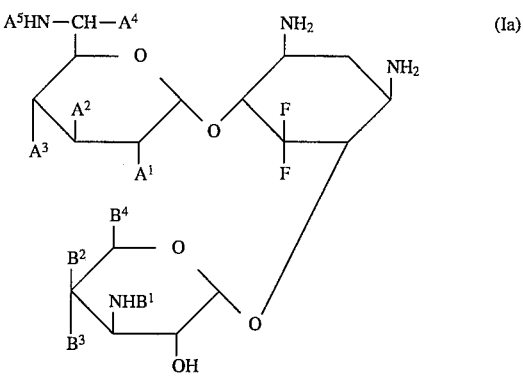

wherein $A^1$, $A^2$, $A^3$, $A^4$ and $A^5$ as well as $B^1$, $B^2$, $B^3$ and $B^4$ respectively have the same meanings as defined for the formula (Ia) described as above, characterized in that the process comprises reacting an N,O-protected 5-keto derivative of kanamycin A, a deoxykanamycin A, a dideoxykanamycin A, kanamycin B, a deoxykanamycin B, a dideoxykanamycin B, 3'-fluoro-3'-deoxykanamycin B, 3'-fluoro-3', 4'-dideoxykanamycin B, gentamicin $C_1$, gentamicin $C_{1a}$ or gentamicin $C_2$ or sagamicin represented by the general formula

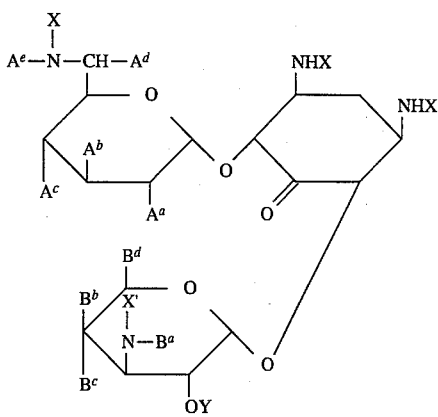
(II)

wherein X and X' respectively are amino-protecting groups which may be the same or different; Y is a hydroxyl-protecting group; $A^a$ is a protected hydroxyl group or a protected amino group; $A^b$ and $A^c$ respectively are a hydrogen atom, a protected hydroxyl group or a fluoro group; $A^d$ is a hydrogen atom or methyl group, namely is same as $A^4$ set forth in the general formula (I) above; $A^e$ is a hydrogen, atom or methyl group, namely- is same as $A^5$ set forth in the general formula (I); and $B^a$ is a hydrogen atom or methyl group, namely is same as $B^1$ set forth in the general formula (I); $B^b$ and $B^c$ respectively are a hydrogen atom, a protected hydroxyl group (OY) or a protected hydroxyl group (OY') as protected by a different hydroxyl-protecting group, or a methyl group; $B^d$ is a hydrogen atom or a hydroxymethyl group as protected at its hydroxyl moiety and having formula ($-CH_2OY$); and Y' is a hydroxyl-protecting group different from the group Y, with a dialkylaminosulfur trifluoride of the formula

(III)

wherein $R^2$ is an alkyl group of 1 to 4 carbon atoms, or with a bis(dialkylamino)sulfur difluoride of the formula

(III')

wherein $R^2$ is as defined above, or with a fluorination agent equivalent to the compound of formula (III) or (III') in a non-polar organic solvent, to di-fluorinate the ketone group at the 5-position of the 5-keto derivative of the formula (II), thereby producing an N,O-protected 2,5-dideoxy-5,5-difluorostreptamine derivative represented by the general formula

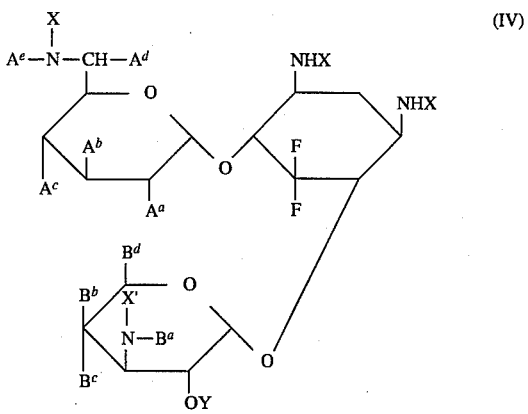
(IV)

wherein X, X', Y, $A^a$, $A^b$, $A^c$, $A^d$, $A^e$, $B^a$, $B^b$, $B^c$ and $B^d$ respectively have the same meanings as defined above, and then removing the remaining amino-protecting groups (X, X') and the remaining hydroxyl-protecting groups (Y, Y') from the compound of the formula (IV) by a conventional method.

The method for preparation of the N,O-protected 5-keto derivative of the formula (II) which is used as a starting compound in the process of the third aspect of this invention is briefly described hereinafter in this specification.

In the starting compound of the formula (II) employed in the above-mentioned process of this invention, all the amino groups born by said compound have been protected by any known and appropriate amino-protecting groups (X, X') which do not participate in the reactions involved and which may be, for example, an acyl group, including an alkanoyl group such as acetyl and trifluoroacetyl; and an aroyl group such as benzoyl; an alkoxycarbonyl group such as methoxycarbonyl, ethoxycarbonyl and butoxycarbonyl; an aralkyloxycarbonyl group such as benzyloxycarbonyl and phenetyloxycarbonyl; or an aryloxycarbonyl group such as phenoxycarbonyl and methoxyphenoxycarbonyl; and a protective group of sulfonyl-type, including e.g. an alkylsulfonyl group, an aralkylsulfonyl group such as benzylsulfonyl and an arylsulfonyl group such as tosyl.

In cases where the starting compound of formula (II) has the hydroxyl groups ($A^a$, $A^b$ and/or $A^c$) e.g. at the 2', 3'- and/or 4'-position thereof in addition to the 5-hydroxyl group, it is necessary that for instance, all of the 2'-hydroxyl group, 3'-hydroxyl group and/or 4'-hydroxyl group and the 2"-hydroxyl group other than the 5-hydroxyl group should be protected by a known hydroxyl-protecting groups (Y, Y') which may be selected from an acyl group, preferably an alkanoyl or an aroyl group. Similarly, where the 4"- and 6"-hydroxyl groups are present, they are necessary to have been protected by known hydroxyl-protecting groups (Y, Y') which may be selected from an acyl group, preferably an alkanoyl or an aroyl group. The acyl group for the protection of the hydroxyl groups may be an alkanoyl group, typically an alkanoyl group of 2–5 carbon atoms such as acetyl, propionyl and butyryl. Acetyl group is preferred. The acyl group may be an aroyl group, which includes phenylcarbonyl group optionally having alkyl substituent(s) on the phenyl ring, preferably benzoyl. Alternatively, the 4"-hydroxyl-protecting group (Y) and 6"-hydroxyl-protecting group (Y) as taken together may form a single known di-valent hydroxyl-protecting group, for example, an alkylidene group of 2–8 carbon atoms such as ethylidene and isopropylidene, or a cycloalkylidene group such as cyclohexylidene, or a tetrahydropyranylidene group.

Examples of the dialkylaminosulfur trifluoride of formula (III), which may be used as the fluorination agent, include typically dimethylaminosulfur trifluoride, diethylaminosulfur trifluoride and dipropylaminosulfur trifluoride. Exemplary of the bis(dialkylamino)sulfur difluorides of formula (III') which may also be used as the fluorination agent are bis(dimethylamino)sulfur, difluoride and bis(diethylamino)sulfur difluoride. All of these compounds are known fluorinating agents [see, "J. Org. Chem.", 40, No. 5, 574–578 (1975)].

The reaction between a compound of formula (II) and a fluorination agent of formula (III) or (III') may be carried out in a non-polar organic solvent, for example, an aromatic hydrocarbon such as benzene, toluene and xylene or chlorinated hydrocarbon such as chloromethane, dichloromethane, chloroform and carbon tetrachloride, or acetonitrile at a temperature in the range of 0°–100° C., preferably at room temperature under an anhydrous condition. The fluorination agent of formula (III) or (III') may be used in an amount of 5–20 moles per mole of the compound of formula (II). An amine such as tertiary alkylamine or pyridine may be present as the acid binding agent in the reaction mixture.

After the completion of the di-fluorination of the 5-ketone group of the compound of formula (II), the reaction solution is added to an aqueous solution of an alkali metal carbonate or an alkali metal hydrogen carbonate, preferably an aqueous sodium hdyrogen carbonate, to neutralize the acidic matter. The resulting mixture so neutralized is extracted with chloroform and the extract is washed with water, dried and concentrated under a reduced pressure to remove the chloroform and to leave the N,O-protected 2,5-dideoxy-5,5-difluorostreptamine derivative of formula (IV) as a solid.

The amino-protecting groups (X, X') and the hydroxyl-protecting groups (Y, Y') remaining in the compound of formula (IV) may be removed by a known deprotecting method. Thus, an amino-protecting group of the alkoxycarbonyl or aryloxycarbonyl-type may be removed by an alkaline hydrolysis, whereas an amino-protecting group of the aralkyloxycarbonyl-type may be removed by an alkaline hydrolysis or by reduction. An amino-protecting group of the sulfonyl-type may also be removed in a known manner by treating the compound of formula (IV) with metallic sodium in liquefied ammonia (see, for example, U.K. Patent No. 1,555,661 and Japanese Patent Publication No. 29720/85). A hydroxyl-protecting group of the acyl type (Y, Y') may be removed by treatment with sodium methoxide in methanol or by hydrolysis in an aqueous solution of alkali metal carbonate or alkali metal hydroxide such as sodium carbonate and sodium hydroxide. In cases where the hydroxyl-protecting groups form a single hydroxyl-protecting group of the alkylidene, cycloalkylidene or tetrahydropyranylidene type, such group may be removed by hydrolysis in the presence of an inorganic acid, an organic acid or a cation exchange resin of strongly acidic nature, e.g. a cation exchange resin having sulfonic acid groups (see, for example, U.K. Patent No. 2,043,634B).

The removal of all the residual amino-protecting and hydroxyl-protecting groups from the compound of formula (IV) results in the formation of the desired compound of formula (Ia) according to this invention. The isolation and purification of the compound of formula (Ia) may suitably be effected by chromatography on a molecular sieve agent such as CM-Sephadex C-25 as eluted with aqueous ammonia in a gradient elution technique.

Further, according to the fourth aspect of this invention, there is provided a process for the production of 5-deoxy-5,5-difluorosisomicin or 5-deoxy-5,5-difluoronetilmicin represented by the formula

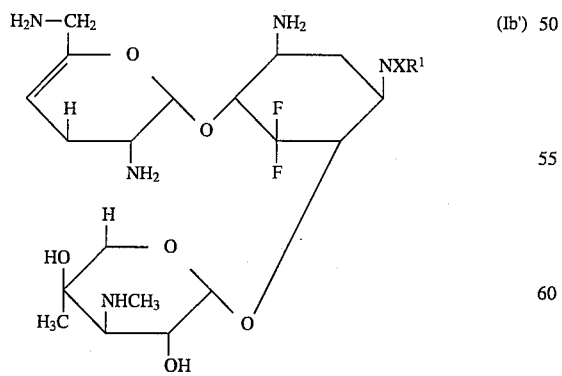

wherein $R^1$ is a hydrogen atom or ethyl group, characterized in that the process comprises reacting an N,O-protected 5-keto derivative of sisomicin or netilmicin represented by the general formula

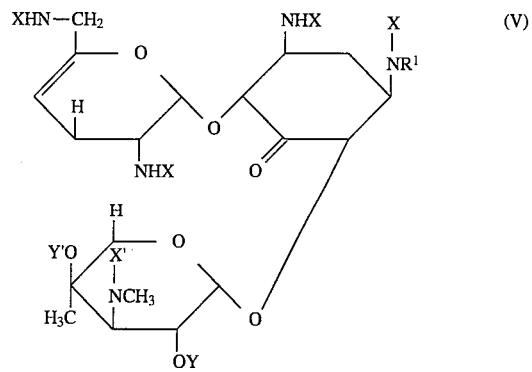

wherein X and X' respectively are amino-protecting groups which may be the same or different; Y and Y' respectively are hydroxyl-protecting groups which may be the same or different; and optionally X' taken with Y' may form such a single carbonyl group which can protect simultaneously the 3"-imino group and the 4"-hydroxyl group of the compound of formula (V); and $R^1$ is a hydrogen atom or ethyl group, with a dialkylaminosulfur trifluoride of the formura

wherein $R^2$ is an alkyl group of 1 to 4 carbon atoms, or with a bis(dialkylamino) sulfur difluoride of the formula $$R^2N-SF_2-NR^2 \quad (III')$$

wherein $R^2$ is as defined above, or with a fluorination agent equivalent to the compound of formula (III) or (III') in a non-polar organic solvent, to di-fluorinate the ketone group at the 5-position of the 5-keto derivative of the formula (V), thereby producing an N,O-protected derivative of 5-deoxy-5,5-difluorosisomicin or 5-deoxy-5,5-difluoronetilmicin represented by the formula

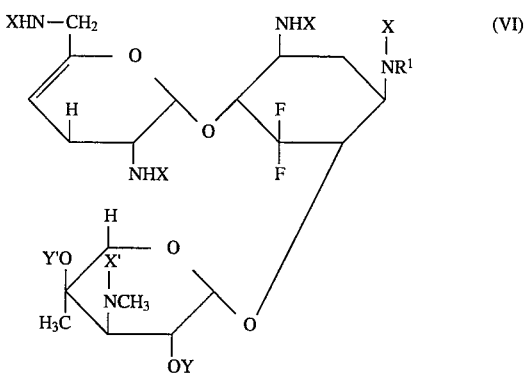

wherein X, X', Y, Y' and $R^1$ respectively have the same meanings as defined for the general formula (V) above, and then removing the remaining amino-protecting groups (X, X') and the remaining hydroxyl-protecting groups (Y, Y') from the compound of the formula (VI) by a conventional method.

Also in the starting compound of the general formula (V) employed in the process according to the fourth aspect of this invention, all of the amino groups born by said compound have been protected by any known and appropriate amino-protecting groups (X, X'). The sorts of the amino-protecting groups used for this purpose may be same as the amino-protecting groups present in the starting compound of the formula (II) used in the process according to the third aspect of this invention. Further, the hydroxyl groups other than the 5-hydroxyl group of the starting compound of the general formula (V) may have been protected by the hydroxyl-protecting groups (Y, Y') which are of the same sort as those for the hydroxyl groups of the compound of the general formula (II). Besides, it is possible that X' at the 3"-methylamino group and Y' at the 4"-hydroxyl group of the compound of the formula (V) are linked to each other to form a single carbonyl group and thereby constitute the form of a cyclic carbamate, whereby the 3"-methylamino group and 4"-hydroxyl group can be protected simultaneously. Such a 3", 4"-N,O-protected derivative wherein the 3"-methylamino group and the 4"-hydroxyl group have been converted into the form of the cyclic carbamate may be provided by preparing from sisomicin or netilmicin firstly such N-protected derivative thereof having benzyloxycarbonyl groups as the amino-protecting groups (X, X') but having the hydroxyl group unprotected, and then reacting said N-protected derivative with sodium hydride in dimethylformamide (DMF) (see Referential Examples 11 and 13 given hereinafter).

In the process according to the fourth aspect of this invention, the di-fluorination of the 5-ketone group of the compound of the formula (V) may again be effected by reacting said ketone group with the fluorinating compound of the formula (III) or formula (III') in the same manner as in the process according to the third aspect of this invention. The resulting 5,5-difluorinated derivative of the formula (VI) is then subjected to conventional deprotection methods for removal of the amino-protecting groups (X, X') and the hydroxyl-protecting groups (Y, Y') therefrom. In this way, there is afforded 5-deoxy-5,5-difluorosisomicin or 5-deoxy-5,5-difluoronetilmicin of the general formula (Ib') as desired.

According to the fifth aspect of this invention, there is provided a process for the production of 5-deoxy-5,5-difluoroseldomycin factor 3 represented by the formula

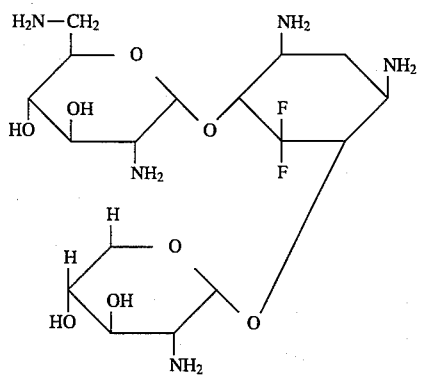
(Id)

characterized in that the process comprises reacting an N,O-protected 5-keto derivative of seldomycin factor 3 represented by the formula

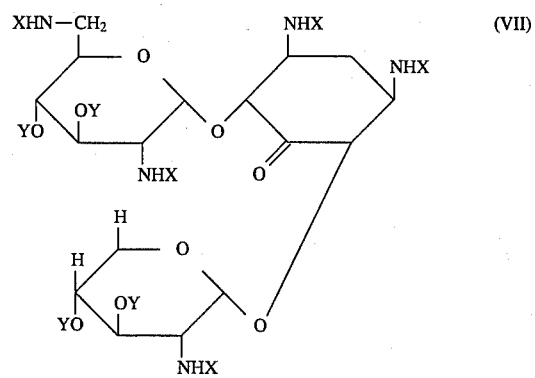
(VII)

wherein X is an amino-protecting group and Y is a hydroxyl-protecting group, with dialkylaminosulfur trifluoride of the formula

(III)

wherein $R^2$ is an alkyl group of 1 to 4 carbon atoms, or with a bis(dialkylamino)sulfur difluoride of the formula

$$R^2N-SF_2-NR^2 \qquad (III')$$

wherein $R^2$ is as defined above, or with a fluorination agent equivalant to the compound of formula (III) or (III') in a non-polar organic solvent, to di-fluorinate the ketone group at the 5-position of the 5-keto derivative of the formula (VII), thereby producing an N,O-protected derivative of 5-deoxy-5,5-difluoroseldomycin factor 3 represented by the formula

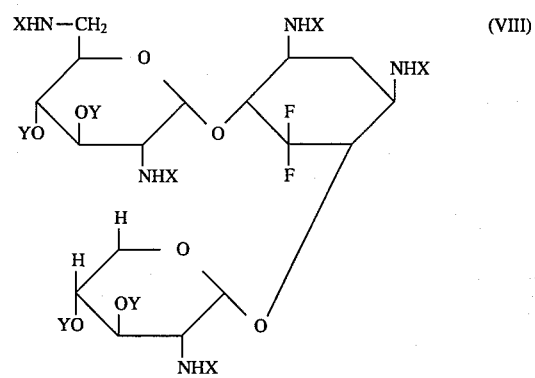
(VIII)

wherein X and Y respectively have the same meanings as defined above, and then removing the remaining amino-protecting group (X) and the remaining hydroxyl-protecting group (Y) from the compound of the formula (VIII) by a conventional method.

Also in the starting compound of the general formula (VII) employed in the process according to the fifth aspect to this invention, all of the amino groups born by this seldomycin compound have been protected by any known and appropriate amino-protecting group (X). The sort of the amino-protecting group available for this purpose may be same as the amino-protecting groups which are provided in the starting compound of the general formula (II) used in the process according to the third aspect of this invention. Besides, the hydroxyl groups other than the 5-hydroxyl group of the starting compound of the general formula (VII) may also have been protected by the hydroxyl-protecting group (Y) which is of the same sort as for the hydroxyl groups of the compound of the general formula (II).

Also in the process according to the fifth aspect of this invention, the di-fluorination of the 5-ketone group of the compound of the formula (VII) may be achieved by reacting said ketone group with the fluorinating compound of the formula (III) or formula (III') in the same manner as in the process according to the third aspect of this invention. The 5,5-difluorinated derivative so obtained of the formula (VIII) is then subjected to conventional deprotection methods. Thus, there is obtained 5-deoxy-5,5-difluoroseldomycin factor 3 of the general formula (Id) as desired.

Method for preparing the N,O-protected 5-ketonized derivatives of the formula (II), formula (V) and formula (VII) which are employed as the starting compound in the aforesaid processes according to the third, fourth and fifth aspects of this invention will next be described.

This preparing method comprises a series of stages as detailed below. Thus, at first, there is employed as an initial material a 4-O-(aminoglycosyl)- or 4,6-di-O-(aminoglycosyl)-2-deoxystreptamine represented by the foregoing general formula (A). Then, there is conducted a first stage where the amino-protecting groups (X, X') are introduced into all the amino groups of the 2-deoxystreptamine derivative of the general formula (A). This first stage comprises effecting the reaction for the introduction into the amino groups of the compound of the formula (A) such a mono-valent amino-protecting groups, including typically an alkoxycarbonyl group such as tert-butoxycarbonyl and tert-amyloxycarbonyl; a cycloalkyloxycarbonyl group such as cyclohexyloxycarbonyl; an aralkyloxycarbonyl group such as benzyloxycarbonyl; a hydrolytically cleavable, substituted lower alkanoyl group such as trifluoroacetyl and o-nitrophenoxyacetyl; a phosphinothioyl group such as diphenylphosphinothioyl and dimethylphosphinothioyl; a phosphinyl group such as dephenylphosphinyl; or alternatively such a divalent amino-protecting groups which may be phthaloyl or may form a Schiff base with the amino group to be protected.

The introduction of the amino-protecting group of these kinds may be conducted by employing an appropriate known reagent for introduction of the amino-protecting group which may be in the form of an acylating agent such as an acid halide, acid azide, active ester, acid anhydride and the like, according to the techniques known per se in the conventional synthesis of peptides or for protection of amino groups of kanamycins. By choosing the quantity of the reagent for introduction of the amino-protecting group in a proportion of 1 to 2 moles per one amino group present in the molecule of the starting 2-deoxystreptamine derivative of the general formula (A) as the initial material, it is possible to prepare such an amino-protected derivative of the starting compound of the general formula (A) of which all the amino groups present have been protected.

Then, in such cases when the above-mentioned first stage is achieved so as to introduce an alkylsulfonyl group, aralkylsulfonyl group or arylsulfonyl group as the amino-protecting group to be used, this first stage may be effected in a known manner by reacting the starting compound of the general formula (A) with a sulfonic acid halide of the formula

where $R^3$ is a lower alkyl group, an aralkyl group, particularly benzyl group or an aryl group, particularly phenyl group; and Hal is chlorine or bromine, preferably tosyl chloride in aqueous dioxane in the presence of sodium carbonate at a temperature of 0° to 50° C. (see, for example, U.K. patent No. 1,555,661 and Japanese patent publication No. Sho-60-29720 specification).

Next, the second stage is conducted, where all of the hydroxyl groups other than the 5-hydroxyl group of the above-mentioned amino-protected derivative derived from the starting compound of the general formula (A) are protected by a hydroxyl-protecting group.

In this second stage, said amino-protected derivative is reacted with acetyl chloride or acetic anhydride in anhydrous pyridine at a temperature of 50° C. or less, e.g, at 0° C. with using acetyl chloride or acetic anhydride in a proportion of 1.5 to 5 moles or in a slightly excessive proportion per one hydroxyl group present in said amino-protected derivative. Then, all of the hydroxyl groups other than the 5-hydroxyl group of said amino-protected derivative, that is, all the hydroxyl groups at the 2'-, 3'-, 4'-, 2"-, 3"- and 4"-positions and also at the 6"-position (but excepting such a case where the hydroxyl group is absent at the 6"-position) of the amino-protected derivative can be protected by acetylation. In general, even when an acyl chloride, including a lower alkanoyl chloride other than acetyl chloride, as well as an aroyl chloride such as benzoyl chloride is used in place of acetyl chloride or acetic anhydride, all the hydroxyl groups other than the 5-hydroxyl group of said amino-protected derivative can similarly be protected by the acylation with the 5-hydroxyl group being not acylated under the action of the steric hindrance in the molecule of the amino-protected derivative. In this way, there is formed the N,O-protected 2-deoxystreptamine derivative having the free 5-hydroxyl group and generically represented by the general formula (B) given hereinbefore.

More particularly, the N,O-protected 2-deoxystreptamine derivative so prepared may include the N,O-protected 2-deoxystreptamine derivatives of the following general formulae (II'), (V') and (VII'):

(a) An N,O-protected derivative of kanamycin A, a deoxykanamycin A, a dideoxykanamycin A, kanamycin B, a deoxykanamycin B, a dideoxykanamycin B, 3'-fluoro-3'-deoxykanamycin B, 3'-fluoro-3', 4'-dideoxykanamycin B, gentamicin $C_1$, gentamicin $C_{1a}$ or gentamicin $C_2$ or sagamicin represented by the general formula

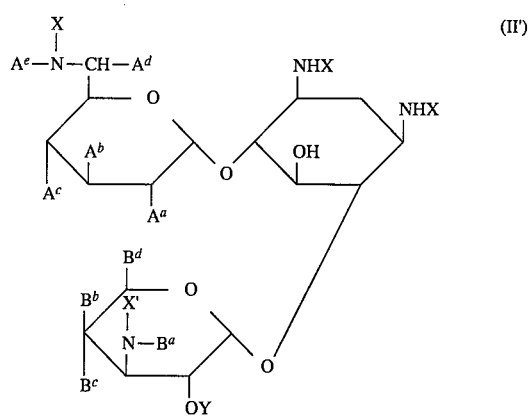

(II')

wherein X and X' respectively are amino-protecting groups which may be the same or different; Y is a hydroxyl-protecting group; $A^a$ is a protected hydroxyl group or a protected amino group; $A^b$ and $A^c$ respectively are a hydrogen atom, a protected hydroxyl group or a fluoro group; $A^d$ is a hydrogen atom or methyl group, namely is same as $A^4$ set forth in the general formula (I) above; $A^e$ is a hydrogen atom or methyl group, namely is same as $A^5$ set forth in the general formula (I); and $B^a$ is a hydrogen atom or methyl group, namely is same as $B^1$ set forth in the general formula (I); $B^b$ and $B^c$ respectively are a hydrogen atom, a protected hydroxyl group (OY) or a protected hydroxyl group (OY') as protected by a different hydroxyl-protecting group, or a methyl group; $B^d$ is a hydrogen atom or a hydroxymethyl group as protected at its hydroxyl moiety and having formula (—CH$_2$OY); and Y' is a hydroxyl-protecting group different from the group Y.

(b) An N,O-protected derivative of sisomicin or netilmicin represented by the general formula

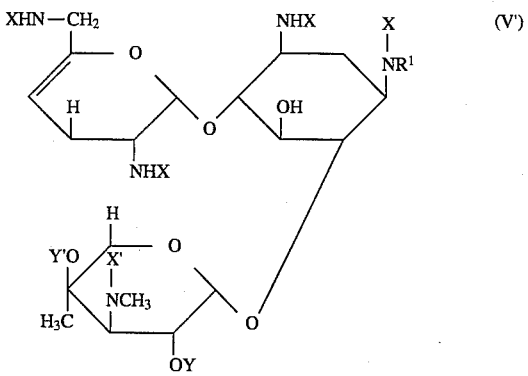

wherein X and X' respectively are amino-protecting groups which may be the same or different; Y and Y' respectively are hydroxyl-protecting groups which may be the same or different; and optionally X' taken with Y' may form such a single carbonyl group which can protect simultaneously the 3"-imino group and the 4"-hydroxyl group of the compound of formula (V'); and $R^1$ is a hydrogen atom or ethyl group.

(c) An N,O-protected derivative of seldomycin factor 3 represented by the formula

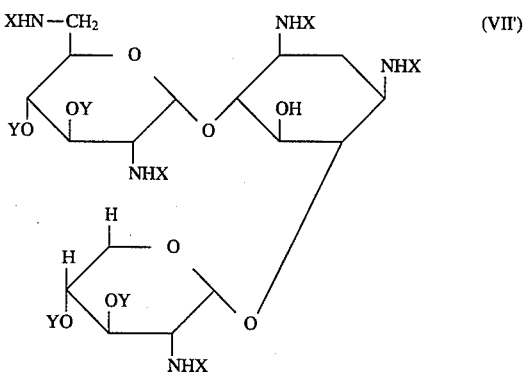

wherein X is an amino-protecting group and Y is a hydroxyl-protecting group.

Further, the third stage is conducted, where the 5-hydroxyl group of the compound of the general formula (B) is oxidized and thereby said compound is converted into the 5-keto derivative of the general formula (C) shown hereinbefore. Thus, more particularly, this third stage comprises either oxidizing the 5-hydroxyl group of the N,O-protected derivative of the above general formula (II') to produce the 5-keto derivative of the general formula (II), or oxidizing the 5-hydroxyl group of the N,O-protected derivative of the general formula (V') to produce the 5-keto derivative of the general formula (V), or oxidizing the 5-hydroxyl group of the N,O-protected derivative of the general formula (VII') to produce the 5-keto derivative of the general formula (VII). The reaction for oxidation in this third stage may be conducted by the following procedure. Thus, said N,O-protected derivative is reacted e.g., with pyridinium chlorochromate (PCC) or a mixture of dimethylsulfoxide-acetic anhydride as a mild oxidizing agent which is known to oxidize a hydroxyl substitutent of organic compounds into a ketone group, so that the oxidation of the 5-hydroxyl group into the 5-ketone group can be achieved. Suitable examples of solvents available in this oxidation reaction include dichloromethane, pyridine, DMSO, a mixture of pyridine and DMSO, benzene, carbon tetrachloride, chloroform, acetonitrile and the like. The oxidation may suitably be carried out at a reaction temperature of −20° C. to 100° C. This oxidation reaction can be finished within one week (see Referential Example 1(c) given hereinafter).

According to the sixth aspect of this invention, there is provided a process for the production of a 1-N-(α-hydroxyl-ω-aminoalkanoyl)-4,6-di-O-(aminoglycosyl)-2,5-dideoxy-5,5-difluorostreptamine derivative represented by the general formula

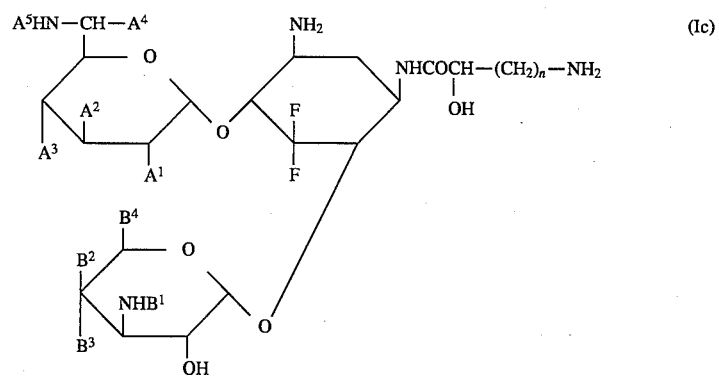

wherein $A^1$, $A^2$, $A^3$, $A^4$ and $A^5$, as well as $B^1$, $B^2$, $B^3$ and $B^4$ have the same meanings as defined for the general formula (I) hereinbefore or for the general formula (Ia) hereinbefore, and n is an integer of 1 to 3, which comprises reacting the 1-amino group of a 4,6-di-O-(aminoglycosyl)-2,5-dideoxy-5,5-difluorostreptamine derivative represented by the general formula

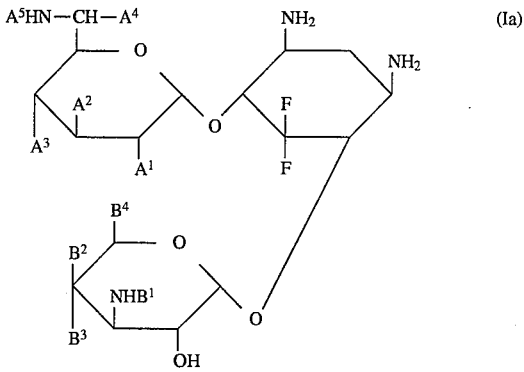

wherein $A^1$, $A^2$, $A^3$, $A^4$ and $A^5$, as well as $B^1$, $B^2$, $B^3$ and $B^4$ respectively have the same meanings as defined above, or the 1-amino group of such a protected derivative of the compound of formula (Ia) whose some or all of the amino groups other than said 1-amino group has or have been protected by amino-protecting groups, with an α-hydroxy-ω-aminoalkanoic acid having the general formula

wherein n is an integer of 1 to 3, or such a protected derivative of said aminoalkanoic acid whose the amino group has been protected by an amino-protecting group, and then removing from the resulting 1-N-acylated product the remaining amino-protecting groups when the latter protective groups exist, to produce the compound of formula (Ic).

In the process according to the sixth aspect of this invention, all or some of the amino groups other than the 1-amino group of the 2,5-dideoxy-5,5-difluorostreptamine derivative of the general formula (Ia) are protected by appropriate amino-protecting groups. The amino-protecting group available for this purpose includes conventional amino-protecting groups. For instance, there may be employed an alkoxycarbonyl group such as methoxycarbonyl, ethoxycarbonyl and tert-butoxycarbonyl; an aralkyloxycarbonyl group such as benzyloxycarbonyl; and an acyl group such as phenoxycarbonyl, acetyl, trifluoroacetyl and benzoyl, as well as a sulfonyl group such as tosyl. The introduction of the amino-protecting group of these kinds may be achieved in a known manner by reacting the 2,5-dideoxy-5,5-difluorostreptamine derivative of the general formula (Ia) with an appropriate known reagent for the introduction of the amino-protecting group, which may be in the form of an acylating agent such as an acid halide, acid azide, active ester, acid anhydride and the like, by a conventional method known in the synthesis of peptides. By choosing the quantity of the reagent for the introduction of the amino-protecting group in a proportion of 0.5 to 6 moles per mole of the compound of the formula (Ia), it is possible to prepare from the difluoro compound of the general formula (Ia) different, partially amino-protected derivatives thereof in different proportions due to difference in the reactivities of the respective amino groups of the compound of the formula (Ia).

In this process, it is possible to use, such amino,protected derivative of the difluoro compounds of general formula (Ia) whose all or some of the amino groups other than the 1-amino group have been protected, for example, a 3,2',6',3"-tetra-N-protected derivative, a 3,2',6'-tri-N-protected derivative, a 6',3"-di-N-protected derivative or a 6'-mono-N-protected derivative. A mixture of two or more of those partially N-protected derivatives may also be used for the acylation of the 1-amino group with the substituted aminoalkanoic acid of the formula (IX) in the process of the sixth aspect of this invention.

The production of the 1-N-acylated product of the general formula (Ic) in a high yield in the process of the sixth aspect of this invention, can be achieved by acylating the 1-amino group of the starting difluoro compound of formula (Ia) selectively with the α-hydroxy-ω-amino-alkanoic acid of formula (IX). Accordingly, it will be evident that most preferably, such a protected derivative of the compound of formula (Ia) whose all the amino groups other than the 1-amino group have been protected, namely a 3,2',6',3"-tetra-N-protected-2,5-dideoxy-5,5-difluorostreptamine derivative is employed as the starting substance to be 1-N-acylated in this process.

To prepare such an amino-protected derivative of the compound of the general formula (Ia) of which all the amino groups other than the 1-amino group have been protected, it is convenient to utilize the following procedures. Thus, for instance, firstly a 3,6'-di-N-protected or 3,2',6'-tri-N-protected derivative derived from the 2,5-dideoxy-5,5-difluorostreptamine derivative of the formula (Ia) is produced in a high yield by application of such amino-protecting method according to claim 1 of Japanese patent application first publication "Kokai" No. Sho-55-64598 or U.S. Pat. No. 4,297,485, that comprises reacting the compound of the formula (Ia) with zinc cation to form a zinc complex, reacting this zinc complex with the reagent for the introduction of amino-protective group to protect with the amino-protective group all of the amino groups other than the two 1-amino and 3"-amino groups of said zinc complex (with the 1-amino and 3"-amino groups remaining blocked by complexing with zinc cation), and then removing the zinc cation from the resulting amino-protected zinc complex, e.g. by treatment with a cation-exchange resin or treatment with hydrogen sulfide or treatment with aqueous ammonia. (In this case, it is also possible to replace zinc cation by a cation of cobalt, copper, nickel and the like which is employed in the process of Japanese patent application first publication "Kokai" No. Sho-52-153944 or its corresponding U.S. Pat. No. 4,136,254). Subsequently, the 3"-amino group of said 3,6'-di-N-protected or 3,2',6'-tri-N-protected derivative so produced is preferentially acylated by application of a method for preparation of an amino-protected derivative having selectively all the amino groups protected except the 1-amino group set forth in claim 15 of Japanese patent application first publication "Kokai" No. Sho-55-164696 or U.S. Pat. No. 4,297,485, whereby there can be prepared in a high yield such a tri-N-protected or tetra-N-protected derivative derived from the 5,5-difluoro compound of formula (Ia), of which all the amino groups other than the 1-amino group have been protected. The U.S. Pat. No. 4,297,485 specification describes such a process wherein such an amino-protected derivative of an aminoglycoside antibiotic whose all the amino groups other than the 1-amino and 3"-amino groups have been protected is reacted with e.g., with a formic acid ester, a di-halogenated alkanoic acid ester or a tri-halogenated alkanoic acid ester for preferential acylation of the 3"-amino group, so that the 3"-amino group can preferentially be protected by the formyl group, di-haloalkanoyl group or tri-haloalkanoyl group without involving the acylation of the 1-amino group of said aminoglycoside antibiotic.

In the process of the sixth aspect of this invention, the α-hydroxy-ω-aminoalkanoic acid of the formula (IX) used may be an α-hydroxy-ω-aminoalkanoic acid of which the amino group has been protected or not. This substituted alkanoic acid (IX) is used to acylate the 1-amino group of the compound of the formula (Ia) or its partially amino-protected derivative. This 1-N-acylation reaction may be conducted by reacting the compound of formula (Ia) or its amino-protected derivative with the α-hydroxy-ω-aminoalkanoic acid of formula (IX) according to a so-called dicyclohexylcarbodiimide method, mixed acid anhydride method, azide method, active ester method etc., at a reaction temperature suitably in a range of 0° C. to 30° C. The amino-protecting group which may be used conveniently in this process of the present invention includes tert-butoxycarbonyl group and p-methoxybenzyloxycarbonyl group which are easily cleavable by treatment with aqueous trifluoroacetic or acetic acid or with dilute aqueous hydrochloric acid. Benzyloxycarbonyl group which is removable by a conventional hydrogenolysis in the presence of a catalyst of platinum group metal, such as palladium or platinum oxide is also a convenient amino-protecting group.

The 1-N-acylation in the process of the sixth aspect of this invention may desirably be carried out in an aqueous organic solvent according to the active ester method. For example, N-hydroxysuccinimide ester of (S)-4-tert-butoxycarbonylamino-2-hydroxybutyric acid may preferably be used as the active ester which may be prepared by a conventional method of preparing such active esters. This active ester may usually be used in a proportion of from 1 to 3 molar equivalents and preferably of from 1 to 1.5 molar equivalents per mole of the starting compound of formula (Ia) or a partially amino-protected derivative thereof to be 1-N-acylated. The solvent used as the reaction medium may be a water-miscible organic solvent such as dioxane, dimethoxyethane, dimethylformamide, tetrahydrofuran, triethylamine and the like.

The 1-N-acylated product so obtained from the 1-N-acylation step is then subjected to the removal of the amino-protecting groups, when these amino-protective groups are still remaining in the 1-N-acylated product. The removal of the amino-protecting groups is effected by a conventional deprotecting technique. Thus, the amino-protecting group of alkoxycarbonyl type is removed by acid hydrolysis with an aqueous solution of trifluoroacetic acid or acetic acid etc., or with a dilute aqueous solution of an inorganic acid such as hydrochloric acid. The amino-protecting group of aralkyloxycarbonyl type such as benzyloxycarbonyl may easily be removed by an ordinary catalytic reduction (hydrogenolysis).

The synthesis of the compound of the formula (Ic) in accordance with the process of the sixth aspect of this invention is convenient to be conducted by a synthetic route comprising starting from an unprotected compound of the formula (Ia), for example, 5-deoxy-5,5-difluorokanamycin B, firstly preparing from such starting compound its amino-protected derivative having all the amino groups protected except the 1-amino group by utilization of the amino-protecting method of U.S. Pat. No. 4,297,485 and subsequently carrying out the process of the sixth aspect of this invention with using the so prepared amino-protected derivative. More concretely, for instance, it is convenient to conduct such a synthetic route comprising the following steps (i) to (iv).

(i) Firstly, the starting compound of formula (Ia) and zinc acetate (or cobalt acetate) are either suspended in dimethylsulfoxide (DMSO) or dissolved in a mixture of water and dimethylformamide (DMF), and the resulting suspension or solution of the complex of the compound (Ia) and zinc cation (or cobalt cation) as formed is reacted with N-(benzyloxycarbonyloxy)-succinimide (namely, a reagent for the introduction of the amino-protecting benzyloxycarbonyl group) to protect the 3-, (2'-) and 6'-amino groups of the compound (Ia) moiety of the zinc complex with the benzyloxycarbonyl groups, and thereby to form the complex of zinc (or cobalt) with such partially amino-protected derivative of the compound (Ia), followed by removing the zinc (or cobalt) cation from the latter complex by treating with a cation-exchange resin (such as Amberlite CG-50), to give 3,(2'),6'-tris(or bis)-N-benzyloxy-carbonylated compound (Ia), namely Compound (a) ( . . . Step i).

(ii) Compound (a) is then reacted with ethyl trifluoroacetate in DMSO or DMF to protect the 3''-amino group of Compound (a) with the trifluoroacetyl group, affording 3,(2'),6'-tris(or bis)-N-benzyloxycarbonyl-3''-N-trifluoroacetylated compound (Ia), namely Compound (b) ( . . . Step ii).

(iii) Further, Compound (b) is reacted with N-(benzyloxycarbonyl)-(S)-4-amino-2-hydroxybutyryloxy-succinimide or with N-(benzyloxycarbonyl)-(S)- or (RS)-3-amino-2-hydroxypropionyloxysuccinimide in an aqueous tetrahydrofuran in the presence of sodium carbonate, so that the 1-amino group of Compound (b) is selectively acylated with the (S)-4-benzyloxycarbonylamino-2-hydroxybutyryl group or with the (S)- or (RS)-3-benzyloxy carbonylamino-2-hydroxypropionyl group ( . . . Step iii). Thereby, there is formed 1-N-[(S)-4-(benzyloxycarbonyl) amino-2-hydroxybutyryl]- or 1-N-[(S)- or (RS)-3-(benzyloxy-carbonyl) amino-2-hydroxypropionyl]-3,(2'),6'-tris (or bis)-N-(benzyloxycarbonyl)-3''-N-trifluoroacetylated compound (Ia), namely Compound (c) as the 1-N-acylation product.

(iv) Compound (c) is then subjected to deprotecting treatment comprising acidic or alkaline hydrolysis for the removal of the amino-protecting trifluoroacetyl group therefrom and subsequent catalytic hydrogenolysis in the presence of a platinum group metal catalyst such as palladium or Raney nickel for the removal of the amino-protecting benzyloxycarbonyl groups therefrom ( . . . Step iv).

The compound of the formula (Ic) as desired may thus be produced with a high efficiency through these step (i) to step (iv) described above.

Furthermore, the compounds of the general formula (I) according to this invention also include a compound represented by the general formula

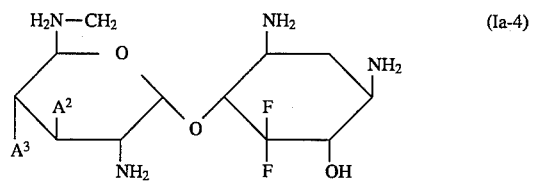
(Ia-4)

wherein (i) $A^2$ and $A^3$ are each a hydroxyl group, or (ii) $A^2$ is a hydrogen atom and $A^3$ is a hydroxyl group, or (iii) $A^2$ and $A^3$ are each a hydrogen atom, or (iv) $A^2$ is a fluoro group and $A^3$ is a hydroxyl group, or (v) $A^2$ is a fluoro group and $A^3$ is a hydrogen atom, and which is namely (i) 5-deoxy-5,5-difluoroneamine, or (ii) 5,3'-dideoxy-5,5-difluoroneamine, or (iii) 5,3',4'-trideoxy-5,5-difluoroneamine, or (iv) 5,3'-dideoxy-5,3',5'-trifluoroneamine, or (v) 5,3',4'-trideoxy-5,5,3'-trifluoroneamine. The compound of the general formula (Ia-4) may be produced by hydrolysing the 5,5-difluorokanamycin B derivative having the general formula (Ia-2) given hereinbefore, with a diluted hydrochloric acid at a temperature of 50°–100° C. so that the glycosyl group linked to the 6-position of said kanamycin B compound (Ia-2) is cleaved therefrom (see Examples 19 and 20 given hereinafter).

Besides, an antibacterial composition comprising the compound of this invention having the general formula (I) as the active ingredient may be formulated by mixing the compound of the general formula (I) with one or more carriers of various kinds and optionally further adding different additives into the composition.

The formulations for administration of the compound of the general formula (I) according to this invention may be of any forms for oral, parenteral and intrarectal administrations. When an injectable formulation is to be prepared, the compound of the general formula (I) according to this invention or a salt thereof to be used as the active ingredient may be admixed with a pH-adjuster, buffer, stabilizer, excipient and the like, and the resulting admixture may be lyophilized by a conventional method to prepare a lyophilized preparation for the injection. Further, the compound of this invention may be admixed with a pH-adjuster, buffer, stabilizer, isotonising agent, local anesthetics and the like, and the resulting mixture may be formulated in a conventional manner into a preparation adapted for subcutaneous, intramuscular or intravenous injection.

When a solid formulation for oral administration is to be prepared, the compound of this invention may be mixed with excipient, optionally together with binder, disintegrator, lubricant, colorant, flavor, odor-improver and the like, followed by forming the resulting mixture into tablet, coated tablet, granule, powder, capsule and the like by conventional methods.

When a liquid formulation for oral administration is to be prepared, the compound of this invention may be mixed with flavor, buffer, stabilizer, odor-improver and the like, followed by formulating the resulting mixture into a syrup or dried syrup by conventional methods.

Where a suppository formulation for intrarectal administration is prepared, the compound of this invention may be mixed with excipient and, if necessary, also with surfactant, followed by forming the resultant mixture into a suppository drug by a conventional method.

The dosage of the compound of this invention will depend on the nature of diseases to be treated and conditions of the diseases, but its optimum dosage can be decided by ordinary and appropriate, preliminary tests.

The production of the compound of the general formula (I) according to this invention is next illustrated with reference to the following Referential Examples and Examples, to which this invention is not limited.

In the following Referential Examples and Examples, there are shown structural formulae for representing the concerned compounds, wherein Ac denotes an abbreviation of acetyl group; Z denotes an abbreviation of benzyloxycarbonyl group; Bz denotes an abbreviation of benzoyl group; AFT denotes an abbreviation of trifluoroacetyl group.

Referential Example 1

(a) Preparation of 1,3,6,3''-tetrakis(N-benzyloxycarbonyl) kanamycin A (Compound 1)

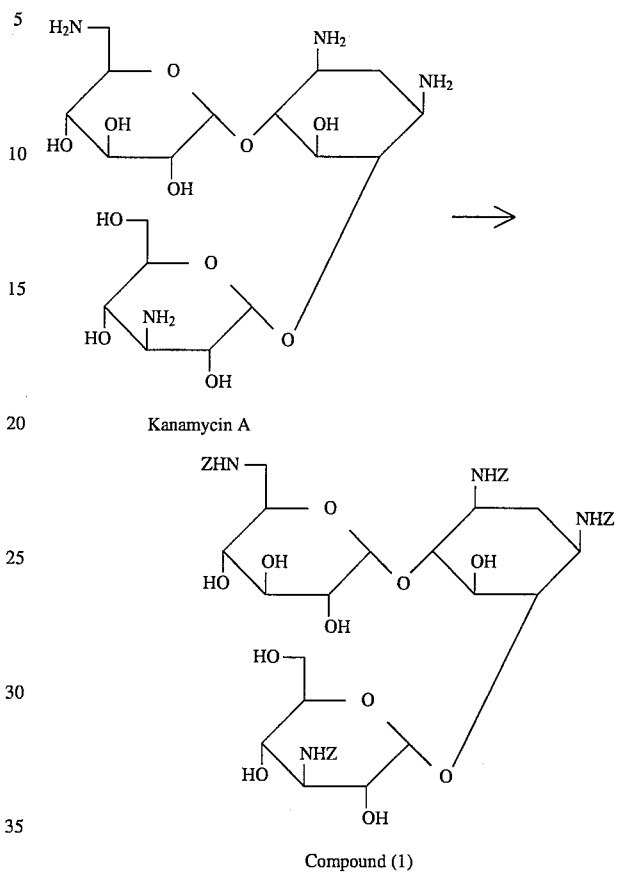

Kanamycin A sulfate (3 g) and sodium carbonate (2.93 g) were dissolved in a mixed solvent (60 ml) of water and acetone (1:1) to which benzyloxycarbonyl chloride (2.90 ml) was added, followed by effecting the reaction for 3 hours under ice-cooling and stirring. Water (200 ml) was added to the reaction solution, and the precipitate formed was filtered, washed with water, dried and then washed with ethyl ether to give the titled Compound (1) (4.6 g, yield 90%).

(b) Preparation of 2',3',4',2'',4'',6''-hexa-O-acetyl-1,3,6',3''-tetrakis (N-benzyloxycarbonyl) kanamycin A (Compound 2)

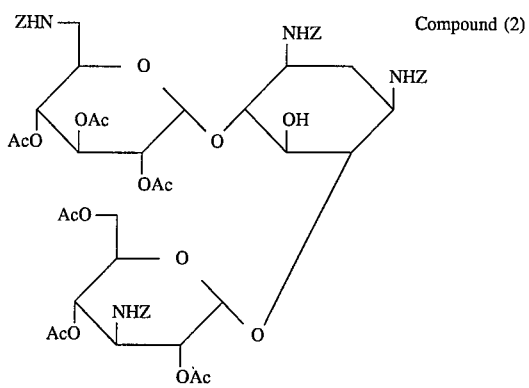

The compound (1) (4.6 g) as obtained in the step (a) above was dissolved in dry pyridine (92 ml) to which acetic anhydride (10.2 ml) was added and O-acetylation reaction was conducted at room temperature overnight. Water (9.73 ml) was added to the reaction solution, and the resulting solution was left to stand for 30 minutes and then concentrated to dryness. The residue was extracted with chloroform and the resultant extract solution was successively washed with an 10% aqueous solution of potassium hydrogen sulfate, a saturated aqueous solution of sodium hydrogen carbonate and water, dried over anhydrous sodium sulfate and concentrated to dryness to obtain the titled compound (2) (5.66 g, yield 99%).

$[\alpha]_D^{23}$+71° (c 1.02, chloroform).

(c) Preparation of 2',3',4',2",4",6"-hexa-O-acetyl-1,3,6', 3"-tetrakis (N-benzyloxycarbonyl)-5-deoxy-5-oxokanamycin A (Compound 3)

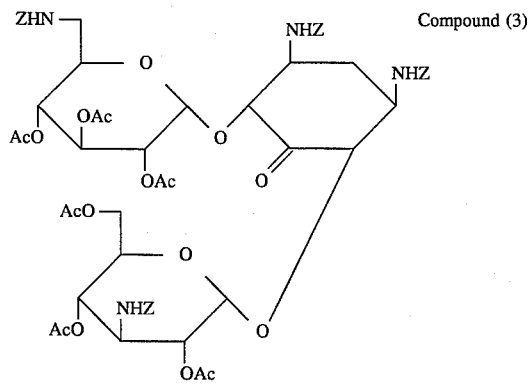

Compound (3)

The compound (2) (893 mg) as obtained in the step (b) above, namely, 2',3',4',2",4",6"-hexa-O-acetyl-1,3,6',3"-tetrakis(N-benzyloxycarbonyl)kanamycin A was dissolved in dry dimethylsufoxide (2.7 ml) to which acetic anhydride (1.8 ml) was added, followed by effecting the reaction at room temperature for 4 days. At this time, a part of dimethylsufoxide acted as an oxidizing agent and the OH group at the 5-position of the compound (2) was oxidized. The reaction solution was poured into a saturated aqueous solution (90 ml) of sodium hydrogen carbonate and the resultant solution was stirred for 2 hours. The precipitate formed was filtered, taken into chloroform and then successively washed with an saturated aqueous solution of sodium hydrogen carbonate and water and dried over anhydrous sodium sulfate. The resultant solution was concentrated to dryness to obtain the titled Compound (3) (749 mg, yield 84%).

Example 1

(a) Preparation of 2',3',4',2",4",6"-hexa-O-acetyl-1,3,6', 3"-tetrakis(N-benzyloxycarbonyl)-5-deoxy-5,5-difluorokanamycin A (Compound 4)

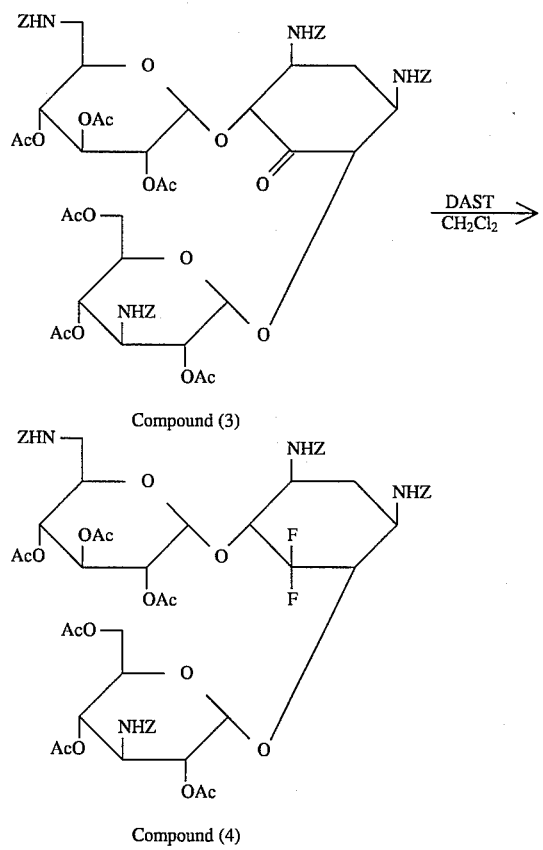

The compound (3) (551 mg) as obtained in Referential Example 1(c) was dissolved in a dry dichloromethane (17 ml) to which diethylaminosulfur trifluoride (0.74 ml) was added under ice-cooling, followed by effecting the reaction at room temperature for 5 hours (for di-fluorination). The resultant reaction solution was poured into an aqueous solution (60 ml) of sodium hydrogen carbonate with stirring and under ice-cooling, and then stirring was continued for 1 hour. The dichloromethane layer was separated and concentrate to dryness. The resultant solid was separated and purified by chromatography on silica gel column (developer: chloroform-acetone, 9:2) to obtain the titled Compound (4) (268 mg, yield 48%).

(b) Preparation of 1,3,6',3"-tetrakis(N-benzyloxycarbonyl)-5-deoxy-5,5-difluorokanamycin A (Compound 5)

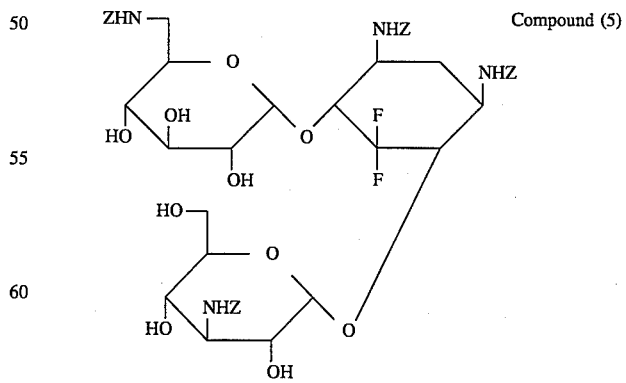

Compound (5)

The compound (4) (185 mg) as obtained in the step (a) above was dissolved in a mixed solvent of methanol (7.4 ml) and water (0.74 ml) to which sodium carbonate (210 mg) was added, followed by vigorous stirring at room temperature for 2 hours. A dilute hydrochloric acid was added to the reaction solution to neutralize it and the resultant solution was concentrated to dryness. The residue was washed with water and dried to obtain the titled Compound (5) (121 mg, yield 81%).

(c) Preparation of 5-deoxy-5,5-difluorokanamycin A (Compound 6)

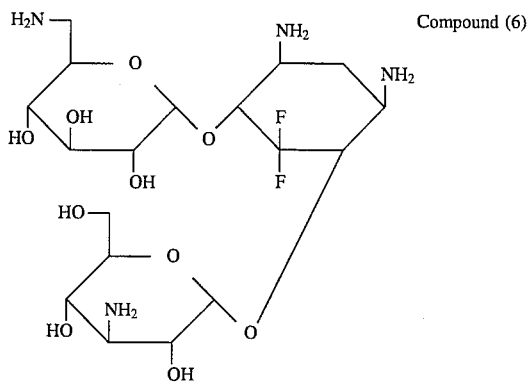

Compound (6)

The compound (5) (73.4 mg) as obtained in the step (b) above was dissolved in a mixed solvent of dioxane, acetic acid and water (4:1:1) (4.4 ml) to which palladium black was added as a catalyst, followed by effecting the catalytic reduction at room temperature for 1 hour (for de-benzyloxycarbonylation). The reaction solution was filtered and the filtrate was concentrated to dryness. The resulting solid was chromatographed in a column of "CM-Sephadex C-25" developed with aqueous ammonia while changing the concentration of ammonia from 0N to 0.15N, and the fractions of the eluate containing the intended substance were concentrated to dryness to obtain the titled Compound (6) (23.6 mg, yield 58%, calculated as the monocarbonate monohydrate).

$[\alpha]_D^{20}$+130° (c 1, water).

Referential Example 2

(a) 3,6'-bis (N-benzyloxycarbonyl)-5-deoxy-5,5-difluorokanamycin A (Compound 7)

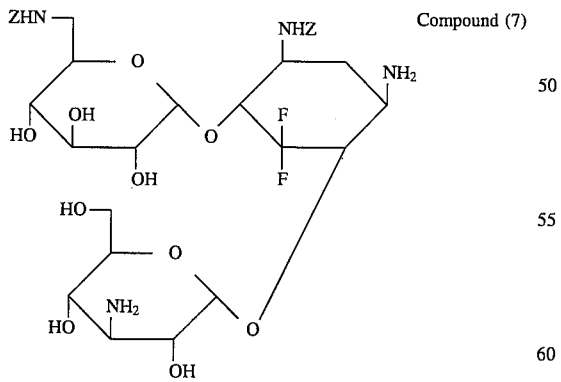

Compound (7)

The monocarbonate (87.2 mg) of the compound (6) as obtained in Example 1(c) was suspended in dry dimethylsulfoxide (0.9 ml), to which zinc acetate dihydrate (172 mg) was added, followed by stirring at 80° C. for 1 hour. The resultant homogeneous solution was cooled to room temperature, to which N-(benzyloxycarbonyloxy)succinimide (136 mg) was added, followed by effecting the reaction at room temperature for 2 hours (for introducing benzyloxycarbonyl group as the amino-protecting group).

Ethyl ether was added to the reaction solution, the deposited precipitate was washed with ethyl ether and the resulting solid was dissolved in a mixed solvent of dioxane and water (1:1). The solution was passed through a column of "Amberlite CG-50" ($NH_4^+$-form) resin for the adsorption, and the resin column was developed gradiently with mixed solvent of water and dioxane (1:1) containing ammonia, while changing the concentration of ammonia from 0N to 0.1N. Zinc ion was not eluted and the fractions of the eluate containing the intended substance were concentrated to dryness to obtain the titled Compound (7) (96.8 mg, yield 81%).

(b) 3,6'-bis(N-benzyloxycarbonyl)-5-deoxy-5,5-difluoro-3"-N-trifluoroacetylkanamycin A (Compound 8)

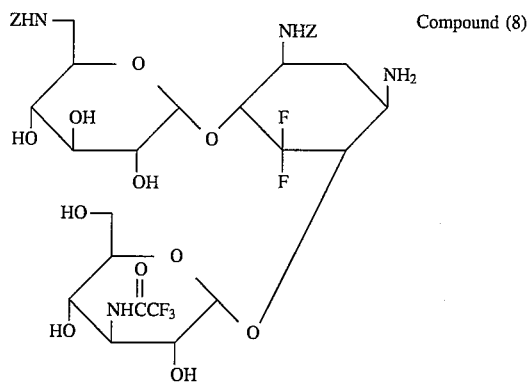

Compound (8)

The compound (7) (105 mg) as obtained in the step (a) above was dissolved in dry dimethylsulfoxide (0.5 ml) to which ethyl trifluoroacete (0.02 ml) was added, followed by effecting the reaction at room temperature for 1 hour (for selective trifluoroacetylation of 3"-OH group). Ethyl ether was added to the reaction solution and the deposited precipitate was washed with ethyl ether to obtain the titled Compound (8) (117 mg).

Example 2

(a) Preparation of 3,6'-bis(N-benzyloxycarbonyl)-1-N-[(S)-4-benzyloxycarbonylamino-2-hydroxybutyryl]-5-deoxy-5,5-difluoro-3"-N-trifluoroacetylkanamycin A (Compound 9)

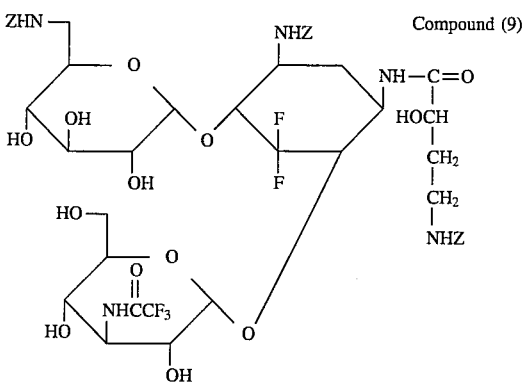

Compound (9)

The compound (8) (112 mg) as obtained in Referential Example 2(b) was dissolved in a mixed solvent (3.4 ml) of tetrahydrofuran and water (1:1). The resulting solution was mixed with sodium carbonate (11 mg) and then with the N-hydroxysuccinimide ester (26.5 mg) of (S)-4-benzyloxycarbonylamino-2-hydroxybutyric acid dissolved in tetrahydrofuran (1.7 ml). After reacting for 2 hours, 4 hours and 6 hours at room temperature, N-hydroxysuccinimide ester of (S)-4-benzyloxycarbonylamino-2-hydroxybutyric acid (18 mg) was further added at each time. After effecting the reaction at room temperature for 7 hours (for the (S)-4-protected-amino-2-hydroxybutyrylation of the amino group at 1-position), the reaction solution was concentrated and the residue was washed with water, dried and washed with ethyl ether and dried to obtain the titled Compound (9) (135 mg).

(b) Preparation of 1-N-[(S)-4-amino-2-hydroxybutyryl]-5-deoxy-5,5-difluorokanamycin A (Compound 10)

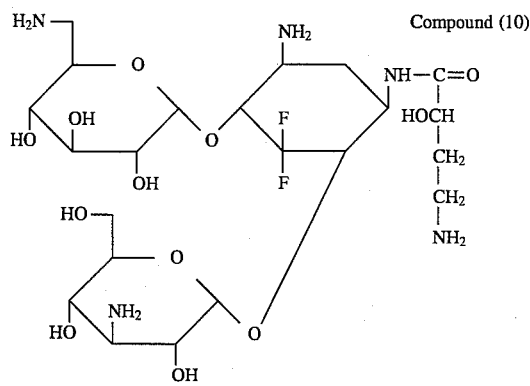

Compound (10)

The compound (9) (350 mg) as obtained in the step (a) above was dissolved in a mixed solvent (25 ml) of 2N aqueous ammonia and tetrahydrofuran (4:3) (two layers were formed), followed by effecting the reaction for 1 day at 28° C. with stirring to remove the 3"-N-trifluoroacetyl group. Thereafter, the reaction solution was concentrated and the resulting solid was dissolved in a mixed solvent of dioxane (12 ml), water (2.5 ml) and acetic acid (2.5 ml). The solution so obtained was subjected to catalytic reduction in the presence of palladium black as a catalyst at room temperature for 1 hour to remove the N-benzyloxycarbonyl group. After filtration of the reaction solution, the filtrate was concentrated to obtain a solid. The solid was dissolved in water and the solution was chromatographed gradiently in a column of "CM-Sephadex C-25" as developed with aqueous ammonia, while changing the concentration of ammonia from 0N to 0.5N. Fractions of the eluate containing the intended substance were concentrated to dryness to obtain the titled Compound (10) (103 mg).

$[\alpha]_D^{20}$ +48° (c 1, water)

Referential Example 3

(a) Preparation of 1,3,6',3"-tetrakis(N-benzyloxycarbonyl)-3',4'-dideoxykanamycin A (Compound 11)

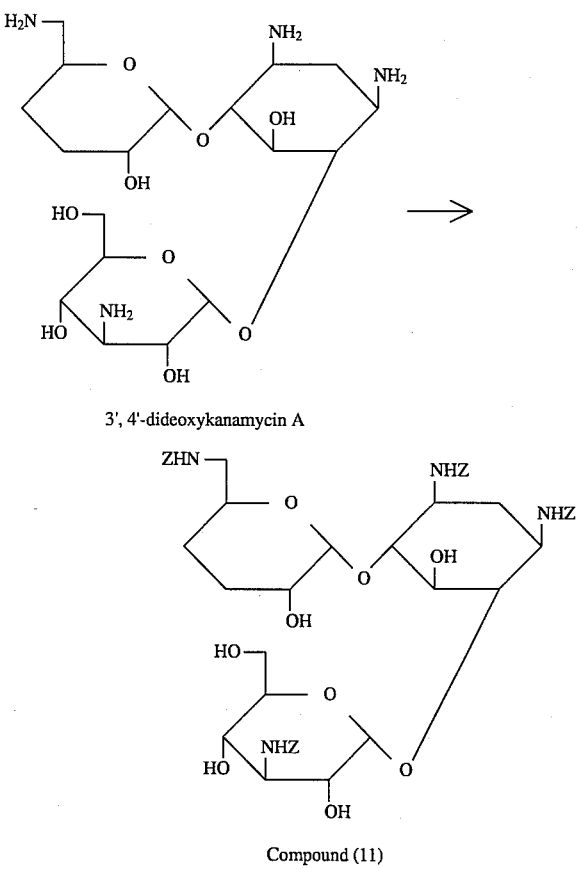

3',4'-dideoxykanamycin A

Compound (11)

3',4'-dideoxykanamycin A (527 mg) and sodium carbonate (520 mg) were added to a mixed solvent (10.5 ml) of water and acetone (1:1) to which benzyloxy chloride (0.68 ml) was added, followed by stirring under ice-cooling for 3 hours (for introducing the N-benzyloxycarbonyl group). Water (70 ml) was added to the reaction solution and the deposited solid was filtered, washed with water, dried and washed with ethyl ether and dried to obtain the titled Compound (11) (957 mg, yield 83%).

(b) Preparation of 2',2",4",6"-tetra-O-acetyl-1,3,6',3"-tetrakis(N-benzyloxycarbonyl)-3',4'-dideoxykanamycin A (Compound 12)

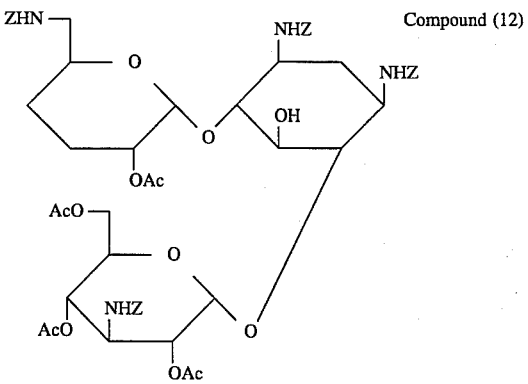

Compound (12)

The Compound (11) (803 mg) as obtained in the step (a) above was dissolved in dry pyridine (16 ml) to which acetic anhydride (1.38 ml) was added, followed by effecting the acetylation reaction overnight at room temperature. Water (1.32 ml) was added to the reaction solution, and after allowing to stand for 30 minutes, the solution was concentrated to dryness. The resulting residue was extracted with chloroform, washed successively with 10% aqueous solution of potassium hydrogen sulfate, a saturated aqueous solution of sodium hydrogen carbonate and water and then dried over anhydrous sodium sulfate. The resulting solution was concentrated to dryness to afford the titled Compound (12) (841 mg, yield 90%).

(c) Preparation of 2',2",4",6"-tetra-O-acetyl-1,3,6',3"-tetrakis(N-benzyloxycarbonyl)-5,3',4'-trideoxy-5-oxo-kanamycin A (Compound 13)

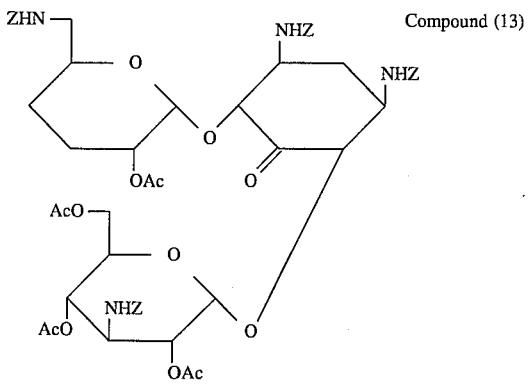

Compound (13)

The compound (12) (784 mg) as obtained in the step (b) above was dissolved in dry dimethylsulfoxide (2.35 ml) to which acetic anhydride (1.57 ml) was added, followed by effecting the reaction for 3 days at room temperature (for the oxidation of the hydroxyl group at 5-position).

The reaction solution was poured into a saturated aqueous solution (80 ml) of sodium hydrogen carbonate under ice-cooling and the solution was stirred for 3 hours. The resulting precipitate was filtered, washed with water and extracted with chloroform. The organic layer was washed successively with a saturated aqueous solution of sodium hydrogen carbonate and water and then dried over anhydrous sodium sulfate. The resulting solution was concentrated to dryness to obtain the titled Compound (13) (625 mg, 80% yield of crude product).

Example 3

(a) Preparation of 2',2",4",6"-tetra-O-acetyl-1,3,6',3"-tetrakis(N-benzyloxycarbonyl)-5,3', 4'-trideoxy-5,5-difluorokanamycin A (Compound 14)

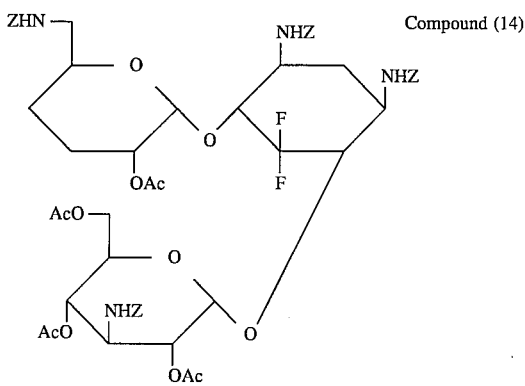

Compound (14)

The compound (13) (329 mg) as obtained in Referential Example 3(c) was dissolved in dry dichloromethane (10 ml) to which diethylaminosulfur trifluoride (0.49 ml) was added under ice-cooling, followed by effecting the reaction for 7 hours at room temperature (for the di-fluorination). The reaction solution was poured into an aqueous solution (40 ml) of sodium hydrogen carbonate under ice-cooling and the solution was stirred for 30 minutes. The dichloromethane layer was separated and concentrated to dryness. The resulting solid was isolated and purified by subjecting to chromatography on silica gel column (developer: chloroform-acetone, 9:2) to give the titled Compound (14) (137 mg, yield 41%).

(b) Preparation of 1,3,6',3"-tetrakis(N-benzyloxycarbonyl)-5,3',4'-trideoxy-5,5-difluorokanamycin A (Compound 15)

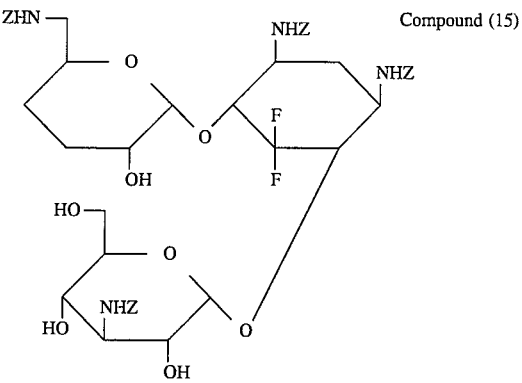

Compound (15)

The compound (14) (452 mg) as obtained in the step (a) above was dissolved in a mixed solvent of methanol (18 ml) and water (1.8 ml) to which sodium carbonate (570 mg) was added, followed by effecting the reaction for 2 hours at room temperature under vigorous stirring (for the de-acetylation). Dilute hydrochloric acid was added to the reaction solution to neutralize and the solution was concentrated to dryness. The resulting residue was washed with water and then dried to obtain the titled Compound (15) (294 mg, yield 76%).

(c) Preparation of 5,3',4'-trideoxy-5,5-difluorokanamycin A (Compound 16)

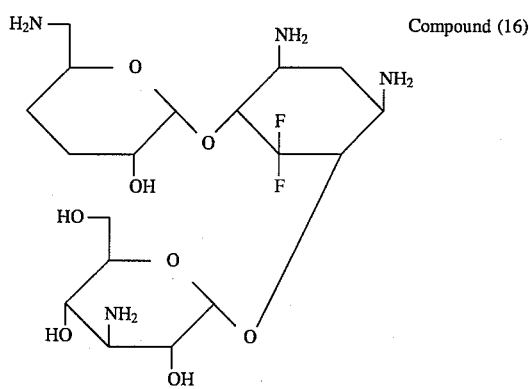

Compound (16)

The compound (15) (161 mg) as obtained in the step (b) above was dissolved in a mixed solvent (9.7 ml) of dioxane, acetic acid and water (4:1:1), followed by effecting catalytic reduction for 3 hours at room temperature in the presence of palladium black as a catalyst (for the deprotection). After filtration of the reaction solution, the filtrate was concentrated to dryness. The resulting solid was developed with aqueous ammonia, in a column of "CM-Sephadex C-25", while changing the concentration of ammonia from 0N to 0.15N. Fractions of the eluate containing the intended substance were concentrated to dryness to obtain the titled Compound (16) (47.7 mg, yield 54%, calculated as the monocarbonate monohydrate). $[\alpha]_D^{20} +130°$ (c 1, water)

Referential Example 4

Preparation of 3,6'-bis(N-benzyloxycarbonyl)-5,3',4'-trideoxy-5,5-difluorokanamycin A (Compound 17)

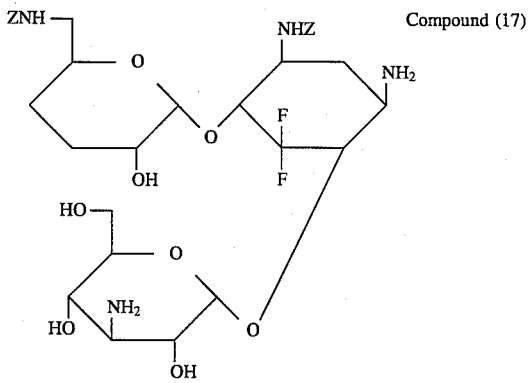

Compound (17)

The monocarbonate (121 mg) of the compound (14) as obtained in Example 3(c) above was suspended in dry dimethylsufoxide (1.2 ml) to which zinc acetate dihydrate (252 mg) was added, followed by stirring for 1 hour at 80° C. The resulting homogeneous solution was cooled to room temperature and N-(benzyloxycarbonyl)succinimide (201 mg) was added, followed by effecting the reaction for 1.5 hours at room temperature. Ethyl ether was added to the reaction solution and the deposited precipitate was washed with ethyl ether. The resulting solid was dissolved in a mixed solvent of water and dioxane (2:3) and the solution was chromatographed gradiently in "Amberlite CG-50" ($NH_4^+$-form) resin with a mixed solvent of water and dioxane (2:3) containing ammonia, while changing the concentration of ammonia from 0N to 0.1N. Zinc ions were not eluted and the fractions of the eluate containing the intended substance were concentrated to dryness to obtain the titled Compound (17) (131 mg, yield 79%).

Example 4

(a) Preparation of 1-N-[(S)-4-amino-2-hydroxybutyryl]-5,3',4'-trideoxy-5,5-difluorokanamycin A (Compound 18)

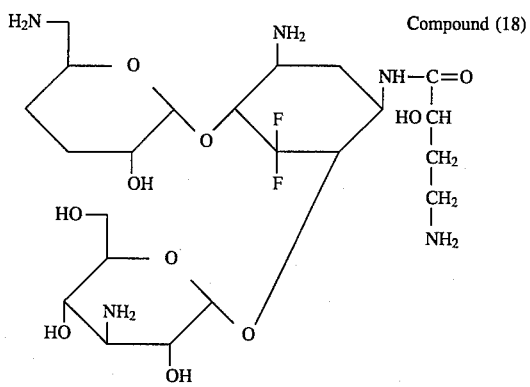

Compound (18)

3"-N-Trifluoroacetylation and 1-N-[(S)-4-benzyloxycarbonylamino-2-hydroxybutyryl]ation, de-3"-N-trifluoroacetylation and de-tris-N-benzyloxycarbonylation of the Compound (17) as obtained in the Referential Example 4 were effected according to the same manner as in Referential Example 2(b) and Example 2(a) and (b) to afford the titled Compound (18).

$[\alpha]_D^{20} +105°$ (c 1, water)

Referential Example 5

(a) Preparation of 3',4',2",4",6"-penta-O-acetyl-1,3,2',6',3"-pentakis(N-benzyloxycarbonyl)kanamycin B (Compound 19)

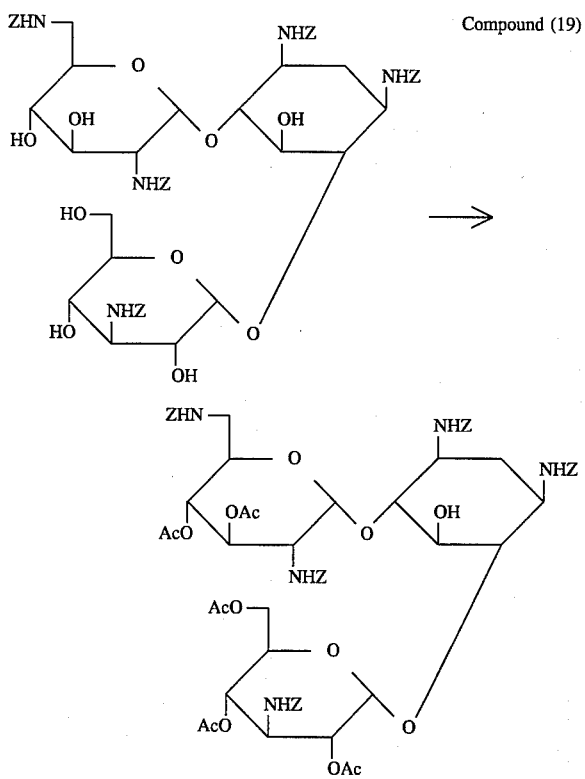

Compound (19)

1,3,2',6',3"-pentakis(N-benzyloxycarbonyl)kanamycin B (1.05 g) was dissolved in dry pyridine (21 ml) to which acetic anhydride (1.72 ml) was added, followed by effecting the O-acetylation reaction overnight at room temperature.

Water (1.64 ml) was added to the reaction solution, the solution was left to stand for 30 minutes at room temperature and then concentrated to dryness. The residue was extracted with chloroform and the chloroform extract was washed successively with 10% aqueous solution of potassium hydrogen sulfate, a saturated aqueous solution of sodium hydrogen carbonate and water and then dried over anhydrous sodium sulfate. The resulting solution was concentrated to dryness to obtain the titled Compound (19) (1.20 g, yield 97%).

(b) Preparation of 3',4',2",4",6"-penta-O-acetyl-1,3,2',6', 3"-pentakis(N-benzyloxycarbonyl)-5-deoxy-5-oxo-kanamycin B (Compound 20)

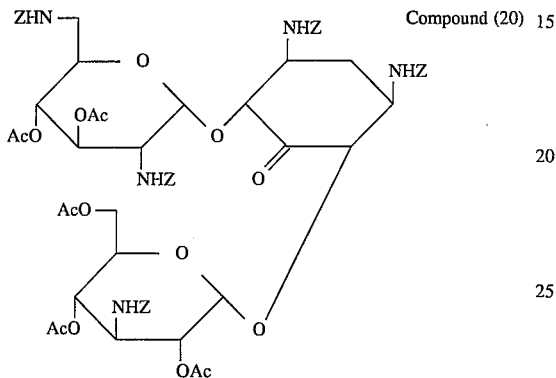

The Compound (19) (1.10 g) as obtained in the step (a) above was dissolved in dry dimethylsulfoxide (3.3 ml) to which acetic anhydride (2.2 ml) was added, followed by effecting the reaction for 4 days at room temperature (for oxidation of the hydroxyl group at 5-position). The reaction solution was poured in small portions into a saturated aqueous solution of sodium hydrogen carbonate (110 ml) under ice-cooling and with stirring, and the solution was stirred for 2.5 hours under ice-cooling. The resulting precipitate was filtered and washed with water. The resulting solid was extracted with chloroform and washed successively with a saturated aqueous sodium hydrogen carbonate and water and then dried over anhydrous sodium sulfate. The resulting solution was concentrated to dryness to give the titled Compound (20) (1.03 g, yield 94%).

Example 5

(a) Preparation of 3',4',2",4",6"-penta-O-acetyl-1,3,2',6', 3"-pentakis(N-benzyloxycarbonyl)-5-deoxy-5,5-difluorokanamycin B (Compound 21)

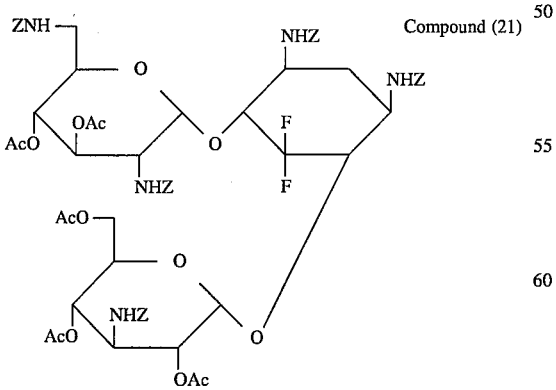

The Compound (20) (876 mg) as obtained in Referential Example 5(b) was dissolved in dry dichloromethane (26 ml) to which diethylaminosulfur trifluoride (1.1 ml) was added under ice-cooling, followed by effecting the di-fluorination reaction for 6 hours at room temperature. The reaction solution was poured into an aqueous solution (110 ml) of sodium hydrogen carbonate under ice-cooling and the solution was stirred for 30 minutes. The dichloromethane layer was separated and the aqueous layer was extracted with chloroform three times. The combined organic layer was washed successively with a saturated aqueous solution of sodium hydrogen carbonate and water and then dried over anhydrous sodium sulfate. The organic layer was concentrated to dryness. The resulting solid was isolated and purified by subjecting to chromatography on silica gel column (developer: chloroform-acetone, 9:2) to obtain the titled Compound (21) (403 mg, yield 45%).

(b) Preparation of 1,3,2',6',3"-pentakis(N-benzyloxycarbonyl)-5-deoxy-5,5-difluorokanamycin B (Compound 22)

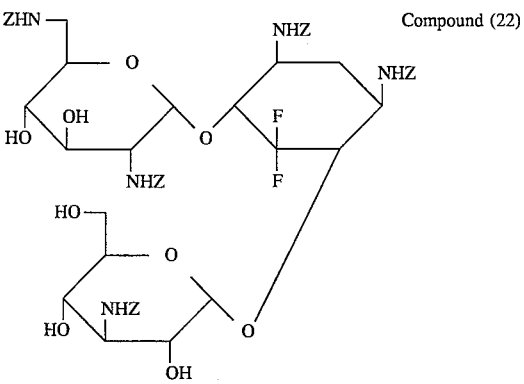

The Compound (21) (688 mg) as obtained in the step (a) above was dissolved in a mixed solvent (14 ml) of dry tetrahydrofuran and dry methanol (1:1), to which a 1N solution (0.34 ml) of sodium methoxide in methanol was added, followed by effecting the reaction for 30 minutes at room temperature (for de-acetylation). Dilute hydrochloric acid was added to the reaction solution to neutralize and the solution was concentrated to dryness. The resulting residue was washed with water to afford the titled Compound (22) (568 mg, yield 97%).

(c) Preparation of 5-deoxy-5,5-difluorokanamycin B (Compound 23)

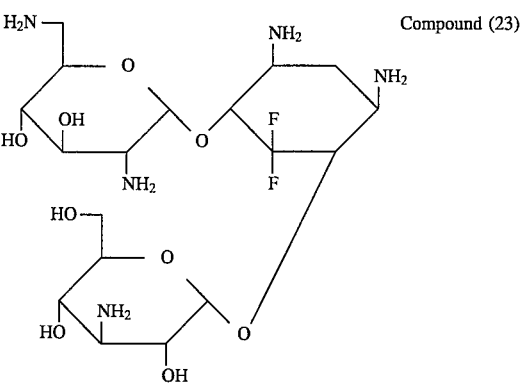

The Compound (22) (408 mg) as obtained in the step (b) above was dissolved in a mixed solvent of dioxane (14 ml), acetic acid (2.8 ml) and water (3.5 ml), followed by effecting the catalytic reduction for 3 hours at room temperature in the presence of palladium black as a catalyst (for the deprotection). After filtration of the reaction solution, the filtrate was concentrated to dryness. The resulting solid was chromatographed on a column of "CM-Sephadex C-25" as developed with aqueous ammonia while changing the concentration of ammonia from 0N to 0.15N. Fractions of the eluate containing the intended substance were concentrated to dryness to obtain the titled Compound (23) (131 mg, yield 65%, calculated as the monocarbonate monohydrate).

Example 6

(a) Preparation of 1-N-[(S)-4-amino-2-hydroxybutyryl]-5-deoxy-5,5-difluorokanamycin B (Compound 24)

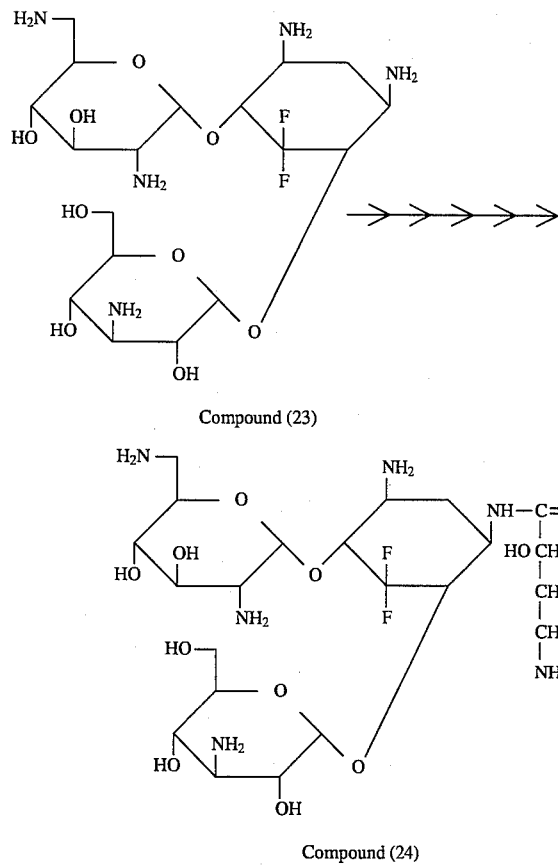

Compound (23)

Compound (24)

3,2',6'-Tris-N-benzyloxycarbonylation and 3"-N-trifluoroacetylation, 1-N-[(S)-4-benzyloxycarbonylamino-2-hydroxybutyryl]ation, de-3"-N-trifluoroacetylation and de-tetrakis-N-benzyloxycarbonylation of the Compound (23) as obtained in Example 5(c) were effected according to the same manner as in Referential Example 2(a) and (b) and also in Example 2(a) and (b) to obtain the titled Compound (24).

Referential Example 6

(a) Preparation of 1,3,2',6',3"-pentakis(N-benzyloxycarbonyl)tobramycin (Compound 25)

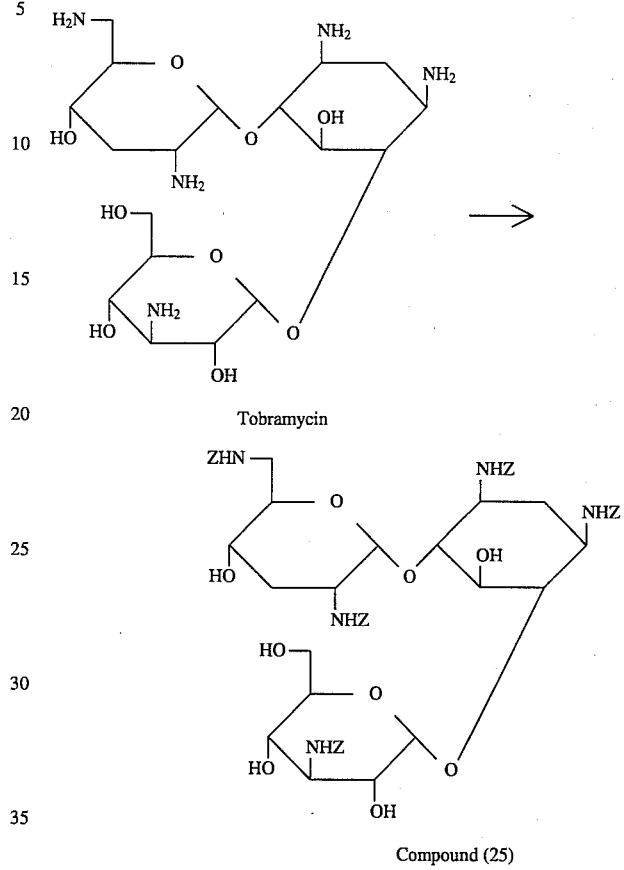

Tobramycin

Compound (25)

Tobramycin sulfate (1.29 g) was dissolved in a mixed solvent (26 ml) of water and acetone (1:1) to which sodium carbonate (1.2 g) and benzyloxycarbonyl chloride (1.13 ml) were added, followed by stirring for 3 hours under ice-cooling. Water (130 ml) was added to the reaction solution and the resulting precipitate was filtered, washed with water and dried and washed with ethyl ether to obtain the titled Compound (25) (2.00 g, yield 97%).

$[\alpha]_D^{24}$ +53° (c 2.0, pyridine)

(b) Preparation of 4',2",4",6"-tetra-O-acetyl-1,3,2',6',3"-pentakis(N-benzyloxycarbonyl)tobramycin (Compound 26)

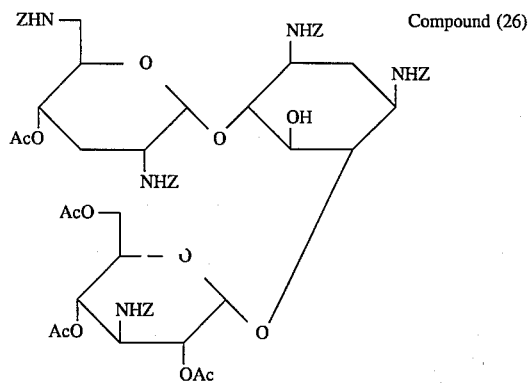

Compound (26)

The Compound (25) (2.09 g) as obtained in the step (a) above was dissolved in dry pyridine (42 ml), to which acetic anhydride (3.47 ml) was added, followed by effecting the O-acetylation overnight at room temperature.

Water (3.3 ml) was added to the reaction solution and after allowing to stand for 30 minutes, the solution was concentrated to dryness. The residue was extracted with chloroform and the extract solution was washed successively with 10% aqueous solution of potassium hydrogen sulfate, a saturated aqueous solution of sodium hydrogen carbonate and water and then dried over anhydrous sodium sulfate. The resulting solution was concentrated to dryness to obtain the titled Compound (26) (2.40 g, yield 100%).

$^1$H-NMR spectrum (in deutero-pyridine-D$_2$O): δ1.88, 2.00, 2.05, and 2.18, each 3H singlet(acetyl)

(c) Preparation of 4',2",4",6"-tetra-O-acetyl-1,3,2', 6',3"-pentakis(N-benzyloxycarbonyl)-5-deoxy-5-oxotobramycin (Compound 27)

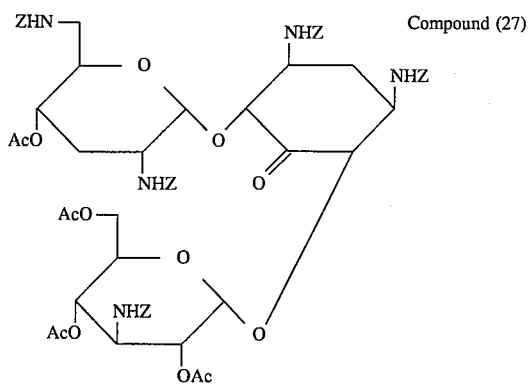

Compound (27)

Pyridinium chlorochromate (4.75 g) and powdered Molecular Sieve 3A (5.5 g) were suspended in dry dichloromethane (24 ml), to which was added a solution in dry dichloromethane (280 ml) of the Compound (26) (2.40 g) obtained in the above step (b), followed by stirring at room temperature for 3 days to oxidize the hydroxyl group at the 5-position.

The insoluble matter in the reaction solution was filtered with aid of Celite and washed with chloroform. The filtrate and the washings were combined and the resulting solution was concentrated to 200 ml and washed successively with 10% aqueous solution of potassium hydrogen sulfate and a saturated aqueous solution of sodium hydrogen carbonate. The solution was then dried over anhydrous sodium sulfate and concentrated to dryness. The resulting residue was purified by chromatography on silica gel column (developer: chloroform-acetone, 7:2) to obtain the titled Compound (27) (1.82 g, yield 76%).

[α]$_D^{24}$+65° (c 2, CHCl$_3$) $^1$H-NMR spectrum (in deutero-pyridine): δ1.85, 1.91, 1.95, and 1.99, each 3H singlet(acetyl).

Example 7

(a) Preparation of 4',2",4",6"-tetra-O-acetyl-1,3,2',6',3"-pentakis(N-benzyloxycarbonyl)-5-deoxy-5,5-difluorotobramycin (Compound 28)

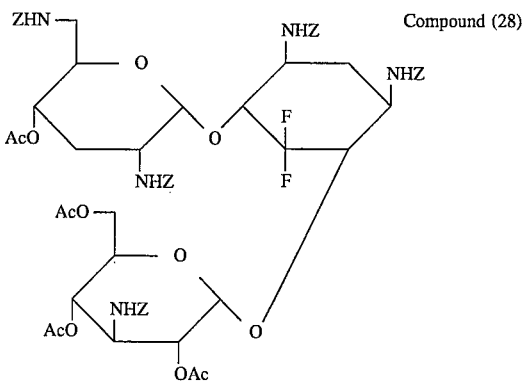

Compound (28)

The Compound (27) (1.69 g) as obtained in Referential Example 6(c) was dissolved in dry dichloromethane (50 ml) to which diethylaminosulfur trifluoride (2.06 ml) was added under ice-cooling, followed by effecting the reaction for 8 hours at room temperature. The reaction solution was poured into a saturated aqueous solution (200 ml) of sodium hydrogen carbonate under ice-cooling and the solution was stirred for 30 minutes. The dichloromethane layer was when separated, washed with a saturated aqueous solution of sodium hydrogen carbonate and then dried over anhydrous sodium sulfate. The solution was concentrated to dryness and the resulting residue was purified by chromatography on silica gel column (developer: chloroform-acetone, 4:1) to afford the titled Compound (28) (1.13 g, yield 66%).

[α]$_D^{24}$+67° (c 2, CHCl$_3$). $^1$H-NMR spectrum (in deutero-pyridine): δ1.79(s,3H), 1.97(s,6H), 2.00(s,3H), each, methyl of acetyl group.

$^{19}$F-NMR spectrum (in deutero-pyridine, CFCl$_3$ internal standard): δ –110.3(d, J$_{F,F}$=250 Hz) and –129.5(dt, J$_{F,H-4}$= J$_{F,H-6}$=19 Hz)

(b) Preparation of 1,3,2',6', 3"-pentakis(N-benzyloxycarbonyl-5-deoxy-5,5-difluorotobramycin (Compound 29)

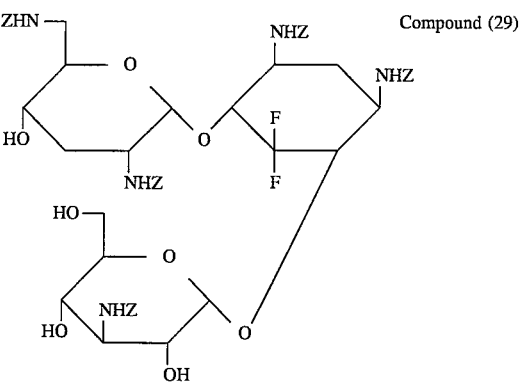

Compound (29)

The Compound (28) (400 mg) as obtained in the step (a) above was dissolved in a mixed solvent of dry tetrahydrofuran (4 ml) and dry methanol (3.8 ml) to which a 1N solution (0.2 ml) of sodium methoxide in methanol was added, followed by effecting the reaction for 40 minutes at room temperature. Dilute hydrochloric acid was added to the reaction solution to neutralize and the solution was concentrated to dryness. The resulting residue was washed with water to obtain the titled Compound (29) (347 mg, yield 99%).

[α]$_D^{23}$+70° (c 2, pyridine)

$^{19}$F-NMR spectrum (in deutero-pyridine, CFCl$_3$ internal standard): δ –111.1(d, J$_{F,F}$=250 Hz) and –129.0 (dt, J$_{F,H-4}$= J$_{F,H-6}$=19 Hz)

(c) Preparation of 5-deoxy-5,5-difluorotobramycin (Compound 30)

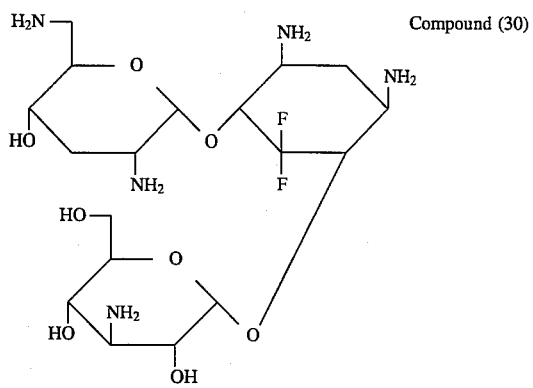

Compound (30)

The Compound (29) (942 mg) as obtained in the step (b) above was dissolved in a mixed solvent of dioxane (32 ml), acetic acid (8.1 ml) and water (6.5 ml), followed by effecting the catalytic reduction for 2 hours at room temperature in the presence of palladium black as a catalyst. After filtration of the reaction solution, the filtrate was concentrated to dryness. The resulting solid was dissolved in water and was chromatographed in a column of "CM-Sephadex C-25" developed with aqueous ammonia, while changing the concentration of ammonia from 0N to 0.15N. Fractions of the eluate containing the intended substance were concentrated to dryness to obtain the titled Compound (30) (409 mg, yield 89%, calculated as the monocarbonate monohydrate).

$[\alpha]_D^{22}$ +134° (c 1, H$_2$O)

$^{19}$F-NMR spectrum (in 20% ND$_3$/D$_2$O; CCl$_3$F external standard): δ –110.6 (d, $J_{F,F}$=246 Hz) and –128.6 (d, $J_{F,H-4}$=$J_{F,H-6}$=21 Hz)

Referential Example 7

(a) Preparation of 3,2',6'-tris(N-benzyloxycarbonyl)-5-deoxy-5,5-difluorotobramycin (Compound 31)

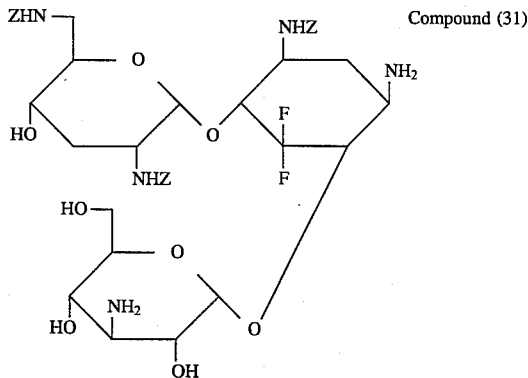

Compound (31)

In dry dimethylsulfoxide (3.4 ml) was suspended the monocarbonate (335 mg) of 5-deoxy-5,5-difluorotobramycin, namely Compound (30) as obtained in Example 6(c), followed by addition of zinc acetate dihydrate (678 mg). The resultant mixture was stirred at 80° C. for 1 hour and the resulting homogeneous solution was cooled to room temperature. N-(benzyloxycarbonyloxy)succinimide (558 mg) was added portionwise to said solution which was then subjected to the reaction for 1 hour at room temperature.

Ethyl ether was added to the reaction solution, and a precipitate as deposited was washed with ethyl ether. The solid obtained was repeatedly washed with 3N aqueous ammonia to remove the zinc cation therefrom. The resulting product was washed with water and then dried to give 537 mg of the titled Compound (31).

(b) Preparation of 3,2',6'-tris(N-benzyloxycarbonyl)-5-deoxy-5,5-difluoro-3''-N-trifluoroacetyltobramycin (Compound 32)

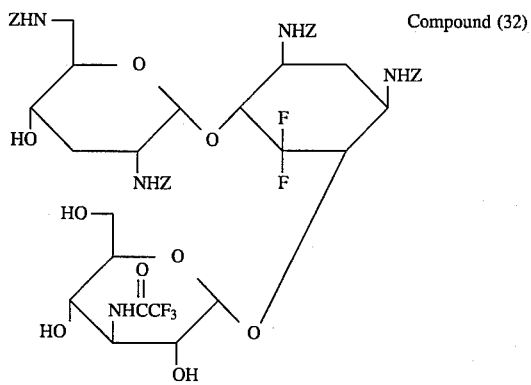

Compound (32)

Compound (31) (537 mg) as obtained in the step (a) above was dissolved in dry dimethylsulfoxide (2.7 ml), followed by addition of ethyl trifluoroacetate (0.094 ml). The reaction was made at room temperature for 1 hour. Ethyl ether was added to the reaction solution, and the precipitate as obtained was washed repeatedly with ethyl ether and dried, thereby affording the titled Compound (32) as a solid (596 mg).

Example 8

(a) Preparation of 3,2',6'-tris(N-benzyloxycarbonyl)-1-N-[(S)-4-benzyloxycarbonylamino-2-hydroxybutyryl]-5-deoxy-5,5-difluoro-3''-N-trifluoroacetyltobramycin (Compound 33)

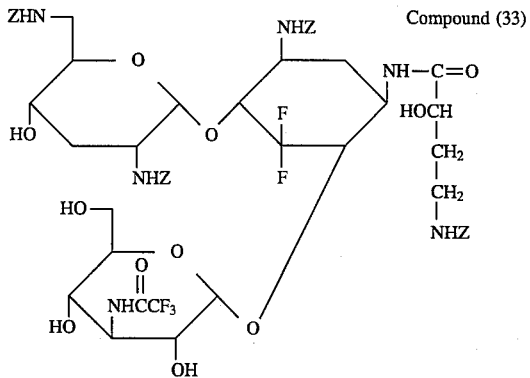

Compound (33)

Compound (32) (62.1 mg) as obtained in Referential Example 7(b) was dissolved in a mixed solvent (1.9 ml) of tetrahydrofuran and water (1:1). The resulting solution was mixed with sodium carbonate (5.3 mg) and then with a solution of N-hydroxysuccinimide ester (26.5 mg) of (S)-4-benzyloxycarbonylamino-2-hydroxybutyric acid in tetrahydrofuran (1 ml), followed by further addition of N-hydroxysuccinimide ester (6.6 mg) of (S)-4-benzyloxycarbonylamino-2-hydroxybutyric acid at room temperature each 2 hours, 4 hours and 5 hours later. The reaction was conducted at room temperature for 7 hours. Thereafter, the reaction solution was concentrated to a small volume and the residue was washed with water. After drying, the residue was washed with ethyl ether and dried to afford the titled Compound (33) as a solid (68.3 g).

(b) Preparation of 1-N-[(S)-4-amino-2-hydroxybutyryl]-5-deoxy-5,5-difluorotobramycin (Compound 34)

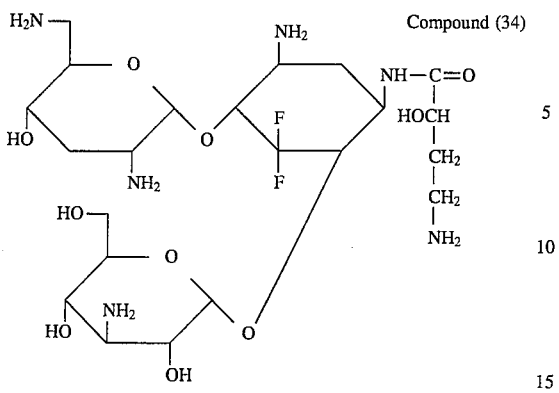

Compound (34)

Compound (33) (68.3 mg) as obtained in the step (a) above was dissolved in a (4:3) mixed solvent (3.4 ml) of 2N aqueous ammonia and tetrahydrofuran to afford a mixture comprising two layers. The reaction mixture was agitated overnight at 28° C. to remove the 3"-N-trifluoroacetyl group from Compound (33). Thereafter, the reaction solution was concentrated to dryness and the resulting solid residue was dissolved in a mixed solvent of dioxane (2 ml), water (0.5 ml) and acetic acid (0.4 ml). The resulting solution was subjected to catalytic reduction with hydrogen gas at room temperature for 1 hour in the presence of palladium black as a catalyst to remove the N-benzyloxycarbonyl groups from Compound (33). The reaction solution was filtered and the filtrate was concentrated to dryness. The resulting solid was dissolved in water and was chromatographed gradiently in a column of "CM-Sephadex C-25" as developed with aqueous ammonia as an eluent while changing the concentration of ammonia from 0N to 0.5N. Fractions of the eluate containing the intended compound were collected and concentrated to dryness, giving the titled Compound (34) as a solid (21.6 mg).

Specific rotation: $[\alpha]_D^{23} +89°$ (c 3, $H_2O$)

$^{19}$F-NMR Spectrum (in 20% $ND_3$-$D_2O$; $CCl_3F$ external standard): $\delta$–110.3(d, $J_{F,F}$=247 Hz) and –129.5(dt, $J_{F,H-4}$ =$J_{FH-6}$=20 Hz)

Referential Example 8

(a) Preparation of 1,3,2',6',3"-pentakis(N-benzyloxycarbonyl)-3',4'-dideoxykanamycin B (Compound 35)

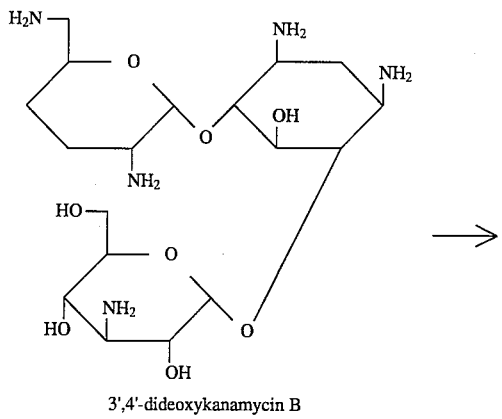

3',4'-dideoxykanamycin B

→

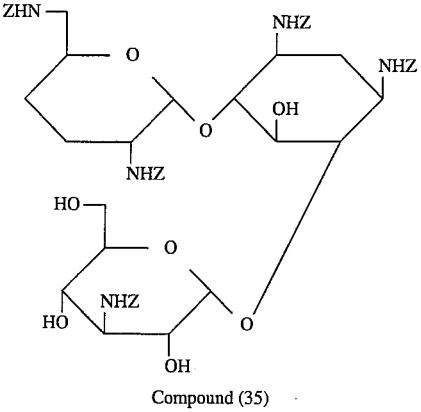

Compound (35)

A mixture of 3',4'-dideoxykanamycin B (1.01 g) and sodium carbonate (1.2 g) was dissolved in a mixed solvent (20 ml) of water and acetone (1:1), followed by addition of benzyloxycarbonyl chloride (1.61 ml) under ice-cooling and stirring.

One hour later, the reaction mixture was warmed to room temperature, followed by addition of water (130 ml). The resulting precipitate was collected by filtration, washed with water and then dried under reduced pressure. The precipitate was further washed with ethyl ether and dried to afford the titled Compound (35) as a solid (2.35 g). Yield: 94%

(b) Preparation of 2",4",6"-tri-O-acetyl-1,3,2',6',3"-pentakis(N-benzyloxycarbonyl)-3',4'-dideoxykanamycin B (Compound 36)

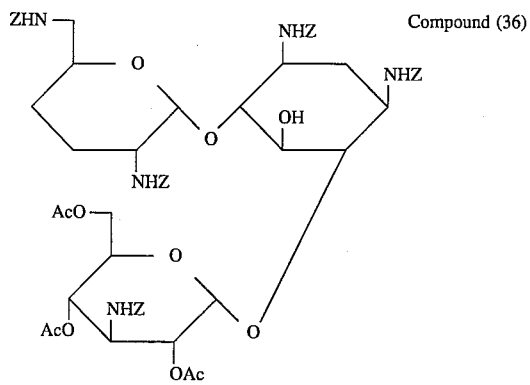

Compound (36)

Compound (35) (1.73 g) as obtained in the step (a) above was dissolved in dry pyridine (35 ml), to which acetic anhydride (3 ml) was added to conduct the reaction overnight at room temperature. The reaction solution was mixed with water (2.9 ml) under ice-cooling, allowed to stand at room temperature for 30 minutes and then concentrated to dryness under reduced pressure. The resulting residue was extracted with chloroform and the extract solution was washed successively with a 10% aqueous solution of potassium hydrogen sulfate, a saturated aqueous solution of sodium hydrogen carbonate and water and dried over anhydrous sodium sulfate. This solution was concentrated to dryness to obtain a solid (1.95 g). The resultant solid was purified by column chromatography on silica gel as developed with a mixed solvent of chloroform and ethanol (30:1) as eluent to afford the titled Compound (36) as a solid (1.79 g). Yield: 93%

(c) Preparation of 2",4",6"-tri-O-acetyl-1,3,2',6',3"-pentakis (N-benzyloxycarbonyl)-5,3',4'-trideoxy-5-oxo-kanamycin B (compound 37)

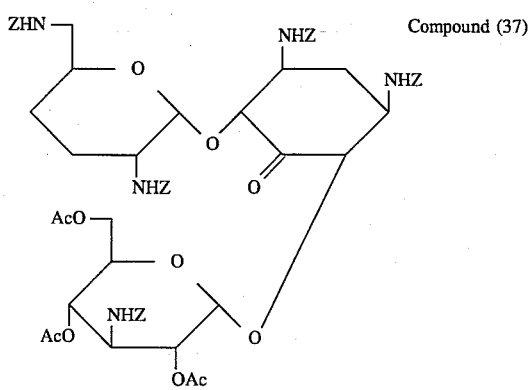

Compound (37)

Compound (36) (1.60 g) as obtained in the step (b) above was dissolved in dry dimethylsulfoxide (4.8 ml), followed by addition of acetic anhydride (3.2 ml). The reaction was conducted at room temperature for a period of 3 days. The reaction solution was added portionwise to a saturated aqueous solution of sodium hydrogen carbonate (160 ml) and the resulting precipitate was filtered, washed with water and dried. The solid so obtained was then purified by column chromatography on silica gel as developed with a mixed solvent of chloroform and ethanol (30:1) as eluent to give the titled Compound (37) as a solid (1.18 g). Yield: 74[{]jf44b

Example 9

(a) Preparation of 2",4",6"-tri-O-acetyl-1,3,2',6'3"-pentakis(N-benzyloxycarbonyl)-5,3',4'-trideoxy-5,5-difluorokanamycin B (Compound 38)

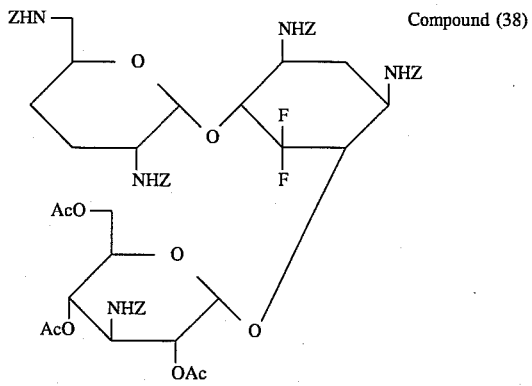

Compound (38)

Compound (37) (264 mg) as obtained in Referential Example 8(c) was dissolved in dry dichloromethane (7.9 ml), followed by addition of diethylaminosulfur trifluoride (0.36 ml) under ice-cooling. The reaction was made at room temperature for a period of 5 hours. The reaction solution was then poured into a saturated aqueous solution of sodium hydrogen carbonate (35 ml) under ice-cooling and stirring and maintained for 30 minutes with stirring. The dichloromethane layer obtained was separated from the resulting reaction solution and the aqueous layer was extracted three times with chloroform. The chloroform extract was combined with the dichloromethane layer and the combined solution was washed successively with a saturated aqueous solution of sodium hydrogen carbonate and water, and dried over anhydrous sodium sulfate. The dried solution was concentrated to dryness and the resulting solid was subjected to column chromatography on silica gel as developed with a mixed solvent of chloroform and acetone (9:2) as eluent to conduct the separation and purification of the reaction product, thereby affording the titled Compound (38) as a solid (130 mg). Yield: 49%

$^1$H-NMR Spectrum (in deutero-chloroform): δ1.79, 1.88, 1.99 (each singlet, 3H) (methyl portion of acetyl group), $^{19}$F-NMR Spectrum (in deutero-chloroform; CCl$_3$F internal standard); δ–110.4 (broad, doublet, J$_{F,F}$=247 Hz), –129.6 (broad, doublet)

(b) Preparation of 1,3,2',6',3"-pentakis (N-benzyloxycarbonyl)-5,3',4'-trideoxy-5,5-difluorokanamycin B (Compound 39)

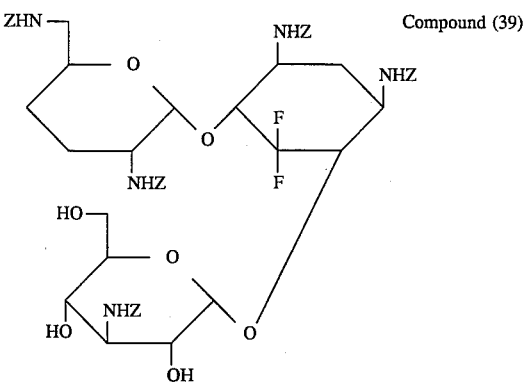

Compound (39)

Compound (38) (129 mg) as obtained in the step (a) above was dissolved in a mixed solvent of dry tetrahydrofuran (1.3 ml) and anhydrous methanol (1.3 ml), to which a methanolic solution (0.065 ml) of 1N sodium methoxide was added, followed by effecting the de-acetylation reaction at room temperature for 30 minutes. The reaction solution was neutralized by addition of dilute hydrochloric acid and concentrated to dryness. The residue obtained was washed with water and dried so that there was afforded the titled Compound (39) as a solid (116 mg). The yield was stoichiometric.

$^{19}$F-NMR Spectrum (in deutero-pyridine, CCl$_3$F internal standard): δ–110.9 (doublet, J$_{F,F}$=250 Hz), δ–129.0 (broad, double triplet)

(c) Preparation of 5,3',4'-trideoxy-5,5-difluorokanamycin B (Compound 40)

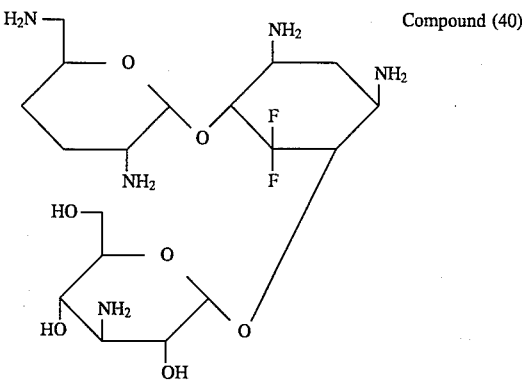

Compound (40)

Compound (39) (2.55 g) as obtained in the step (b) above was dissolved in a mixed solvent of dioxane (88 ml), acetic acid (17 ml) and water (22 ml), and the resulting solution was subjected to catalytic reduction at room temperature for 4 hours in the presence of palladium black as a catalyst. The reaction solution was filtered and the filtrate was concentrated to dryness to give a solid. The solid was dissolved in water and the resulting solution was passed through a column of "CM-Sephadex C-25" which was then eluted gradiently with aqueous ammonia while changing the concentration of ammonia from 0N to 0.15N. The active fractions of the eluate containing the intended compound were combined and concentrated to dryness to afford the titled Compound (40) as a solid (953 mg) (Yield: 77%, calculated as the monocarbonate-monohydrate).

Specific rotation: $[\alpha]_D^{21}+144°$ (c 2.0, $H_2O$)

$^{19}$F-NMR Spectrum (in 20% aqueous deutero-ammonia, $CCl_3F$ internal standard): δ–110.0(d, $J_{F,F}$=246 Hz) and –128.8(dt, $J_{F,H-4}$ =$J_{F,H-6}$=21 Hz)

Referential Example 9

(a) Preparation of 3,2',6'-tris(N-benzyloxycarbonyl)-5,3', 4'-trideoxy-5,5-difluorokanamycin B (Compound 41)

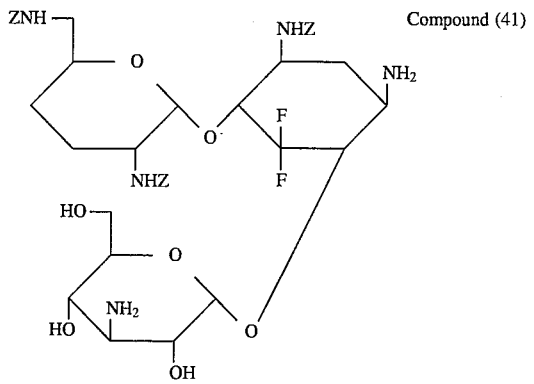

In dry dimethylsulfoxide (8.3 ml) was suspended the monocarbonate (830 mg) of 5,3',4'-trideoxy-5,5-difluorokanamycin B, namely Compound (40) obtained in Example 9(c), followed by addition of zinc acetate dihydrate (1.75 g). The resultant mixture was stirred at 80° C. for 1 hour and the resulting homogeneous solution was cooled to room temperature, followed by addition in four portions of N-(benzyloxycarbonyloxy)succinimide (1.39 g) to said solution. The reaction mixture was subjected to the reaction for 1 hour at room temperature.

Ethyl ether was added to the reaction solution and a precipitated solid obtained was repeatedly washed with 3N aqueous ammonia to remove the zinc cation from the reaction product. The resulting solid product was washed with water and dried to give the titled Compound (41) as a solid (1.36 g).

(b) Preparation of 3,2',6'-tris(N-benzyloxycarbonyl)-5,3', 4'-trideoxy-5,5-difluoro-3"-N-trifluoroacetylkanamycin B (Compound 42)

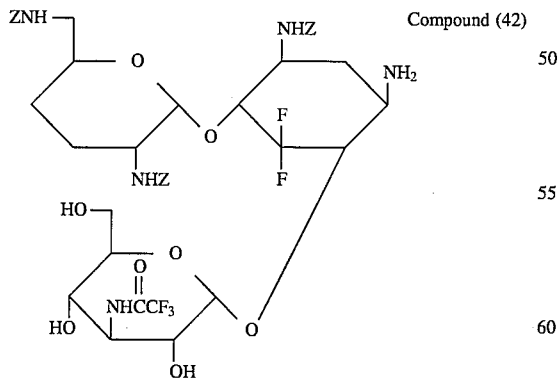

Compound (41) (1.36 g) as obtained in the step (a) above was dissolved in dry dimethylsulfoxide (6.8 ml), followed by addition of ethyl trifluoroacetate (0.24 ml). The reaction was conducted at room temperature for 1 hour. Ethyl ether was added to the reaction solution, and the precipitate obtained was washed repeatedly with ethyl ether and dried, thereby affording the titled compound (42) as a solid (1.50 g).

Example 10

(a) Preparaion of 3,2',6'-tris(N-benzyloxycarbonyl)-1-N-[(S)-4-benzyloxycarbonylamino-2-hydroxybutyryl]-5, 3',4'-trideoxy-5,5-difluoro-3"-N-trifluoroacetylkanamycin B (Compound 43)

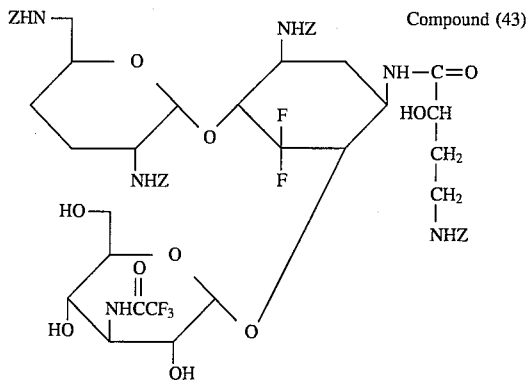

Compound (42)(1.5 g) as obtained in Referential Example 9(b) above was dissolved in a mixed solvent (45 ml) of tetrahydrofuran and water (1:1), followed by addition of sodium carbonate (130 mg). The resulting solution was then mixed with a solution of the N-hydroxysuccinimide ester (650 mg) of (S)-4-benzyloxycarbonylamino-2-hydroxybutyric acid in tetrahydrofuran (23 ml). To the reaction mixture were added successively the N-hydroxysuccinimide ester (218 mg) of (S)-4-benzyloxycarbonylamino-2-hydroxybutyric acid and sodium carbonate (66 mg) at room temperature each 2 hours, 4 hours, 6 hours and 8 hours later. The reaction was conducted at room temperature for 9 hours. Thereafter, the reaction solution was concentrated to a small volume and the resulting residue was washed with water. After drying, the residue was washed with ethyl ether and dried to give the titled Compound (43) as a solid (1.77 g).

(b) Preparation of 1-N-[(S)-4-amino-2-hydroxybutyryl]-5,3',4'-trideoxy-5,5-difluorokanamycin B (Compound 44)

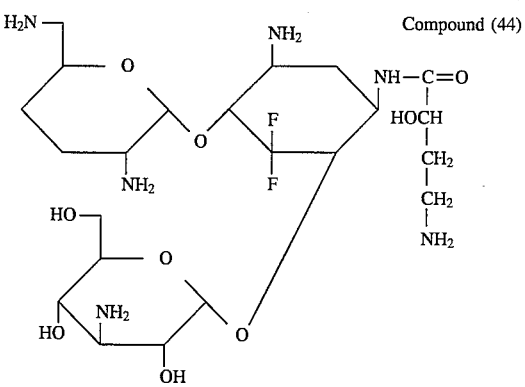

Compound (43) (1.77 g) as obtained in the step (a) above was suspended in a mixed solvent (124 ml) of 2N aqueous ammonia and tetrahydrofuran (4:3), followed by effecting the reaction at room temperature for 4 days with stirring to remove the 3"-N-trifluoroacetyl group from Compound (43). Thereafter, the reaction solution was concentrated to dryness and the resulting solid was dissolved in a mixed solvent of dioxane (63 ml), acetic acid (13ml) and water (16 ml). The resulting solution was subjected to catalytic reduction at room temperature for 3 hours in the presence of palladium black as a catalyst to remove the N-benzyloxycarbonyl groups from Compound (43).

The reaction solution obtained was filtered and the filtrate was concentrated to dryness to give a solid. The solid was dissolved in water and the solution was passed through a column of "CM-Sephadex C-25" which was then developed gradiently with aqueous ammonia while changing the concentration of ammonia from 0N to 0.5N. Fractions of the eluate containing the intended compound were combined and concentrated to dryness to afford the titled Compound (44) as a solid (612 mg).

Specific rotation: $[\alpha]_D^{21} +92°$ (c 3.0, $H_2O$)

$^{19}$F-NMR Spectrum (in 20% $ND_3$-$D_2O$, $CCl_3F$ external standard): $\delta$ –110.4(d, $J_{F,F}$=247 Hz) and –129.6(dt, $J_{F,H-4}$ =$J_{F,H-6}$=~19 Hz)

Referential Example 10

(a) Preparation of 1,3,2',6',3"-pentakis(N-benzyloxycarbonyl)-4'-deoxykanamycin B (Compound 45)

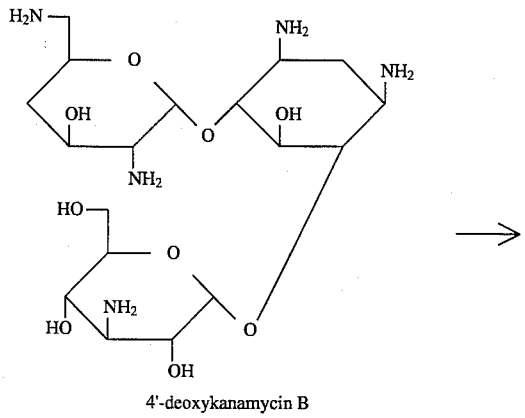

4'-deoxykanamycin B

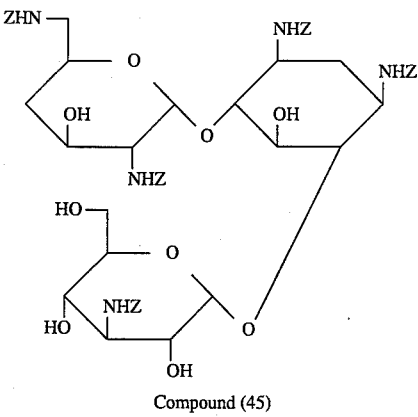

Compound (45)

4'-Deoxykanamycin B (821 mg) was dissolved in water (8.2 ml), in which sodium carbonate (950 mg) was then added and dissolved. To this solution was added acetone (8.2 ml), followed by addition of benzyloxycarbonyl chloride (1.3 ml) under ice-cooling and stirring. The reaction was conducted for 3 hours under ice-cooling and stirring.

The reaction solution was warmed to room temperature and admixed with water (100 ml). The precipitate thus formed was filtered, washed with water and dried, and subsequently the resultant residue was washed with ethyl ether and dried to give the titled Compound (45) as a solid (1.76 g). Yield: 88%

(b) Preparation of 3',2",4",6"-tetra-O-acetyl-1,3,2',6',3"-pentakis(N-benzyloxycarbonyl)-4'-deoxykanamycin B (Compound 46)

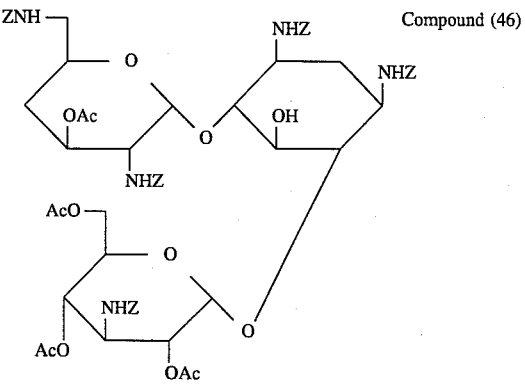

Compound (45) (1.63 g) as obtained in the step (a) above was dissolved in dry pyridine (33 ml), followed by addition of acetic anhydride (2.4 ml). The O-acetylation reaction was made overnight at room temperature. Under ice-cooling, the reaction solution was admixed with water (2.3 ml), allowed to stand at room temperature for 30 minutes and then concentrated to dryness. The resulting residue was extracted with chloroform, and the extract solution was successively washed with a 10% aqueous solution of potassium hydrogen sulfate, a saturated aqueous solution of sodium hydrogen carbonate and water and dried over anhydrous sodium sulfate. The solution obtained was concentrated to dryness, thereby affording the titled Compound (46) as a solid (1.70 g). Yield: 91%

(c) Preparation of 3',2",4",6"-tetra-O-acetyl-1,3,2',6',3"-pentakis(N-benzyloxycarbonyl)-5,4'-dideoxy-5-oxo-kanamycin B (Compound 47)

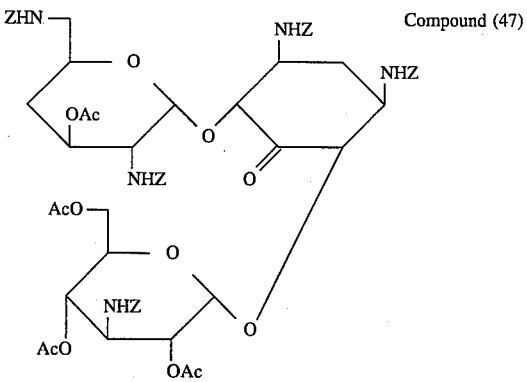

Compound (46) (1.54 g) as obtained in the step (b) above was dissolved in dry dimethylsulfoxide (4.6 ml) and the resultant solution was admixed with acetic anhydride (3.1 ml) to effect the reaction at room temperature for 3 days (for the oxidation of 5-OH group). The reaction solution obtained was poured with stirring into an ice-cooled saturated aqueous solution of sodium hydrogen carbonate (150 ml) and maintained further for 3 hours under agitation. A solid precipitated was filtered and washed with water. The solid was extracted with chloroform, and the resultant solution in chloroform was successively washed with a saturated aqueous solution of sodium hydrogen carbonate and water and then dried over anhydrous sodium sulfate. The solution was concentrated to dryness to give the titled Compound (47) as a solid (1.38 g). Yield: 90[{]jf44b

Example 11

(a) Preparation of 3',2",4",6"-tetra-O-acetyl-1,3,2',6',3"-pentakis(N-benzyloxycarbonyl)-5,4'-di-difluorokanamycin B (Compound 48)

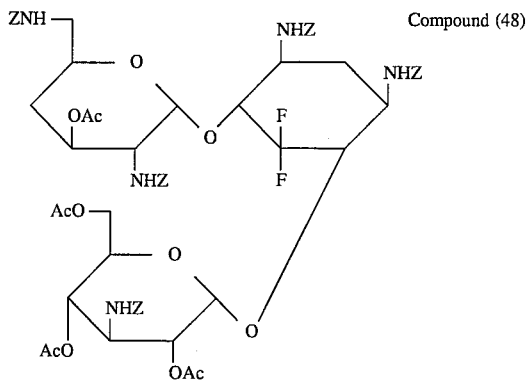

Compound (47) (993 mg) as obtained in Referential Example 10(c) was dissolved in dry dichloromethane (30 ml), followed by addition of diethylaminosulfur trifluoride (1.31 ml) under ice-cooling to conduct the reaction at room temperature for 5 hours. The reaction solution was poured with stirring into an ice-cooled saturated aqueous solution of sodium hydrogen carbonate (110 ml) and maintained for 30 minutes with stirring. The resulting dichloromethane layer was separated from the reaction solution and concentrated to dryness to give a solid. The solid obtained was subjected to column chromatography on silica gel as eluted with a mixed eluent of chloroform and acetone (9:2) to conduct the separation and purification of the intended compound, thereby affording the titled Compound (48) as a solid (414 mg). Yield: 41%

(b) Preparation of 1,3,2',6',3"-pentakis(N-benzyloxycarbonyl)-5,4'-dideoxy-5,5-difluorokanamycin B (Compound

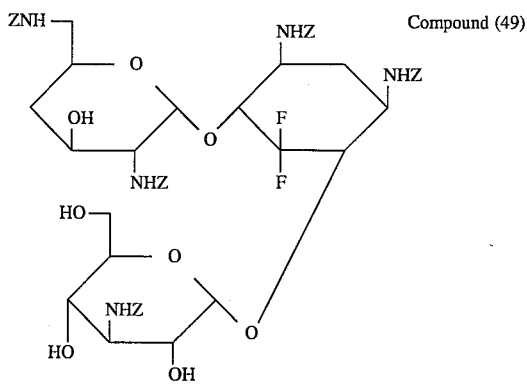

Compound (48) (307 mg) as obtained in the step (a) above was dissolved in a mixed solvent (6 ml) of dry tetrahydrofuran and anhydrous methanol (1:1), followed by addition of a methanolic solution (0.15 ml) of 1N sodium methoxide to effect the de-acetylation reaction at room temperature for 30 minutes.

The reaction solution was neutralized by addition of dilute hydrochloric acid and concentrated to dryness. The resultant residue was washed with water and dried to give the titled Compound (49) as a solid (265 mg). Yield: 99%

(c) Preparation of 5,4'-dideoxy-5,5-difluorokanamycin B (Compound 50)

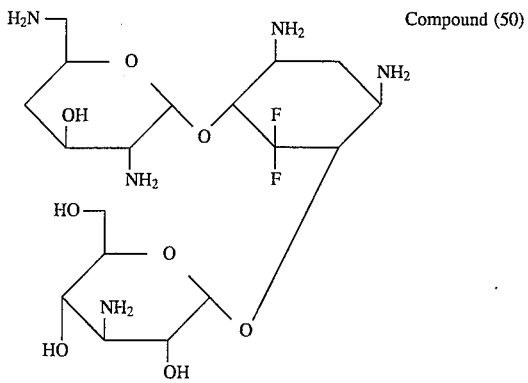

Compound (49) (244 mg) as obtained in the step (b) above was dissolved in a mixed solvent of dioxane (8.4 ml), acetic acid (1.7 ml) and water (2 ml) and the resultant solution was subjected to catalytic reduction in the presence of palladium black as a catalyst at room temperature for 2 hours. The reaction solution was filtered and the filtrate was concentrated to dryness. Thus obtained was passed through a column of "CM-Sephadex C-25" as eluted gradiently with aqueous ammonia while changing the concentration of ammonia from 0N to 0.15N. The active fractions of the eluate containing the intended product were concentrated to dryness to give the titled Compound (50) as a solid (73.8 mg). (Yield: 62%, calculated as the monocarbonate-monohydrate)

Example 12

Preparation of 1-N[(S)-4-amino-2-hydroxybutyryl]-5,4'-dideoxy-5,5-difluorokanamycin B (Compound 51)

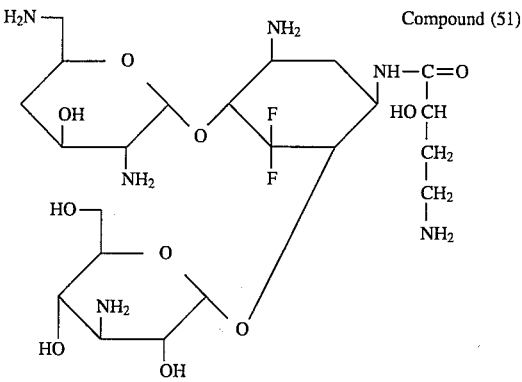

Compound (50) as obtained in Example 11(c) was subjected to 3,2',6'-tris-N-benzyloxycarbonylation, 3"-N-trifluoroacetylation, 1-N-[(S)-4-benzyloxycarbonylamino-2-hydroxybutyryl]ation, de-3"-N-trifluoroacetylation and then de-tetrakis-N-benzyloxycarbonylation in the similar manners to those in Referential Example 2(a) and (b) and also Example 2(a) and (b), thereby affording the titled Compound (51) as a solid.

Referential Example 11

(a) Preparation of 1,3,2',6',3''-pentakis(N-benzyloxycarbonyl)gentamicin $C_1$ (compound 52)

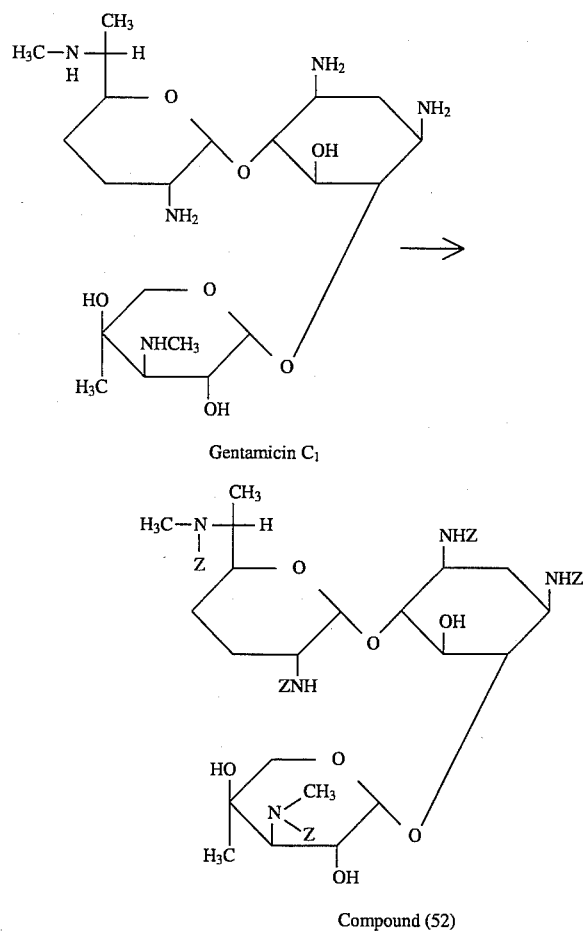

Gentamicin $C_1$

Compound (52)

A mixture of gentamicin $C_1$ (1.30 g) and sodium carbonate (1.30 g) was suspended in a mixed solvent of water (12 ml) and dioxane (25 ml), followed by addition of benzyloxycarbonyl chloride (2.30 ml) at 0° to 5° C. so as to conduct the reaction at room temperature for 1 hour. The reaction solution was concentrated under reduced pressure, and the resultant residue was dissolved in chloroform, washed successively with a 5% aqueous solution of sodium hydrogen carbonate and water, dried over anhydrous magnesium sulfate and concentrated under reduced pressure. The resulting solid residue was washed with isopropyl ether and dried so that there was afforded the titled Compound (52) as a solid (3.25 g). Yield: 97%

(b) Preparation of 1,3,2',6'-tetrakis(N-benzyloxycarbonyl)-3'',4''-N,O-carbonylgentamicin $C_1$ (Compound 53)

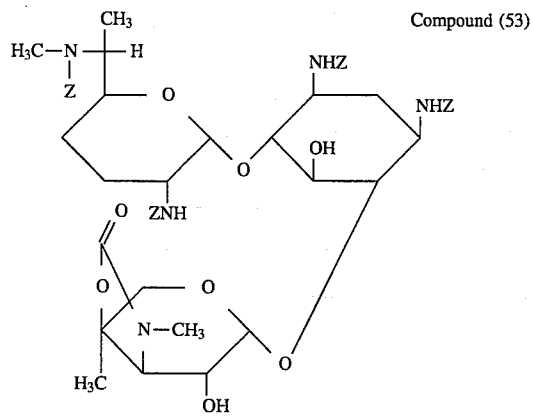

Compound (53)

Compound (52) (3.25 g) as obtained in the step (a) above was dissolved in DMF (30 ml), followed by addition of sodium hydride (400 mg) at 0° to 5° C. so as to effect the reaction at room temperature for 1 hour (for the formation of 3'',4''-N,O-carbonyl group, namely formation of cyclic carbamate group). The reaction solution was admixed with chloroform (50 ml) and water (50 ml) and neutralized by addition of 1N hydrochloric acid with stirring. The chloroform layer formed was separated from the reaction solution, washed with water and concentrated under reduced pressure. The resulting residue was subjected to column chromatography on silica gel eluting with a mixed eluent of chloroform and methanol (100:1) for the separation and purification of the intended product to afford the titled Compound (53) as a solid (2.68 g). Yield: 96%

(c) Preparation of 2''-O-benzoyl-1,3,2',6'-tetrakis(N-benzyloxycarbonyl)-3'',4''-N,O-carbonylgentamicin $C_1$ (Compound 54)

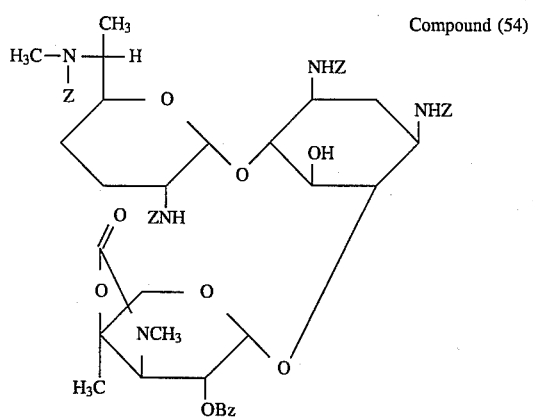

Compound (54)

Compound (53) (2.67 g) as obtained in the step (b) above was dissolved in pyridine (30 ml), followed by addition of benzoyl chloride (1.2 ml: 4.4 mole equivalents) at 0° to 5° C. so as to effect the reaction at room temperature for 1 hour (for the benzoylation of 2''-hydroxyl group). Water (1 ml) was added to the reaction solution which was then concentrated under reduced pressure. The resultant residue was dissolved in chloroform and washed successively with a 5% aqueous solution of sodium hydrogen carbonate and water. The solution in chloroform was dried over anhydrous magnesium sulfate and concentrated under reduced pressure to give the titled Compound (54) as a solid (2.88 g; Yield %).

(d) Preparation of 2"-O-benzoyl-1,3,2',6'-tetrakis(N-benzyloxycarbonyl)-3",4"-N,O-carbonyl-5-deoxy-5-oxogentamicin $C_1$ (Compound 55)

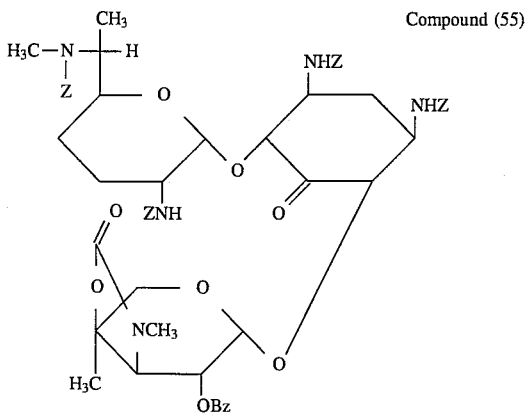

Compound (55)

Compound (54) (2.9 g) as obtained in the step (c) above was dissolved in methylene chloride (40 ml), followed by addition of "Molecular Sieve 4A" (2.80 g) and pyridinium chlorochromate (1.40 g: 2.6 mole equivalents). The resulting reaction solution was refluxed under heating for 5 hours (for the oxidation of 5-hydroxyl group). The reaction solution was then subjected to column chromatography on silica gel as eluted with a mixed eluent of chloroform and methanol (25:1), thereby affording the titled Compound (55) as a solid (2.68 g). Yield: 93[{]jf44b

Example 13

(a) Preparation of 2"-O-benzoyl-1,3,2',6'-tetrakis(N-benzyloxycarbonyl)-3",4"-N,O-carbonyl-5-deoxy-5,5-difluorogentamicin $C_1$ (Compound 56)

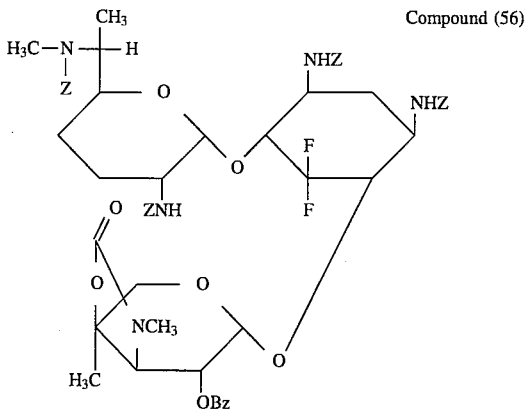

Compound (56)

Compound (55) (2.68 g) as obtained in Referential Example 11(d) was dissolved in methylene chloride (30 ml), followed by addition of diethylaminosulfur trifluoride (3.2 ml) under ice-cooling to conduct the reaction at room temperature for 8 hours (for the di-fluorination). The reaction solution was subjected to thin layer chromatography (TLC) on silica gel as eluted with a mixed eluent of chloroform and methanol (25:1), which showed the main product at Rf 0.54 and many by-products at Rf 7.5 to 8.0. The reaction solution was admixed with a 5% aqueous solution of $NaHCO_3$ (30 ml) and stirred for 30 minutes. The methylene chloride layer was separated from the reaction solution, washed with water and concentrated under reduced pressure. The resulting residue was subjected to column chromatography on silica gel as eluted with a mixed solvent of chloroform and methanol (100:1) for the separation and purification of the intended product, thereby affording the titled Compound (56) as a solid (1.56 g). Yield: 57%

(b) Preparation of 5-deoxy-5,5-difluorogentamicin $C_1$ (Compound 57)

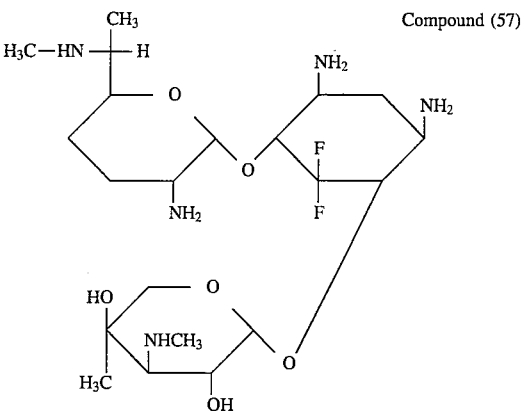

Compound (57)

To liquefied ammonia (about 50 ml) at −50° to −60° C., was added a solution (about 2.5 ml) in tetrahydrofuran (THF) of Compound (56) (1.56 g) as obtained in the step (a) above. Metal sodium (about 400 mg) was added to the resulting solution. The reaction was conducted for 10 minutes. The resulting reaction solution was subjected to TLC on silica gel as eluted with the lower phase of a mixed solvent of chloroform-methanol-28% aqueous ammonia (1:1:1), when the main product appeared at Rf 0.76. The reaction solution was concentrated to a small volume and admixed with water (10 ml) to conduct the reaction at 80° C. for 3 hours (for the removal of the carbamate ring). The resulting reaction solution was neutralized by addition of 6N hydrochloric acid and then adsorbed on a column of "CM-Sephadex C-25" ($NH_4^+$ -form) resin. The column was washed with water and eluted with aqueous ammonia while changing the concentration of ammonia from 0N to 0.2N. The active fractions of the eluate were combined and concentrated under reduced pressure. The resultant residue was subjected to column chromatography on silica gel as eluted with a mixed eluent of chloroform-methanol-28% aqueous ammonia (9:4:1) for the separation and purification of the intended product, thereby giving the titled Compound (57) as a solid (2.88 g). Yield: 45%

Specific rotation: $[\alpha]_D^{24}+147°$ (c 0.5, water)

$^1$H-NMR (20% $ND_3/D_2O$): δ0.27 (3H, d, H-7', $J_{6',7'}=7$ Hz), 2.23 (3H s, 4"-$CH_3$), 3.33 and 3.57(each 3H, s, 6'-$NCH_3$ and 6 12(each 1H, d, H-1' and H-1", $J_{1",2"}=3.5$ Hz)

$^{19}$F-NMR(20% $ND_3/D_2O$): δ−128.28(dt, $J_{F,F}=246$ Hz, $J_{4,F}=J_{6,F}=20$ Hz) and −113.28(dt, $J_{4,F}=J_{6,F}=3.5$ Hz)

Referential Example 12

(a) Preparation of 3,2',6'-tris(N-benzyloxycarbonyl)-5deoxy-5,5-difluorogentamicin $C_1$ (Compound 58)

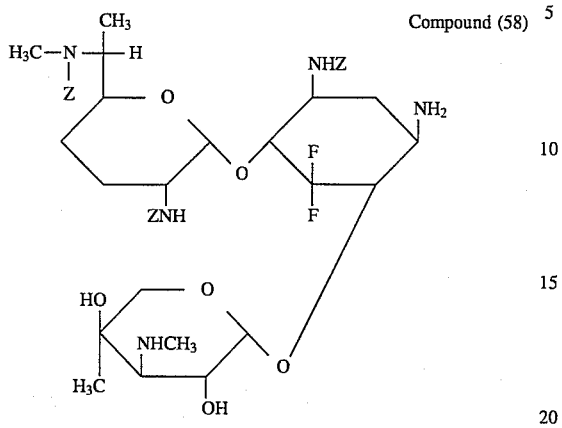

Compound (58)

Compound (57) (50.1 mg) as obtained in Example 13 (b) and cobalt acetate tetrahydrate (78.0 mg) were dissolved in DMSO (1 ml) to prepare solution containing a complex of Compound (57) with cobalt cation. The resulting solution was admixed with benzyloxycarbonyloxy succinimide (78.0 mg) to conduct the reaction at room temperature for 1.5 hours. The reaction solution was washed with ethyl ether, admixed with ethyl acetate (4 ml), washed with 28% aqueous ammonia and concentrated under reduced pressure to afford the titled Compound (58) as a solid (93.1 mg).

(b) Preparation of 3,2',6'-tris(N-benzyloxycarbonyl)-5-deoxy-5,5-difluoro-3"-N-trifluoroacetylgentamicin $C_1$ (Compound 59)

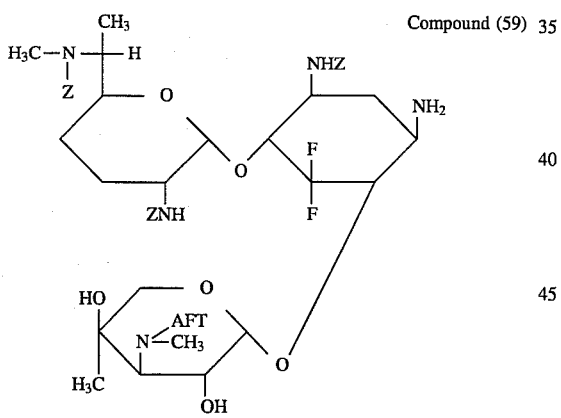

Compound (59)

wherein AFT means a trifluoroacetyl group here and hereinafter.

Compound (58) (93.1 mg) as obtained in the step (a) above was dissolved in dioxane (2 ml), followed by addition of ethyl trifluoroacetate (0.1 ml) to conduct the reaction at room temperature for 1 hour (for the trifluoroacetylation of 3"-amino group). The reaction solution was subjected to TLC as eluted with a mixed solvent of chloroform-methanol-28% aqueous ammonia (5:1:1), when a single spot appeared at Rf 0.73. The reaction solution was concentrated under reduced pressure to give the titled Compound (59) as a solid (101 mg).

Example 14

(a) Preparation of 3,2',6'-tris(N-benzyloxycarbonyl)-1-N-[(S)-4-benzyloxycarbonylamino-2-hydroxybutyryl]-5-deoxy-5,5-difluoro-3"-N-trifluoroacetylgentamicin $C_1$ (Compound 60)

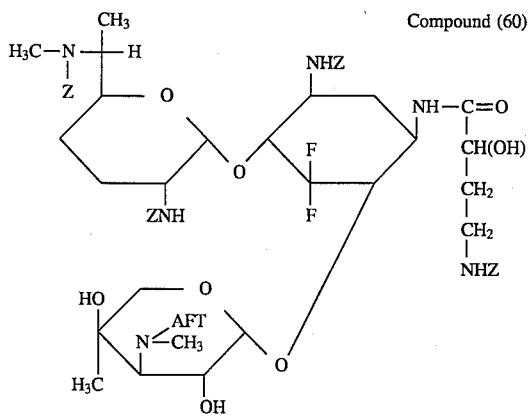

Compound (60)

Compound (59) (101 mg) obtained in Referential Example 12(b) was dissolved in dioxane (4 ml). The resultant solution was added with triethylamine (0.5 ml) and the N-hydroxysuccinimide ester (the active ester) (47.5 mg) of (S)-4-benzyloxycarbonylamino-2-hydroxybutyric acid, followed by conducting the reaction at room temperature for 2 hours. The resulting reaction solution was concentrated under reduced pressure, followed by addition of water to form a solid. The resulting solid was washed with water and then dried under reduced pressure to afford 126 mg of the titled Compound (60) as a solid.

(b) Preparation of 1-N-[(S)-4-amino-2-hydroxybutyryl]-5-deoxy-5,5-difluorogentamicin $C_1$ (Compound 61)

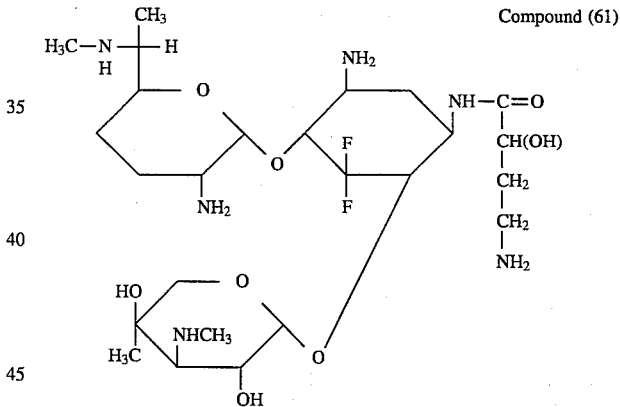

Compound (61)

Compound (60) (126 mg) as obtained in the step (a) above was dissolved in dioxane (2 ml), to which 28% aqueous ammonia (1 ml) was added, followed by conducting the reaction at room temperature for 16 hours (for the de-trifluoroacetylation). After concentrating the reaction solution under reduced pressure, the resulting residue was dissolved in a mixed solvent of dioxane (2 ml), water (0.5 ml) and acetic acid (0.2 ml) and then was subjected to catalytic reduction at ambient temperature for 2 hours under atmospheric pressure. The resulting reaction solution was filtered and the filtrate was concentrated to a small volume under reduced pressure, and then chromatographed in a column of "CM-Sephadex C-25" ($NH_4^+$-form) as eluted gradiently with aqueous ammonia, while changing the concentration of ammonia continuously from 0N to 0.5N. Fractions of the eluate containing the desired compound were combined together and concentrated to dryness to afford 23.9 mg (yield: 40% based on Compound (57)) of the titled Compound (61) as a solid.

$[\alpha]_D^{24}$ +129° (c 12, water)

$^1$H-NMR(DCl/$D_2$O, pD<1): δ1.28(3H, d, H-7', $J_{6',7'}$=7 Hz) 1.40(3H, s, 4"-$CH_3$), 2.78 and 2.92 (each 3H, s, 6'-NCH$_3$ and 3"-NCH$_3$), 5.18 and 5.74 (each 1H, d, H-1' H-1", J$_{1',2}$=J$_{1",2"}$=3.5 Hz)

$^{13}$C-NMR(DCl/D$_2$O, pD<1): δ74.2 and 77.6 (each t, C-4 and C-6), 120.4 (t, C-5)

Referential Example 13

(a) Preparation of 1,3,2',6',3"-pentakis (N-benzyloxycarbonyl)gentamicin C$_2$ (Compound 62)

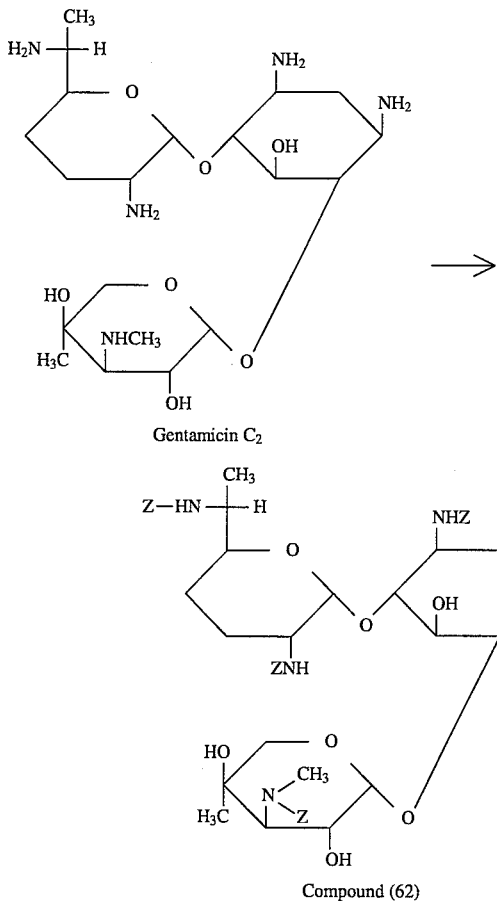

Gentamicin C$_2$ (1.00 g) and sodium carbonate (1.0 g) were suspended in a mixed solvent of water (10 ml) and dioxane (20 ml), followed by addition of benzyloxycarbonyl chloride (1.7 ml) at 0°–5° C. The resulting mixture was treated in the same manner as in Referential Example 11(a) to afford 2.93 g (yield: 98%) of the titled Compound (62) as a solid.

(b) Preparation of 1,3,2',6'-tetrakis(N-benzyloxycarbonyl)-3",4"-N,O-carbonylgentamicin C$_2$ (Compound 63)

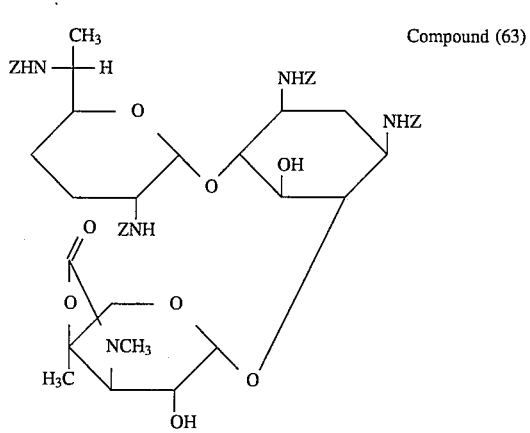

Compound (62) (1.63 g) as obtained in the step (a) above was dissolved in DMF (16 ml). The resulting solution was added with sodium hydride (200 mg) at 0°–5° C, followed by conducting the reaction at room temerature for 1 hour (for the formation of the cyclic carbamate group). The resulting reaction solution was thereafter treated in the same manner as in Referential Example 11(b) to afford 1.37 g (yield: 93%) of the titled Compound (63) as a solid.

(c) Preparation of 2"-O-benzoyl-1,3,2',6'-tetrakis(N-benzyloxycarbonyl)-3",4"-N,O-carbonylgentamicin C$_2$ (Compound 64)

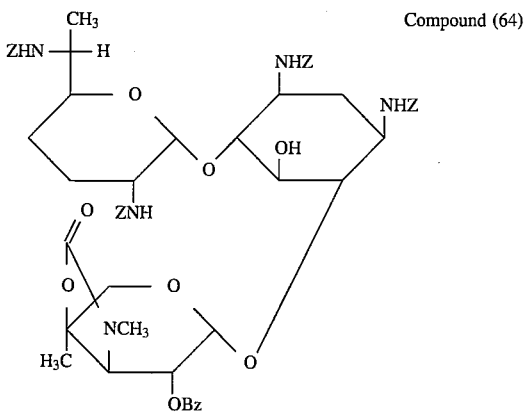

Compound (63) (716 mg) as obtained in the step (b) above was dissolved in pyridine (7.2 ml), to which benzoyl chloride (0.35 ml, 5.7 mole equivalents) was added at 0°–5° C., followed by conducting the reaction at room temperature for 1 hour (for the benzoylation of the 2"-hydroxyl group). The resulting reaction solution was thereafter treated in the same manner as in Referential Example 11(c) to afford 776 mg (yield: 98%) of the titled Compound (64) as a solid.

(d) Preparation of 2"-O-benzoyl-1,3,2',6'-tetrakis(N-benzyloxycarbonyl)-3",4"-N,O-carbonyl-5-deoxy-5-oxogentamicin C$_2$ (Compound 65)

73

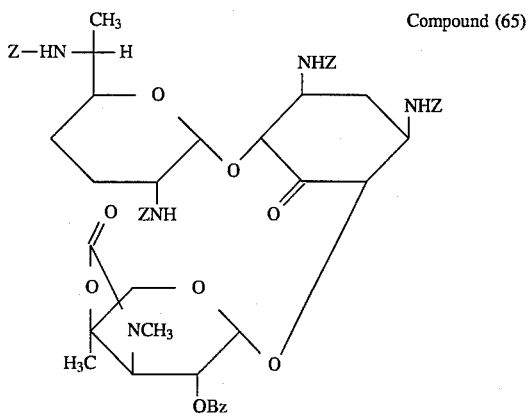
Compound (65)

Compound (64) (1.32 g) as obtained in the step (c) above was dissolved in methylene chloride (28 ml). The resulting solution was added with "Molecular Sieves 4A" (1.36 g) and pyridinium chlorochromate (960 mg)(3.9 mole equivalents), followed by conducting the oxidative reaction under reflux for 5 hours while heating. The reaction solution showed a single spot at Rf value of 0.45 in silica gel TLC (a developing solvent: $CHCl_3$-MeOH, 25:1). The resulting reaction solution was isolated and purified by column chromatography on silica gel (a developing solvent: chloroform-methanol, 25:1) to afford 1.19 g (yield: 90%) of the titled Compound (65) as a solid.

Example 15

(a) Preparation of 2"-O-benzoyl-1,3,2',6'-tetrakis(N-benzyloxycarbonyl)-3",4"-N,O-carbonyl-5-deoxy-5,5-difluorogentamicin $C_2$ (Compound 66 )

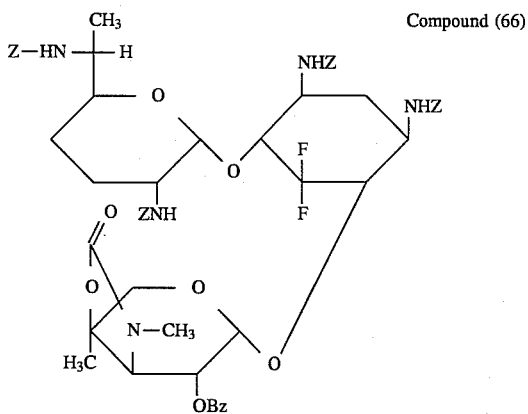
Compound (66)

Compound (65) (1.19 g) as obtained in Referential Example 13(d) was dissolved in methylene chloride (20 ml), to which diethylaminosulfur trifluoride (1.6 ml) was added under ice-cooling, followed by conducting the reaction at room temperature for 8 hours (for the di-fluorination). The reaction solution showed a single spot of the main product at Rf value of 0.47 and multiple spots of by-products at Rf of 0.74–0.77 in silica gel TLC (the TLC was developed with a mixed solvent of $CHCl_3$-MeOH, 25:1) . The resulting reaction solution was added with a 5% aqueous solution of sodium hydrogen carbonate (20 ml) and then stirred for 30 minutes. Thereafter, the methylene chloride layer was separated, washed with water and then concentrated. The resulting residue was purified by column chromatography on silica gel (developed with a mixed solvent of chloroform-methanol, 25:1) to afford 755 mg (yield: 62%) of the titled Compound (66) as a solid.

(b) Preparation of 5-deoxy-5,5-difluorogentamicin $C_2$ (Compound 67)

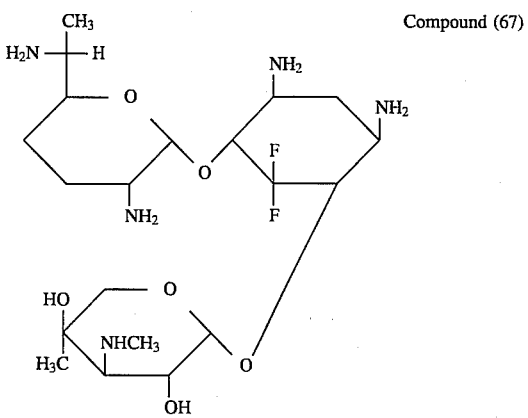
Compound (67)

A solution (about 3 ml) in THF of Compound (66) of the step (2) (755 mg) was added into liquefied ammonia (about 30 ml) at −50° to −60° C. The resulting mixture was added with metal sodium (about 400 mg), followed by conducting the reaction for 10 minutes. The resulting reaction solution showed a spot of the main product at Rf value of 0.73 in silica gel TLC (the TLC was developed with the lower layer of a mixed developing solvent of $CHCl_3$-MeOH-28% $NH_4OH$, 1:1:1). The reaction solution was concentrated, added with water (10 ml) and then subjected to the reaction for 3 hours to effect the breakdown of the cyclic carbamate group. The resulting reaction solution showed a spot of the main product at Rf value of 0.39 in silica gel TLC (the TLC was developed with the lower layer of a mixed developing solvent of $CHCl_3$-MeOH-28% $NH_4OH$, 1:1:1).

The resulting reaction solution was neutralized with 6N hydrochloric acid, and then was treated with the resin "CM-Sephadex C-25 ($NH_4^+$-form)" to adsorb the resultant reaction product therein. After washing the resin column with water, the column was eluted gradiently with aqueous ammonia, while changing the concentration of ammonia from 0N to 0.2N. Active fractions of the eluate containing the desired compound were concentrated and thereafter the resulting residue was purified by column chromatography on silica gel, in such way that the column was developed with a developing solvent of $CHCl_3$-MeOH-28% $NH_4OH$ (9:4:1), thereby affording 201 mg (yield: 58%) of the titled Compound (67) as a solid.

$[\alpha]_D^{24}$+162° (c 0.4, water)

$^1$H-NMR(20% $ND_3/D_2O$): δ1.80(3H, d, H-7', $J_{6',7'}$=7 Hz), 1.95(3H, s, 4"-$CH_3$), 3.28(3H, s, $NCH_3$), 5.80 and 5.83 (each 1H, d, H-1' and H-1", $J_{1',2'}$=$J_{1'',2''}$=3.5 Hz)

$^{19}$F-NMR(20% $ND_3/D_2O$): δ−133.13(dt, $J_{F,F}$=246 Hz, $J_{4,F}$=$J_{6,F}$=21 Hz) and −110.32(dt, $J_{4,F}$=$J_{6,F}$=4 Hz)

Referential Example 14

(a) Preparation of 3,2',6'-tris(N-benzyloxycarbonyl)-5-deoxy-5,5-difluorogentamicin $C_2$ (Compound 68)

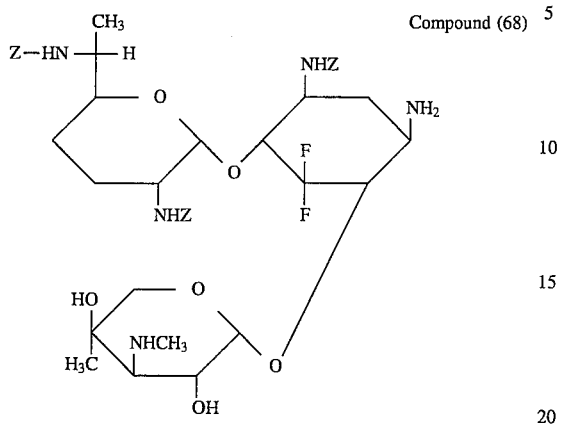

Compound (67) (31.0 mg) as obtained in Example 15 (b) and cobalt acetate tetrahydrate (51.5 mg) were dissolved in DMSO (0.6 ml). The resulting solution was added with benzyloxycarbonyloxysuccinimide (49.1 mg), followed by conducting the reaction at room temperature for 1.5 hours. The resulting reaction solution was thereafter treated in the same manner as in Referential&1 Example 12(a) to afford 54.5 mg of the titled Compound (68) as a solid.

(b) Preparation of 3,2',6'-tris(N-benzyloxycarbonyl)-5-deoxy-5,5-difluoro-3"-N-trifluoroacetylgentamicin $C_2$ (Compound 69)

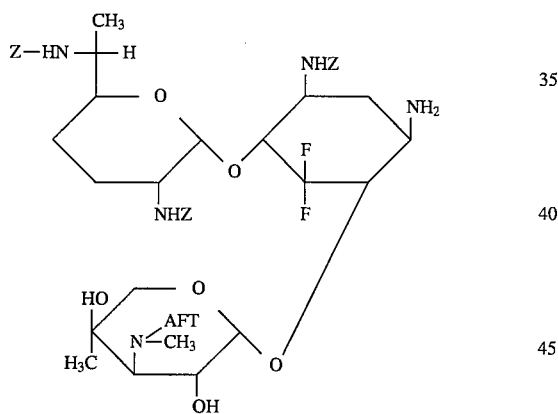

Compound (68) (54.5 mg) as obtained in the step (a) above was dissolved in dioxane (1 ml). The resulting solution was added with ethyl trifluoroacetate (0.1 ml), followed by conducting the reaction for 1 hour at room temperature (for the trifluoroacetylation of the 3"-amino group). The resulting reaction solution was treated in the same manner as in Referential Example 12(b) to afford 60.5 mg of the titled Compound (69) as a solid.

Example 16

(a) Preparation of 3,2',6"-tris(N-benzyloxycarbonyl)-1-N-[(S)-4-benzyloxycarbonylamino-2-hydroxybutyryl]-5-deoxy-5,5-difluorogentamicin $C_2$ (Compound 70)

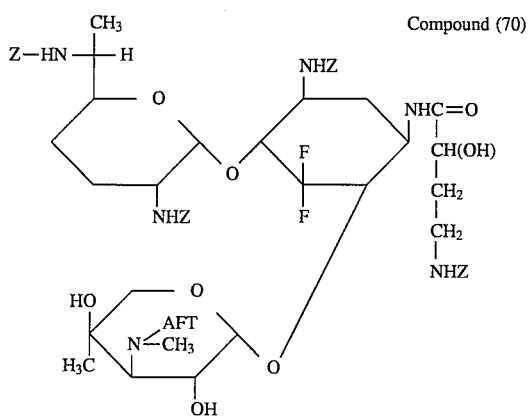

Compound (69) (60.5 mg) as obtained in Referential Example 14(b) was dissolved in dioxane (3 ml). The resultant solution was added with triethylamine (0.4 ml) and N-hydroxysuccinimide (the active ester) (29.6 mg) of (S)-4-benzyloxycarbonylamino-2-hydroxybutyric acid, and the reaction was conducted at room temperature for 2 hours. The resulting reaction solution was thereafter treated in the same manner as in Example 14(a) to afford 74.5 mg of the titled Compound (70) as a solid.

(b) Preparation of 1-N-[(S)-4-amino-2-hydroxybutyryl]-5-deoxy-5,5-difluorogentamicin $C_2$ (Compound 71)

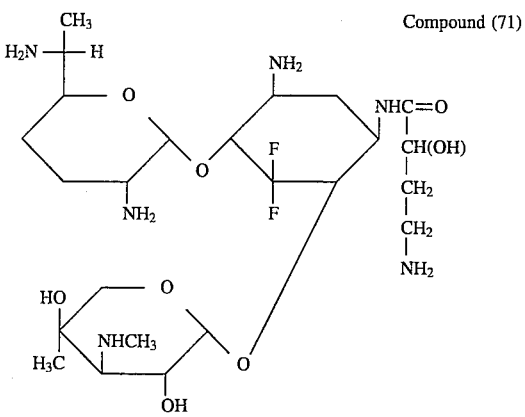

Compound (70) (74.5 mg) as obtained in the step (a) above was dissolved in dioxane (1.5 ml). The resulting solution was added with 28% aqueous ammonia (0.7 ml), followed by conducting the reaction at room temperature for 16 hours. The resulting reaction solution was thereafter treated and subjected to the catalytic reduction and further treated in the same manner as in Example 14(b), to afford 16.1 mg (yield: 43% based on Compound (67)) of the titled Compound (71) as a solid.

$[\alpha]_D^{24}+107°$ (c 12, water)

$^1$H-NMR(DCl/$D_2$O, pD<1): δ1.34(3H, d, H-7', $J_{6',7'}$=7 Hz), 1.40(3H, s, 4"-$CH_3$), 2.93(3H, s, $NCH_3$), 5.16 and 5.70 (each 1H, d, H-1' and H-1", $J_{1',2'}$=$J_{1",2"}$=3.5 Hz)

$^{13}$C-NMR(DCl/$D_2$O, pD<1): δ74.5 (each t, C-4 and C-6), 120.4 (t, C-5)

Referential Example 15

(a) Preparation of 1,3,2',6',3"-pentakis(N-benzyloxycarbonyl)gentamicin $C_{1a}$ (Compound 72)

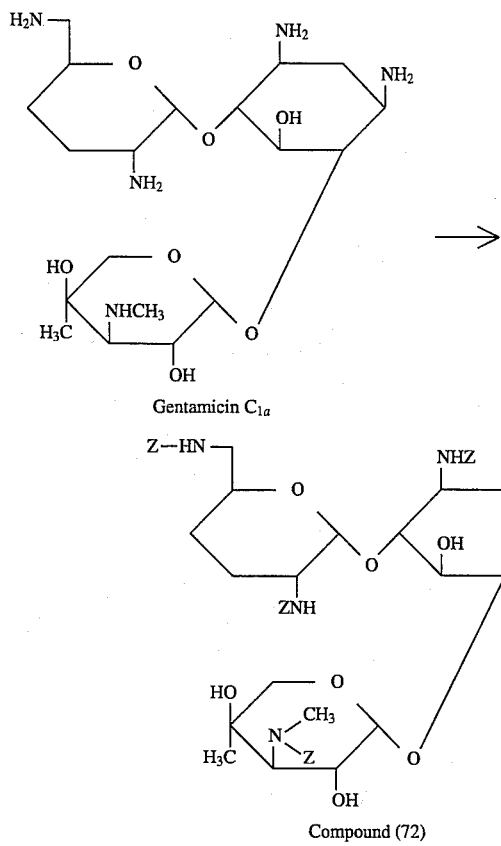

Gentamicin $C_{1a}$ (1.05 g) and sodium carbonate (1.0 g) were suspended in a mixed solvent of water (10 ml) and dioxane (20 ml), to which benzyloxycarbonyl chloride (1.8 ml) was added at 0°–5° C., followed by conducting the reaction at room temperature for 1 hour. The resulting reaction solution was treated in the same manner as in Referential Example 11(a) to afford 2.58 g (yield: 99%) of the titled Compound (72) as a solid.

(b) Preparation of 1,3,2',6'-tetrakis(N-benzyloxycarbonyl)-3",4"-N,O-carbonylgentamicin $C_{1a}$ (Compound 73)

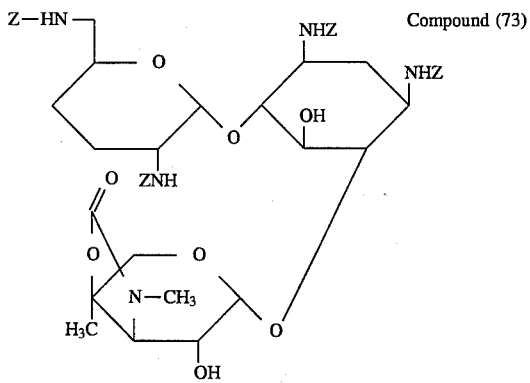

Compound (72) (2.58 g) as obtained in the step (a) above was dissolved in DMF (30 ml), to which sodium hydride (300 mg) was added at 0°–5° C., followed by conducting the reaction at room temperature for 1 hour. The resulting reaction solution was thereafter treated in the same manner as in Referential Example 11(b) to afford 2.27 g (yield: 97%) of the titled Compound (73) as a solid.

(c) Preparation of 2"-O-benzoyl-1,3,2',6'-tetrakis(N-benzyloxycarbonyl)-3",4"-N,O-carbonylgentamicin $C_{1a}$ (Compound 74)

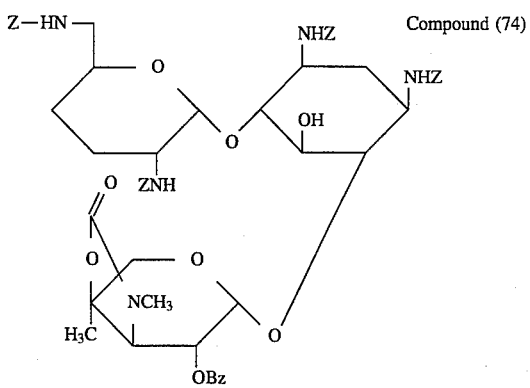

Compound (73) (2.27 g) of the step (b) above was dissolved in pyridine (30 ml), to which benzoyl chloride (1.1 ml, 4.6 mole equivalents) was added at 0°–5° C., followed by conducting the reaction at room temperature for 1 hour. The resulting reaction solution was thereafter treated in the same manner as in Referential Example 11(c) to afford 2.37 g (yield: 95%) of the titled Compound (74) as a solid.

(d) Preparation of 2"-O-benzoyl-1,3,2',6'-tetrakis(N-benzyloxycarbonyl)-3",4"-N,O-carbonyl-5-deoxy-5-oxo-gentamicin $C_{1a}$ (Compound 75)

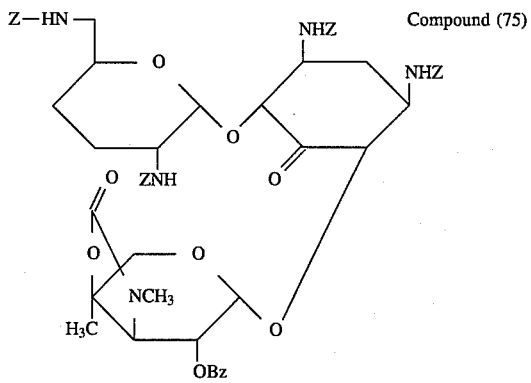

Compound (74) (2.37 g) as obtained in the step (c) above was dissolved in methylene chloride (50 ml). The resulting solution was added with "Molecular Sieves 4A" (2.0 g) and pyridinium chlorochromate (1.30 g, 3.2 mole equivalents), followed by conducting the oxidative reaction under reflux for 5 hours while heating. The reaction solution showed a single spot at Rf value of 0.42 in silica gel TLC (the TLC was developed with a mixed solvent of $CHCl_3$-MeOH, 25:1). The resulting reaction solution was isolated and purified by column chromatography on silica gel, in such way that the column was developed with a mixed solvent of $CHCl_3$-MeOH (25:1), thereby affording 2.23 g (yield: 94%) of the titled Compound (75) as a solid.

Example 17

(a) Preparation of 2"-O-benzoyl-1,3,2',6'-tetrakis(N-benzyloxycarbonyl)-3",4"-N,O-carbonyl-5-deoxy-5,5-difluorogentamicin $C_{1a}$ (Compound 76)

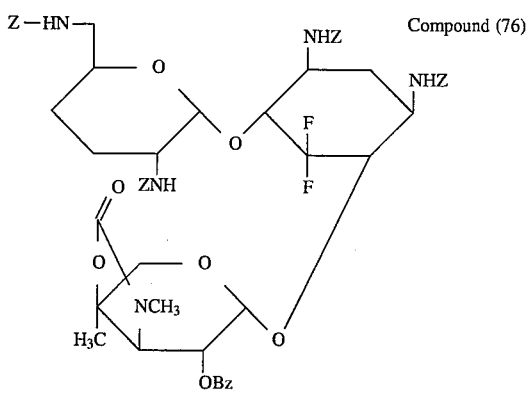

Compound (76)

Compound (75) (2.23 g) as obtained in Referential Example 15(d) was dissolved in methylene chloride (45 ml), added with diethylaminosulfur trifluoride (3.0 ml) under ice-cooling, followed by conducting the reaction at room temperature for 8 hours (for the di-fluorination). The reaction solution showed a spot of the main product at Rf value of 0.45 and multiple spots of by-products at Rf of 0.72–0.76 in silica gel TLC (the TLC was developed with a mixed solvent of $CHCl_3$-MeOH, 25:1). The resulting reaction solution was added with a 5% aqueous solution of sodium hydrogen carbonate (45 ml). After stirring for 30 minutes, the methylene chloride layer was separated, washed with water and then concentrated. The resulting residue was purified by column chromatography on silica gel in such way that the column was developed with a developing solvent of $CHCl_3$-MeOH (100:1), thereby affording 1.25 g (yield: 55%) of the titled Compound (76) as a solid.

(b) Preparation of 5-deoxy-5,5-difluorogentamicin $C_{1a}$ (Compound 77)

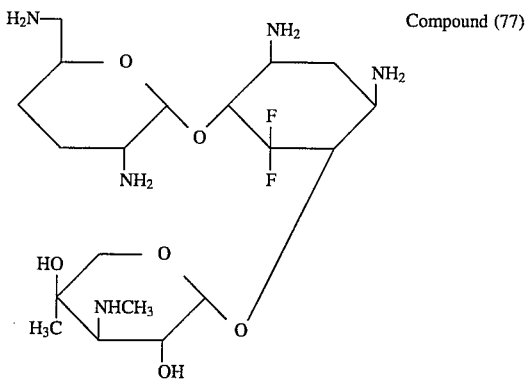

Compound (77)

A solution (about 2.5 ml) in THF of Compound (76) (1.25 g) as obtained in the step (a) above was added to liquefied ammonia (about 50 ml) at −50° to −60° C. The resulting mixture was added with metal sodium (about 400 mg), followed by conducting the reaction for 10 minutes. The reaction solution showed a spot of the main product at Rf value of 0.70 in silica gel TLC (the TLC was developed with the lower layer of a mixed developing solvent of $CHCl_3$-MeOH-28% $NH_4OH$, 1:1:1). The resulting reaction solution was concentrated and then added with water (10 ml). The resulting mixture was reacted at 80° C. for 3 hours to effect the breakdown the cyclic carbamate group. The reaction solution showed a spot of the main product at Rf value of 0.36 in silica gel TLC (the TLC was developed with the lower layer of a mixed developing solvent of $CHCl_3$-MeOH-28% $NH_4OH$, 1:1:1).

The resulting reaction solution was neutralized with 6N hydrochloric acid and then adsorbed on the resin "CM-Sephadex C-25 ($NH_4^+$-form)". After washing the resin column with water, the column was eluted gradiently with aqueous ammonia, while changing the concentration of ammonia from 0N to 0.2N. Fraction of the eluate containing the desired compound were combined together and concentrated under reduced pressure. The resulting residue was purified by column chromatography on silica gel, in such way that the column was developed with a developing solvent of $CHCl_3$-MeOH-28% $NH_4OH$ (9:4:1), thereby affording 238 mg (yield: 46%) of the titled Compound (77) as a solid.

$[\alpha]_D^{24}$+169° (c 0.4, water)

$^1$H-NMR(20% $ND_3/D_2O$): δ1.94(3H, s, 4″-$CH_3$), 3.27(3H, s, N-$CH_3$), 5.80 and 5.84 (each 1H, d, $J_{1',2'}$=$H_{1''}$, $_{2''}$=3.5 Hz)

$^{19}$F-NMR(20% $ND_3/D_2O$): δ−128.15(dt, $J_{F,F}$=246 Hz, $J_{4,F}$=$J_{6,F}$=21 Hz) and −110.35 (dt, $J_{4,F}$=$J_{6,F}$=4 Hz)

Referential Example 16

(a) Preparation of 1,3,2′,6′,3″-pentakis(N-benzyloxycarbonyl)netilmicin (Compound 78)

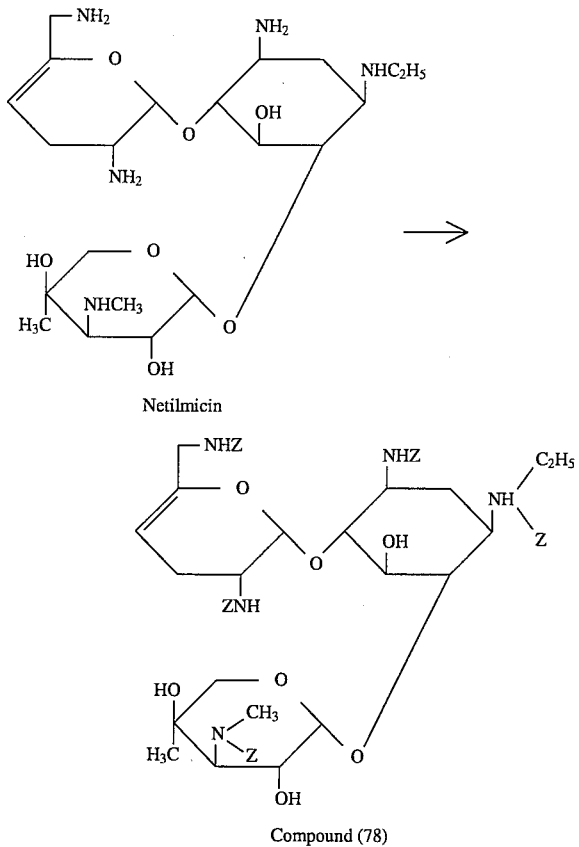

Compound (78)

Netilmicin (420 mg) and sodium carbonate (500 mg) were suspended in a mixed solvent of water (10 ml) and dioxane (10 ml). The resulting mixture was added with benzyloxycarbonyl chloride (1.0 ml) at 0°–5° C., followed by conducting the reaction at room temperature for 1 hour. The reaction solution showed a single spot at Rf value of 0.42 in TLC (the TLC was developed with a mixed solvent of $CHCl_3$-MeOH, 25:1). The resulting reaction solution was concentrated under reduced pressure and the residue was dissolved in chloroform. The resulting chloroform solution was washed successively with a 5% aqueous solution of sodium hydrogen carbonate and water, dried over anhydrous magnesium sulfate and then concentrated under reduced pressure. The resulting residue was washed with isopropyl ether to afford 947 mg (yield: 94%) of the titled Compound (78) as a solid.

$[\alpha]_D^{24}$ +83° (c 0.3 CHCl$_3$)

(b) Preparation of 1,3,2',6'-tetrakis(N-benzyloxycarbonyl)-3",4"-N,O-carbonylnetilmicin (Compound 79)

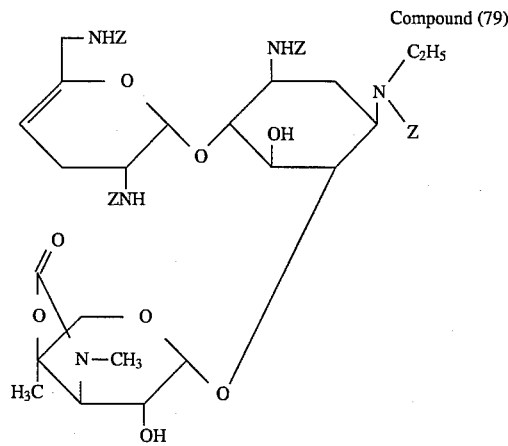

Compound (79)

Compound (78) (1.09 g) as obtained in the step (a) above was dissolved in DMF (10 ml). The resulting solution was added with sodium hydride (110 mg) at 0°–5° C., followed by conducting the reaction at room temperature for 1 hour (for the formation of the cyclic carbamate group). The resulting reaction solution was added with chloroform (20 ml) and water (20 ml) and then neutralized with 1N hydrochloric acid, while stirring. The chloroform layer was separated, washed with water and then concentrated under reduced pressure. The resulting residue was purified by column chromatography on silica gel, in such way that the column was developed with a developing solvent of CHCl$_3$-MeOH (100:1), thereby affording 931 mg (yield: 94%) of the titled compound (79) as a solid.

$[\alpha]_D^{24}$ +75° (c 0.3, CHCl$_3$)

(c) Preparation of 2"-O-benzoyl-1,3,2',6'-tetrakis(N-benzyloxycarbonyl)-3",4"-N,O-carbonylnetilmicin (Compound 80)

Compound (79) (891 mg) as obtained in the step (b) above was dissolved in pyridine (15 ml), followed by addition of benzoyl chloride (0.5 ml) at 0°–5° C. The reaction was conducted at room temperature for 1 hour (for benzoylation of 2"-hydroxyl group). The resulting reaction solution was added with water (0.5 ml) and concentrated under reduced pressure. The resulting residue was dissolved in chloroform and the resulting solution was washed successively with a 5% aqueous solution of sodium hydrogen carbonate and water. The chloroform solution was dried over anhydrous magnesium sulfate and then concentrated under reduced pressure to afford 902 mg (yield: 92%) of the titled Compound (80) as solid.

$[\alpha]_D^{24}$ +94° (c 0.2, CHCl$_3$)

(d) Preparation of 2"-O-benzoyl-1,3,2',6'-tetrakis(N-benzyloxycarbonyl)-3",4"-N,O-carbonyl-5-deoxy-5-oxonetilmicin (Compound 81)

Compound (80) (641 mg) as obtained in the step (c) above was dissolved in dimethylsufoxide (1.5 ml), followed by addition of acetic anhydride (0.5 ml). The reaction was made at room temperature for 16 hours (for the oxidation of the 5-hydroxyl group). The resulting reaction solution was dissolved in chloroform and the solution in chloroform was washed successiely with water, a 5% aqueous solution of sodium hydrogen carbonate and water. The solution in chloroform was dried over anhydrous magnesium sulfate and then concentrated under reduced pressure. The residue was purified by column chromatography on silica gel, in such way that the column was developed with a developing solvent of CHCl$_3$-MeOH (100:1), thereby affording 608 mg (yield: 95%) of the titled Compound (81) as a solid.

$[\alpha]_D^{24}$ +101° (c 0.2, CHCl$_3$)

Example 18

(a) Preparation of 2"-O-benzoyl-1,3,2',6'-tetrakis(N-benzyloxycarbonyl)-3",4"-N,O-carboyl-5-deoxy-5,5-difluoronetilmicin (Compound 82)

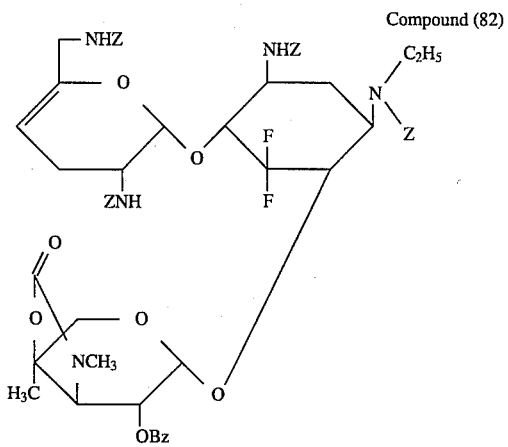

Compound (82)

Compound (81) (511 mg) as obtained in Referential Example 16(d) was dissolved in methylene chloride (8.0 ml). The resulting solution was added with diethylaminosulfur trifluoride (0.6 ml) under ice-cooling, followed by conducting the reaction at room temperature for 6 hours (for the di-fluorination). The resulting reaction solution was added with a 5% aqueous solution of sodium hydrogen carbonate (15 ml) and then stirred for 30 minutes. The methylene chloride layer was separated, washed with water and then concentrated. The residue was purified by column chromatography on silica gel, in such way that the column was developed with a developing solvent of CHCl$_3$-MeOH (100:1), thereby affording 325 mg (yield: 62%) of the titled Compound (82) as a solid.

$[\alpha]_D^{24}$ +90° (c 0.3, CHCl$_3$)

(b) Preparation of 5-deoxy-5,5-difluoronetilmicin (Compound 83)

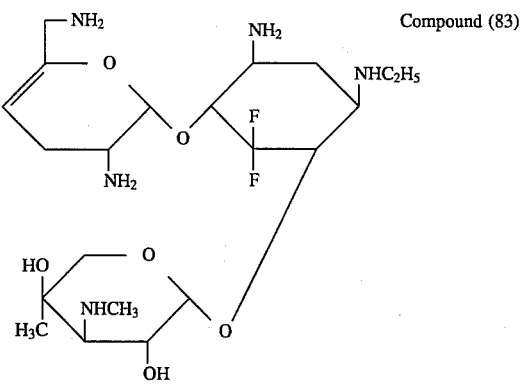

Compound (83)

A solution (about 1 ml) in THF of Compound (82) (245 mg) was added to liquefied ammonia (about 25 ml) at −50° to −60° C. The resulting solution was added with metal sodium (about 300 mg), followed by conducting the reaction for 10 minutes. The resulting reaction solution was added with methanol (1 ml), concentrated, and then added with water (5 ml). The resulting mixture was reacted at 80° C. for 3 hours (for the breakdown of the cyclic carbamate group). The reaction solution showed a spot of the main product at Rf value of 0.25 in silica gel TLC (the TLC was developed with $CHCl_3$-MeOH-28% $NH_4OH$, 9:4:1).

The resulting reaction solution was neutalized with 6N hydrochloric acid and then adsorbed on the resin "CM-Sephadex C-25 ($NH_4^+$-form)". After washing the resin column with water, the column was eluted gradiently with aqueous ammonia, while changing the concentration of ammonia from 0N to 0.2N. Fractions of the eluate containing the desired compound were collected, combined together and concentrated under reduced pressure. The resulting residue was purified by column chromatography on silica gel, in such way that the column was developed with a developing solvent of $CHCl_3$-MeOH-28% $NH_4OH$ (9:4:1), thereby affording 54.4 mg (yield: 52%) of the titled Compound (83) as a solid.

$[\alpha]_D^{24}$+148° (c 1.0, water)
$^{19}$F-NMR(20% $ND_3/D_2O$: δ−128.68(dt, $J_{F,F}$=244 Hz, $J_{4,F}$=$J_{6,F}$=20 Hz) and −113.50(d)

Example 19

Preparation of 5-deoxy-5,5-difluoroneamine (Compound 84)

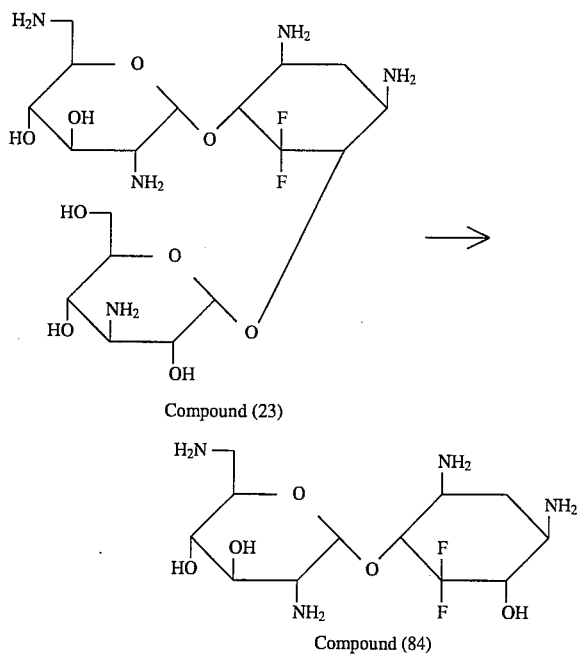

Compound (84)

Monocarbonate of 5-deoxy-5,5-difluorokanamycin B (which is Compound (23)) obtained in Example 5(c) (625 mg) was dissolved in an 4N aqueous hydrochloric acid solution (13 ml). Subsequently, the reaction was conducted at 100° C. for 1 hour to hydrolyze the Compound (23).

The resulting reaction solution was concentrated under reduced pressure and then neutralized with aqueous ammonia. The neutralized solution was passed through a column of the resin "Amberlite CG-50" ($NH_4^+$-form) on which the reaction product was adsorbed. The resin column was eluted gradiently with aqueous ammonia, while changing the concentration of ammonia 0N to 0.2N. Fractions of the eluate containing the intended compound were collected, combined together, and concentrated to dryness to afford 251 mg (yield: 52%, calculated as the monocarbonate-monohydrate) of the titled Compound (84) as a solid.

$[\alpha]_D^{20}$+70° (c 1, water)

Example 20

Preparation of 5,3',4'-trideoxy-5,5-difluoroneamine (Compound 85)

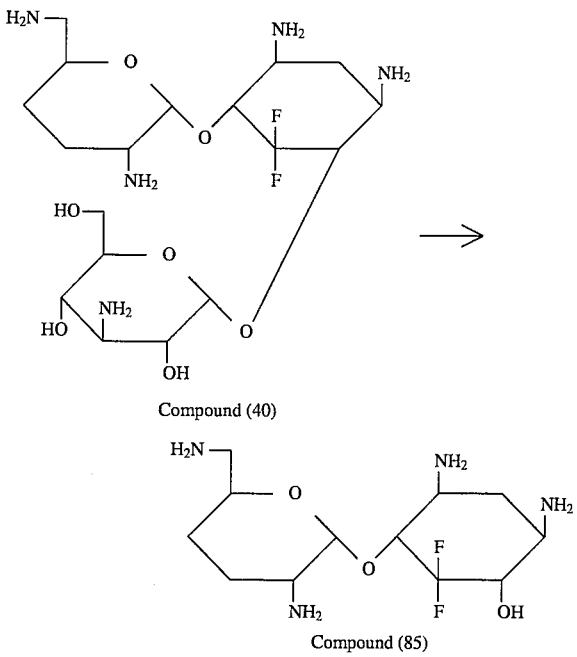

Compound (85)

5,3',4'-Trideoxy-5,5-difluorokanamycin B, namely Compound (40) as obtained in Example 9(c) (10.0 g) is dissolved in a 4N aqueous hydrochloric acid solution (200 ml). The reaction was conducted at 100° C. for 1 hour to hydrolyze Compound (40).

The resulting reaction solution was concentrated under reduced pressure and then neutralized with aqueous ammonia. The neutralized solution was passed through a column of the resin "Amberlite CG-50" ($NH_4^+$-form) (850 ml) on which the reaction product was adsorbed. The resin column was washed with water and then eluted gradiently with 0.2N aqueous ammonia. Fractions of the eluate containing the intended compound were collected, combined together and then concentrated to afford 4.72 g (yield: 72%) of the titled Compound (85) as a solid.

$[\alpha]_D^{20}$+790 (c 1.0, water)

INDUSTRIAL APPLICABILITY

5-Deoxy-5,5-difluoro derivatives of the aminoglycosidic antibiotics and their 1-N-(α-hydroxy-ω-aminoalkanoyl)-derivatives according to this invention exhibit high antibacterial activity against bacteria sensitive to aminoglycosidic antibiotics and against bacteria resistant to aminoglycosidic antibiotics, and also, they show significantly reduced toxicity, so that they are useful as antibacterial agent for therepeutic treatment of bacterial infections.

We claim:

1. A 4-O-(aminoglycosyl)- or 4,6-di-O-(aminoglycosyl)-

2,5-dideoxy-5,5-difluorostreptamine derivative represented by the formula

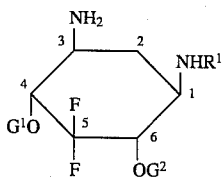 (I)

wherein $R^1$ is a hydrogen atom, an alkyl group of 1–4 carbon atoms or an α-hydroxy-ω-aminoalkanoyl group of the formula

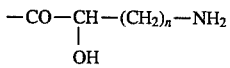

where n is an integer of 1 to 3, $G^1$ is either an aminoglycosyl group of the formula

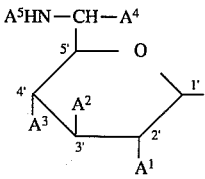 (i)

where $A^1$ is a hydroxyl group or amino group, $A^2$ and $A^3$ are independently a hydrogen atom, hydroxyl group or fluoro group, $A^4$ is a hydrogen atom or methyl group, and $A^5$ is a hydrogen atom or methyl group, or $G^2$ is a 4'-eno-aminoglycosyl group of the formula

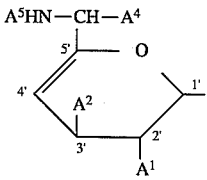 (ii)

where $A^1$, $A^2$, $A^4$ and $A^5$ independently have the same meanings as defined above, and $G^2$ is either a hydrogen atom, or a 3"-amino-3"-deoxyglycosyl group of the formula

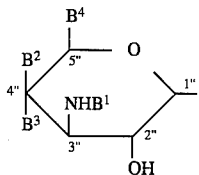 (iii)

where $B^1$ is a hydrogen atom or methyl group, $B^2$ and $B^3$ are independently a hydrogen atom, hydroxyl group or methyl group, and $B^4$ is a hydrogen atom or a hydroxymethyl group ($-CH_2OH$), or $G^2$ is a 2"-amino-2"-deoxyglycosyl group of the formula

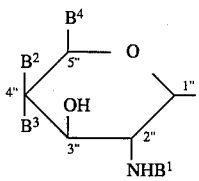 (iv)

where $B^1$, $B^2$, $B^3$ and $B^4$ independently have the same meanings as defined above, or a pharmaceutically acceptable acid addition salt of said derivative.

2. A streptamine derivative as claimed in claim 1, which is a 4,6-di-O-(aminoglycosyl)-2,5-dideoxy-5,5-difluorostreptamine derivative represented by the formula

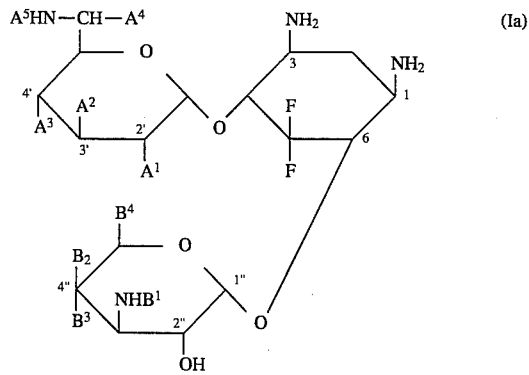 (Ia)

wherein $A^1$, $A^2$, $A^3$, $A^4$ and $A^5$, as well as $B^1$, $B^2$, $B^3$ and $B^4$ have the same meanings as defined for the formula (I) described in claim 1, and which is such a compound belonging to a derivative of kanamycin A, a derivative of kanamycin B, a derivative of gentamicin $C_1$, a derivative of gentamicin $C_{1a}$ or a derivative of gentamicin $C_2$ or a derivative of sagamicin.

3. A streptamine derivative as claimed in claim 1, which is a compound represented by the formula

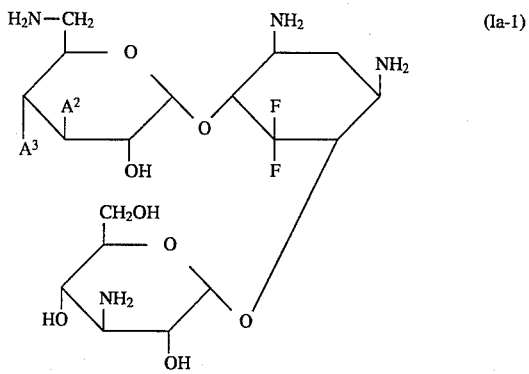 (Ia-1)

wherein (i) $A^2$ and $A^3$ are each a hydroxyl group, or (ii) $A^2$ is a hydrogen atom and $A^3$ is a hydroxyl group, or (iii) $A^2$ and $A^3$ are each a hydrogen atom, and which is namely (i) 5-deoxy-5,5-difluorokanamycin A, or (ii) 5,3'-dideoxy-5,5-difluorokanamycin A, or (iii) 5,3',4'-trideoxy-5,5-difluorokanamycin A.

4. A streptamine derivative as claimed in claim 1, which is a compound represented by the formula

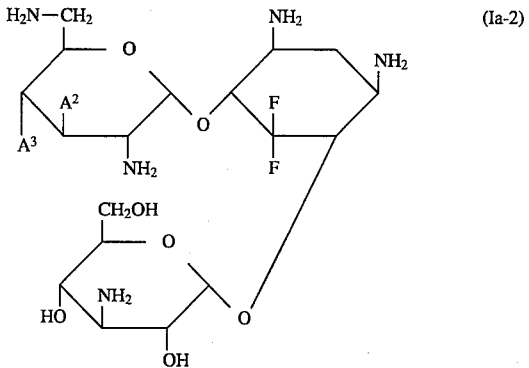 (Ia-2)

wherein (i) $A^2$ and $A^3$ are each a hydroxyl group, or (ii) $A^2$ is a hydrogen atom and $A^3$ is a hydroxyl group, or (iii) $A^2$ and $A^3$ are each a hydrogen atom, or (iv) $A^2$ is a fluoro group and $A^3$ is a hydroxyl group, or (v) $A^2$ is a fluoro group and $A^3$ is a hydrogen atom, and which is namely (i) 5-deoxy- 5,5-difluorokanamycin B, or (ii) 5,3'-dideoxy-5,5-difluoro-kanamycin B, or (iii) 5,3',4'-trideoxy-5,5-difluorokanamycin B, or (iv) 5,3'-dideoxy-5,5,3'-trifluorokanamycin B, or (v) 5,3',4'-trideoxy-5,5,3'-trifluorokanamycin B.

5. A streptamine derivative as claimed in claim 1, which is a compound represented by the formula

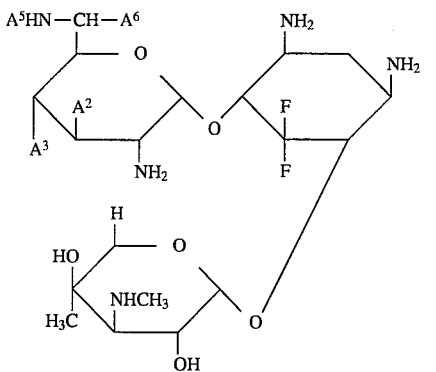

wherein (i) $A^2$ and $A^3$ are each a hydrogen atom and $A^4$ and $A^5$ are each a methyl group, or (ii) $A^2$, $A^3$, $A^4$ and $A^5$ are all and each a hydrogen atom, or (iii) $A^2$, $A^3$ and $A^5$ are all and each a hydrogen atom and $A^4$ is methyl group, or (iv) $A^2$, $A^3$ and $A^4$ are all and each a hydrogen atom and $A^5$ is methyl group, and which is namely (i) 5-deoxy-5,5-difluorogentamicin $C_1$, or (ii) 5-deoxy-5,5-difluorogentamicin $C_{1a}$, or (iii) 5-deoxy-5,5-difluorogentamicin $C_2$, or (iv) 5-deoxy-5,5-difluorosagamicin.

6. A streptamine derivative as claimed in claim 1, which is a compound represented by the formula

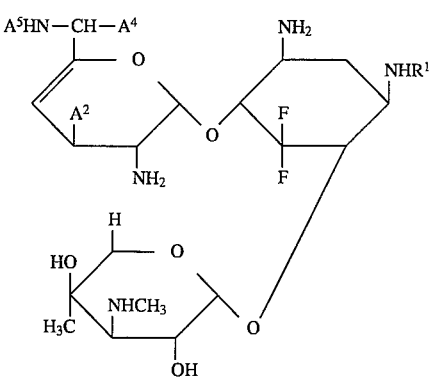

wherein (i) $R^1$ is a hydrogen atom and $A^2$, $A^4$ and $A^5$ are all and each a hydrogen atom, or (ii) $R^1$ is ethyl group and $A^2$, $A^4$ and $A^5$ are all and each a hydrogen atom, and which is namely (i) 5-deoxy-5,5-difluorosisomicin or (ii) 5-deoxy-5,5-difluoronetilmicin.

7. A streptamine derivative as claimed in claim 1, which is a 1-N-(α-hydroxy-ω-aminoalkanoyl)-4,6-di-O-(aminoglycosyl)-2,5-dideoxy-5,5-difluorostreptamine derivative represented by the formula

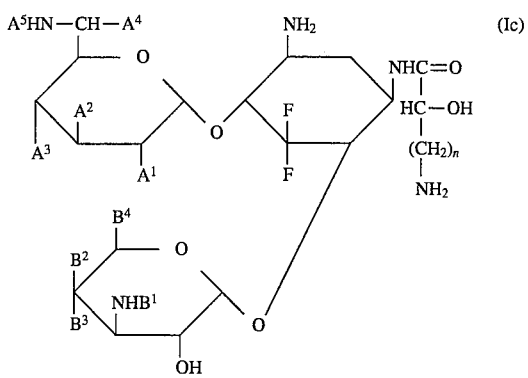

wherein n is an integer of 1 to 3, and $A^1$, $A^2$, $A^3$, $A^4$ and $A^5$ as well as $B^1$, $B^2$, $B^3$ and $B^4$ respectively have the same meanings as defined for the formula (I) described in claim 1.

8. A streptamine derivative as claimed in claim 1, which is a compound represented by the formula

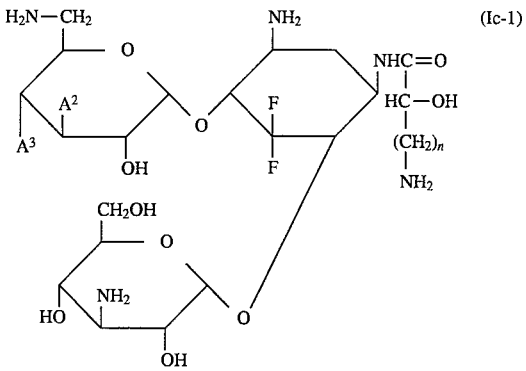

wherein n is an integer of 1 to 3, and (i) $A^2$ and $A^3$ are each a hydroxyl group, or (ii) $A^2$ is a hydrogen atom and $A^3$ is hydroxyl group, or (iii) $A^2$ and $A^3$ are each a hydrogen atom, and which is namely a 1-N-(α-hydroxy-ω-aminoalkanoyl) derivative of anyone of (i) 5-deoxy-5,5-difluorokanamycin A or (ii) 5,3'-dideoxy-5,5-difluorokanamycin A or (iii) 5,3', 4'-trideoxy-5,5-difluorokanamycin A.

9. A streptamine derivative as claimed in claim 1, which is a compound represented by the formula

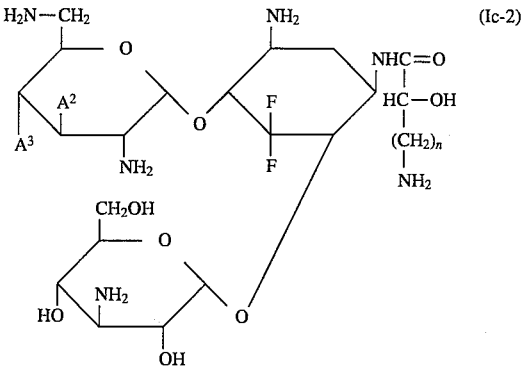

wherein n is an integer of 1 to 3, and (i) $A^2$ and $A^3$ are each a hydroxyl group, or (ii) $A^2$ is a hydrogen atom and $A^3$ is hydroxyl group, or (iii) $A^2$ and $A^3$ are each a hydrogen atom, or (iv) $A^2$ is a fluoro group and $A^3$ is hydroxyl group, or (v) $A^2$ is a fluoro group and $A^3$ is a hydrogen atom, and which is namely a 1-N-(α-hydroxy-ω-aminoalkanoyl) derivative of anyone of (i) 5-deoxy-5,5-difluorokanamycin B or (ii) 5,3'-dideoxy-5,5-difluorokanamycin B or (iii) 5,3',4'-trideoxy-5,5-difluorokanamycin B or (iv) 5,3'-dideoxy-5,5,3'-trifluorokanamycin B or (v) 5,3',4'-trideoxy-5,5,3'-trifluorokanamycin B.

10. A streptamine derivative as claimed in claim 1, which is a compound represented by the formula

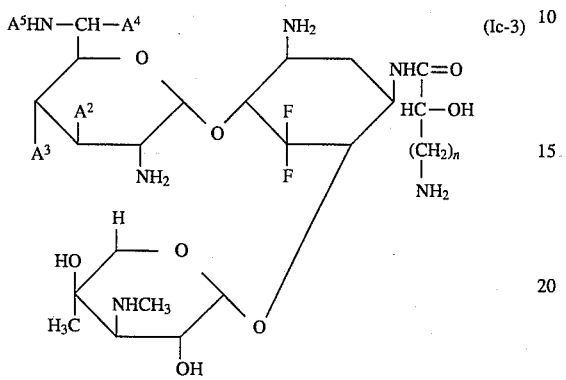

wherein n is an integer of 1 to 3, and (i) $A^2$ and $A^3$ are each a hydrogen atom and $A^4$ and $A^5$ are each a methyl group, or (ii) $A^2$, $A^3$, $A^4$ and $A^5$ are all and each a hydrogen atom, or (iii) $A^2$, $A^3$ and $A^5$ are all and each a hydrogen atom and $A^4$ is methyl group, or (iv) $A^2$, $A^3$ and $A^4$ are all and each a hydrogen atom and $A^5$ is methyl group, and which is a 1-N-(α-hydroxy-ω-aminoalkanoyl) derivative of anyone of (i) 5-deoxy-5,5-difluorogentamicin $C_1$ or (ii) 5-deoxy-5,5-difluorogentamicin $C_{1a}$ or (iii) 5-deoxy-5,5-difluorogentamicin $C_2$ or (iv) 5-deoxy-5,5-difluorosagamicin.

11. A streptamine derivative as claimed in claim 1, which is 5-deoxy-5,5-difluoroseldomycin factor 3 represented by the formula

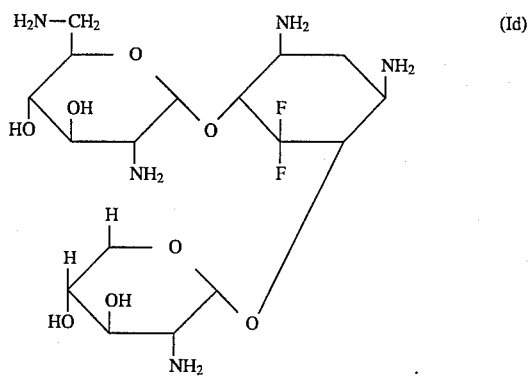

12. An antibacterial composition, characterized in that said composition comprises a 4-O-(aminoglycosyl)- or 4,6-di-O-(aminoglycosyl)-2,5-dideoxy-5,5-difluorostreptamine derivative represented by the formula

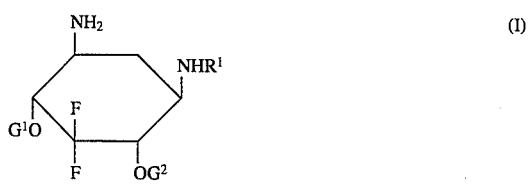

wherein $R^1$, $G^1$ and $G^2$ respectively have the same meanings as defined for the formula (I) described in claim 1, as the active ingredient in an antibacterially effective amount, in association with a pharmaceutically acceptable carrier for the active ingredient.

* * * * *